United States Patent
Maupin-Furlow et al.

(10) Patent No.: US 7,326,551 B2
(45) Date of Patent: Feb. 5, 2008

(54) CLONING AND SEQUENCING OF PYRUVATE DECARBOXYLASE (PDC) GENES FROM BACTERIA AND USES THEREFOR

(75) Inventors: Julie A. Maupin-Furlow, Gainesville, FL (US); Lee Ann Talarico, Gainesville, FL (US); Krishnan Chandra Raj, Tamil Nadu (IN); Lonnie O. Ingram, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 881 days.

(21) Appl. No.: 10/136,960

(22) Filed: Apr. 30, 2002

(65) Prior Publication Data

US 2003/0087368 A1    May 8, 2003

Related U.S. Application Data

(60) Provisional application No. 60/288,638, filed on May 4, 2001, provisional application No. 60/288,671, filed on May 4, 2001, provisional application No. 60/288,698, filed on May 4, 2001, provisional application No. 60/288,622, filed on May 4, 2001, provisional application No. 60/288,699, filed on May 4, 2001.

(51) Int. Cl.
*C12N 9/02*   (2006.01)
*C12N 15/00*  (2006.01)
*C12Q 1/00*   (2006.01)
*C12P 7/24*   (2006.01)
*C07H 21/04*  (2006.01)

(52) U.S. Cl. .................... 435/189; 435/4; 435/147; 435/161; 435/183; 435/252.3; 435/320.1; 536/23.2

(58) Field of Classification Search ............. 435/183, 435/189, 252.3, 320.1, 4, 147; 536/23.2
See application file for complete search history.

(56) References Cited

U.S. PATENT DOCUMENTS

| 3,990,944 A |   | 11/1976 | Gauss et al. |
| 5,643,758 A | * | 7/1997  | Guan et al. ............... 435/69.7 |
| 6,225,098 B1 | * | 5/2001 | Wallis et al. ............... 435/189 |

FOREIGN PATENT DOCUMENTS

| WO | WO 96/37620 A | 11/1996 |
| WO | WO 98/39457   | 9/1998  |
| WO | WO 98/39457 A | 9/1998  |

OTHER PUBLICATIONS

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Candy et al. Accession X59558. Feb. 17, 1997.*
Bruhn et al. Accession A58392. Mar. 5, 1998.*
Manning . Accession A64082. Mar. 29, 1999.*
Ingram et al. Biotechnol Prog. Sep.-Oct. 1999;15(5):855-66.*
Maas et al. Journal of General Microbiology (1992), 138(4), 795-802 (ABSTRACT).*
GenBank Accession M15393, Conway T et al., Apr. 26, 1993.
GenPept Accession 1811220A, Miczka G et al., Nov. 19, 1996.
GenBank Accession AF285632, Patten CL et al., Aug. 17, 2000.
GenBank Accession D90214, Koga J et al., Feb. 7, 1999.
Alvarez M E et al: "The 59-KDA Polypeptide Constitutent of 8-10-NM Cytoplasmic Filamentsin Neurospora Crassa is a Pyruvate Decarboxylae" Gene, Elsevier Biomedical Press. Amsterdam, NL, vol. 130, 1993, pp. 253-258, XP001019088, ISSN: 0378-1119.
Database UniProt "Online!, Feb. 1, 1994, "Pyruvate decarboxylase (EC 4.1.1.1) 8-10 nm cytoplasmic filament—associated protein) (P59NC)." XP002342297 retrived from EBI accession No. UNIPROT: PDC_NEUCR, Database accession No. PDC_NEUCR.
Database EMBL 'Online!, Jun. 4, 1993, "Neurospora crassa pyruvate decarboxylase (cfp) mRNA, complete cds." XP002342310, retrieved from EBI accession No. EM_PRO:NCCFPX, Database accession No. NCCFPX.
Database UniProt 'Online!, Nov. 1, 1997, "Probable pyruvate decarboxylase C1F8.07c (EC 4.1.1.1)." XP002342298, retrived from EBI accession No. UNIPROT: PDC2_SCHPO, Database accession No. PDC2_SCHPO.
Database UniProt 'Online!, May 1, 1997, "Schizosaccharomyces pombe." XP002342299, retrived from EBI accession No. UNIPROT: P78913, Database accession No. P78913.
Database UniProt 'Online!, Oct. 1, 2000, "Pyruvate decarboxylase-like protein (At5g01330)," XP002342300, retrieved from EBI accession No. UNIPROT: Q9M039, Database accession No. Q9M039.
Database EMBL 'Online!, Sep. 19, 1987, "Z.mobilis pyruvate decarboxylase gene, complete cds." XP002342301, retrived from EBI accession No. EM_PRO:ZMPDCX, Database accession No. ZMPDCX.
Neale A D et al: "Nucleotide sequence of the pyruvate decarboxylase gene from *Zymomonas mobilis*." Nucleic Acids Research. Feb. 25, 1987, vol. 15, No. 4, Feb. 25, 1987, pp. 1753-1761, XP002342267, ISSN: 0305-1048.
Conway et al: "Promoter and nucleotide sequence of the *Zymomonas mobilis* pyruvate decarboxylase", Journal of Bacteriology, Washington, DC, US, No. 169, 1987, pp. 949-954, XP002071434, ISSN: 0021-9193.

(Continued)

*Primary Examiner*—Ponnathapu Achutamurthy
*Assistant Examiner*—Christian L Fronda
(74) *Attorney, Agent, or Firm*—Edwards Angell Palmer & Dodge LLP; Peter C. Lauro, Esq.

(57) ABSTRACT

The invention provides isolated nucleic acids molecules which encode pyruvate decarboxylase enzymes having improved decarboxylase activity, substrate affinity, thermostability, and activity at different pH. The nucleic acids of the invention also have a codon usage which allows for high expression in a variety of host cells. Accordingly, the invention provides recombinant expression vectors containing such nucleic acid molecules, recombinant host cells comprising the expression vectors, host cells further comprising other ethanologenic enzymes, and methods for producing useful substances, e.g., acetaldehyde and ethanol, using such host cells.

51 Claims, 13 Drawing Sheets

OTHER PUBLICATIONS

Databse EMBL 'Online!, Sep. 19, 1987, "*Zymomonas mobilis* pyruvate decarboxylase gene, complete cds." XP002342302 retrieved from EBI accession No. EM_PRO:ZMPDC, Database accession No. ZMPDC.

Lowe S E et al: "Purification and Characterization of Pyruvate Decarboxylase from *Sarcina ventriculi*" Journal of General Microbiology, vol. 138, No. 4, 1992, pp. 803-807, XP002354875, ISSN: 0022-1287.

Jason S. Cesario: "Cloning and Characterization of the Pyruvate Decarboxylase Gene from *Sarcina ventriculi*", Journal of Undergraduate Research, vol. 1, No. 4, 2000, pp. 1-3, XP002354876.

Database EMBL 'Online!, Oct. 23, 1992, "*Z. mobilis*, gene for pyruvate decarboxylase" XP002354886, retrived from EBI accession No. EM_PRO:ZMPYRDEC, Database accession No. ZMPYRDEC.

Database EMBL 'Online!, Jul. 6, 1989, "*Z. mobilis* pdc gene encoding pyruvate decarboxylase, complete cds." XP002354887, retrived from EBI accession No. EM_PRO:ZMDPCA. Database accession No. ZMDPCA.

Database UniProt 'Online!, Jan. 1, 1988, "Pyruvate decarboxylase (EC 4.1.1.1) (PDC)." XP002354888, retrived from EBI accession No. UNIPROT:PDC_ZYMMO, Database accession No. PDC_ZYMMO.

Database Geneseq 'Online!, Feb. 8, 2001, "Human ORFX ORF1175 polynucleotide sequence SEQ ID No. 2349." XP002354889, retrived from EBI accession No. GSN:AAC75620.

Database EMBL 'Online!, Mar. 27, 2000, "EST323719 *L. hirsutum* trichome, Cornell University *Lycopersicon hirsutum* cDNA clone cLHT22H195', mRNA sequence." XP002354890, retrived from EBI accession No. EM_EST: AW617308, Database accession No. AW617308.

Database EMBL "Online! Mar. 29, 2000, "EST313279 tomatoe root during/after fruit set, Cornell University *Lycopersicon esculentum* cDNA close cLEX1518 5', mRNA sequence." XP002354891, retrived from EBI accession No. EM_EST:AW622491, Database accession No. AW622491.

Database EMBL 'Online!' Feb. 18, 2000, "*Anopheles gambiae* GSS T7 end of clone 22K15 of NotreDamel library from strain PEST of *Anopheles gambiae* (African malaria mosquito)", XP002354892, retrived from EBI accession No. EM_GSS:CNS01MWC, Database accession No. CNS01MWC.

Talarico Lee A et al: "Production of the gram-positive *Sarcina ventriculi* pyruvate decarboxylase in *Escherichia coli*" Microbiology (Reading), vol. 147, No. 9, Sep. 2001, pp. 2425-2435, XP002354877, ISSN: 1350-0872.

Chandra Raj K et al: "Pyruvate decarboxylase: a key enzyme for the oxidative metabolism of lactic acid by *Acetobacter pasteurianus*." Archives of Microbiology. Dec. 2001, vol. 176, No. 6, Dec. 2001, pp. 443-451, XP002354878, ISSN: 0302-8933.

Raj Krishnan Chandra et al: "Cloning and characterization of the *Zymobacter palmae* pyruvate decarboxylase gene (pdc) and comparison to bacterial homologues" Applied and Environmental Microbiology, vol. 68, No. 6, Jun. 2002, pp. 2869-2876, XP002342268, ISSN: 0099-2240.

Alarez, M.E. et al. "The 59-KDA Polypeptide Constituent of 8-10-NM Cytoplasmic Filments in Neurospora Crassa is a Pyruvate Decarboxylase." *Gene, Elsevier Biomedical Press*, Amsterdam, NL, (1993) vol. 130: pp. 253-258 (XP001019088).

Conway et al. "Promoter and Nucleotide Sequence of the *Zymomonas mobilis* Pyruvate Decaroxylase." *Journal of Bacteriology*, Washington, DC, (1987) No. 169, pp. 949-954 (XP002071434).

Neale A.D. et al. "Nucleotide Sequence of the Pyruvate Decarboxylase Gene from *Zymomonas mobilis*." *Nucleic Acids Research*, (1987) vol. 15, No. 4, pp. 1753-1761 (XP002342267).

Raj K.C. et al. "Cloning and Characterization of the *Zymobacter palmae* Pyruvate Decarboxylase Gene (pdc) and Comparison to Bacterial Homologues." *Applied and Environmental Microbiology*, (2002) vol. 68, No. 6, pp. 2869-2876 (XP002342268).

EBI Accession No. ZMPDC (XP002342302), Sep. 19, 1987.

EBI Accession No. ZMPDCX (XPD02342301), Sep. 19, 1987.

EPI Accession No. NCCFPX (XP002342310), Jun. 4, 1993.

EPI Accession No. PDC_NEUCR (XP002342297), Feb. 1, 1994.

EPI Accession No. P78913 (XP002342299), May 1, 1997.

EPI Accession No. PDC2_SCHPO (XP002342298), Nov. 1, 1997.

EPI Accession No. Q9M039 (XP002342300), Oct. 1, 2000.

EPO No. 02789143.1 Partial European Search Report, Sep. 9, 2005.

Argos, P., M. G. Rossman, U. M. Grau, H. Zuber, G. Frank, and J. D. Tratschin. "Thermal stability and polypeptide structure." *Biochemistry* (1979) 18:5698-5703.

Attwood, T. K. and Miller, C. J. "What craft is best in informatics?" *Comput. Chem.* (2001), 25(4): 329-339.

Barbosa, M. F. S. and L. O. Ingram. "Expression of the *Zymomonas mobilis* alcohol dehydrogenase II (*adhB*) and pyruvate decarboxylase (*pdc*) genes in *Bacillus*." *Curr. Microbiol.* (1994) 28:279-282.

Bringer-Meyer, S., Schimz,K.-L., & Sahm,H. (1986). Pyruvate decarboxylase from *Zymomonas mobilis*. Isolation and partial characterization. *Arch.Microbiol.* 146, 105-110.

Bradshaw, R. A., W. W. Brickey, K. W. Walker. "N-terminal processing: the methionine aminopeptidase and N"-acetyl transferase families." *Trends Biochem.Sci.* (1998) 23:263-267.

Bruhn, H. et al. Accession A58392. Mar. 5, 1998.

Candy, J. M. and R. G. Duggleby . 1998. Structure and properties of pyruvate decarboxylase and site-directed mutagenesis of the *Zymomonas mobilis* enzyme. Biochim.Biophys.Acta 1385:323-338.

Candy, J. M. et al. Accession X59558. Feb. 17, 1997.

Deng, M. D. and J. R. Coleman. 1999. Ethanol synthesis by genetic engineering in cyanobacteria. Appl.Environ.Microbiol. 65:523-528.

Diefenbach, R. J. and R. G. Duggleby. 1991. Pyruvate decarboxylase from *Zymomonas mobilis*. Structure and re-activation of apoenzyme by the cofactors thiamin diphosphate and magnesium ion. Biochem.J. 276:439-445.

Gold, R. S., M. M. Meagher, S. Tong, R. W. Hutkins, and T. Conway. 1996. Cloning and expression of the *Zymomonas mobilis* "production of ethanol" genes in *Lactobacillus casei*. Curr. Microbiol. 33:256-260.

Gottschalk, G. 1986. Catabolic activities of aerobic heterotrophs, p. 141-177. *In* Bacterial Metabolism. Springer-Verlag, New York.

Harwood, C. R. and S. M. Cutting. 1990. *In* Molecular Biological Methods for *Bacillus*. Wiley, New York.

Hawkins CF, Borges A, Perham RN (1989) A common structural motif in thiamin pyrophosphate-binding enzymes. FEBS Lett 255:77-82.

Henaut, A. and A. Danchin. 1996. Analysis and predictions from *Escherichia coli* sequence, or *E. coli* in silico, p. 2047-2066. *In* F. C. Neidhardt and et al. (eds.), *Escherichia coli* and *Salmonella* Cellular and Molecular Biology. ASM Press, Washington, DC.

Himmel et al. Advanced Bioethanol Production Technologies: A Perspective. ACS Symposium Series 666. Washington, D.C. Amer. Chem. Soc.(1997), Ch. 1. pp. 2-45.

Huang, C. Y., A. K. Chang, P. F. Nixon, and R. G. Duggleby. 2001. Site-directed mutagenesis of the ionizable groups in the active site of *Zymomonas mobilis* pyruvate decarboxylase: effect on activity and Ph dependence. Eur.J.Biochem. 268:3558-3565.

Ingram et al. Appl. Environ. Microbiol. (1987) 53: 2420-2425.

Ingram, L. O., H. C. Aldrich, A. C. Borges, T. B. Causey, A. Martinez, F. Morales, A. Saleh, S. A. Underwood, L. P. Yomano, S. W. York, J. Zaldivar, and S. Zhou. 1999. Enteric bacterial catalysts for fuel ethanol production. Biotechnol.Prog. 15 :855-866.

Irwin, D. C., S. Zhang, and D. B. Wilson. 2000. Cloning, expression and characterization of a Family 48 exocellulase, Ce148A, from *Thermobifida fusca*. Eur.J.Biochem. 267:4988-4997.

Jornvall H, Persson B, Jeffery J (1987) Characteristics of alcohol/polyol dehydrogenases. The zinc-containing long-chain alcohol dehydrogenases. Eur J Biochem 167:195-201.

Kenworthy, P. and D. D. Davies . 1976. Kinetic aspects of regulation of pyruvic decarboxylase. Phytochemistry 15:279-282.

King, T. E. and V. H. Cheldelin. 1953. Pyruvic carboxylase of *Acetobacter suboxydans*. J.Biol.Chem. 208:821-831.

Kondo, K., T. Beppu, and S. Horinouchi. 1997. Cloning, sequencing, and characterization of the gene encoding the smallest subunit of the three-component membrane-bound alcohol dehydrogenase from *Acetobacter pasteurianus*. J.Bacteriol. 177:5048-5055.

Konig, S. 1998. Subunit structure, function and organisation of pyruvate decarboxylases from various organisms. Biochim. Biophys.Acta 1385:271-286.

Lee, T. C. and P. J. Langston-Unkefer. 1985. Pyruvate decarboxylase from *Zea mays* L. I. Purification and partial characterization from mature kernals and anaerobically treated roots. Plant Physiol. 79:242-247.

Lowe, S. E. and J. G. Zeikus. 1992. Purification and characterization of pyruvate decarboxylase from *Sarcina ventriculi*. J.Gen. Microbiol. 138:803-807.

Lu, G., D. Dobritzsch, S. Baumann, G. Schneider, and S. Konig. 2000. The structural basis of substrate activation in yeast pyruvate decarboxylase. A crystallographic and kinetic study. Eur.J.Biochem. 267:861-868.

Lynd et al. Science (1991) 251: 1318-1323.

Maas, et al. *Journal of General Microbiology*. (1992), 138(4), 795-802 (Abstract).

Manning, K. Accession A64082. Mar. 29, 1999.

Matthews, B. W. 1993. Structural and genetic analysis of polypeptide stability. Annu.Rev.Biochem. 62:139-160.

Mozhaev, V. V. and K. Martinek . 1984. Structure-stability relationships in polypeptides: new approaches to stabilizing enzymes. Enzyme Microb.Technol. 6:50-59.

Mücke, U., S. Konig, and G. Hubner. 1995. Purification and characterisation of pyruvate decarboxylase from pea seeds (*Pisum sativum* cv. Miko). Biol.Chem.Hoppe Seyler 376:111-117.

Neale, A. D., R. K. Scopes, R. E. Wettenhall, and N. J. Hoogenraad. 1987. Pyruvate decarboxylase of *Zymomonas mobilis*: isolation, properties, and genetic expression in *Escherichia coli*. J.Bacteriol. 169:1024-1028.

Notenboom, V., C. Birsan, R. A. Warren, S. G. Withers, and D. R. Rose. 1998. Exploring the cellulose/xylan specificity of the beta-1,4-glycanase cex from *Cellulomonas fimi* through crystallography and mutation. Biochemistry 37:4751-4758.

Okamoto et al. Appl. Microbiol. Biotechnol. (1994) 42: 563-568.

Olsson et al. Enzyme Microb. Technol. (1996) 18: 312-331.

Philippidis, G. "Cellulase Production Technology: Evaluation of Current Status." ACS Symposium Series 566. Washington, D. C. Amer. Chem. Soc. (1994) Ch. 9. pp. 188-217.

Ponting, C. P. "Issues in predicting protein function form sequence." *Brief. Bioinform.* (2001), 2(1): 19-29.

Raj, K. C., L. O. Ingram, and J. A. Maupin-Furlow. 2001. Pyruvate decarboxylase: a key enzyme for the oxidative metabolism of lactic acid by *Acetobacter pasteurianus*. Arch.Microbiol. 176:443-451.

Reynen M, Sahm H (1988) Comparison of the structural genes for pyruvate decarboxylase in different *Zymomonas mobilis* strains. J Bacteriol 170:3310-3313.

Saito et al. J. Ferment. Bioeng. (1990) 69: 282-286.

Sanger, F., S. Nicklen, and A. R. Coulson. 1977. DNA sequencing with chain-terminating inhibitors. Proc.Natl.Acad.Sci.U.S.A. 74:5463-5467.

Schenk, G., F. J. Leeper, R. England, P. F. Nixon, and R. G. Duggleby. 1997. The role of His113 and His 114 in pyruvate decarboxylase from *Zymomonas mobilis*. Eur.J.Biochem. 248:63-71.

Sheehan. ACS Symposium Series No. 566 (1994) ACS Press, 1-52.

Southern, E. M. (1975). Detection of specific sequences among DNA fragments separated by gel electrophoresis. *J. Mol. Biol.* 98, 503-517.

Su et al. Biotechnol. Lett. (1993) 15: 979-984.

Wyman et al. Amer. Chem. Soc. Symp. (1995) 618: 272-290.

Talarico, L. A., L. O. Ingram, and J. A. Maupin-Furlow. 2001. Production of the Gram-positive *Sarcina ventriculi* pyruvate decarboxylase in *Escherichia coli* . Microbiology 147:2425-2435.

Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680.

Thurner C, Vela C, Thony-Meyer L, Meile L, Teuber M (1997) Biochemical and genetic characterization of the acetaldehyde dehydrogenase complex from *Acetobacter europaeus*. Arch Microbiol 168:81-91.

Tobias, J. W., T. E. Shrader, G. Rocap, and A. Varshavsky. 1991. The N-end rule in bacteria. Science 254:1374-1377.

Vieille, C. and G. J. Zeikus. 2001. Hyperthermophilic enzymes: sources, uses, and molecular mechanisms for thermostability. Microbiol.Mol.Biol.Rev. 65:1-43.

Database DNA, Accession No. AR095552, Bruhn et al., Sep. 8, 2000.

* cited by examiner

Fig. 4-1

```
atgtataccgttggtatgtacttggcagaacgcctagcccagatcggcctgaaacaccac
 M  Y  T  V  G  M  Y  L  A  E  R  L  A  Q  I  G  L  K  H  H
tttgccgtggccggtgactacaacctggtgttgcttgatcagctcctgctgaacaaagac
 F  A  V  A  G  D  Y  N  L  V  L  L  D  Q  L  L  L  N  K  D
atggagcaggtctactgctgtaacgaacttactgcggctttagcgccgaaggttacgct
 M  E  Q  V  Y  C  C  N  E  L  T  A  A  L  A  P  K  V  T  L
cgtgcacgtggtgccgccgctgccatcgtcacgttcagcgtaggtgctatctctgcaatg
 R  A  R  G  A  A  A  A  I  V  T  F  S  V  G  A  I  S  A  M
aacgccatcggtggcgcctatgcagaaaacctgccggtcatcctgatctctggctcaccg
 N  A  I  G  G  A  Y  A  E  N  L  P  V  I  L  I  S  G  S  P
aacaccaatgactacggcacaggccacatcctgcaccacaccattggtactactgactat
 N  T  N  D  Y  G  T  G  H  I  L  H  H  T  I  G  T  T  D  Y
aactatcagctggaaatggtaaaacacgttacctgcgcacgtgaaagcatcgtttctgcc
 N  Y  Q  L  E  M  V  K  H  V  T  C  A  R  E  S  I  V  S  A
gaagaagcaccggcaaaaatcgaccacgtcatccgtacggctctacgtgaacgcaaaccg
 E  E  A  P  A  K  I  D  H  V  I  R  T  A  L  R  E  R  K  P
gcttatctggaaatcgcatgcaacgtcgctggcgctgaatgtgttcgtccgggcccgatc
 A  Y  L  E  I  A  C  N  V  A  G  A  E  C  V  R  P  G  P  I
aatagcctgctgcgtgaactcgaagttgaccagaccagtgtcactgccgctgtagatgcc
 N  S  L  L  R  E  L  E  V  D  Q  T  S  V  T  A  A  V  D  A
gccgtagaatggctgcaggaccgccagaacgtcgtcatgctggtcggtagcaaactgcgt
 A  V  E  W  L  Q  D  R  Q  N  V  V  M  L  V  G  S  K  L  R
gccgctgccgctgaaaaacaggctgttgccctagcggaccgcctgggctgcgctgtcacg
 A  A  A  A  E  K  Q  A  V  A  L  A  D  R  L  G  C  A  V  T
atcatggctgccgaaaaaggcttcttcccggaagatcatccgaacttccgcggcctgtac
 I  M  A  A  E  K  G  F  F  P  E  D  H  P  N  F  R  G  L  Y
tggggtgaagtcagctccgaaggtgcacaggaactggttgaaaacgccgatgccatcctg
 W  G  E  V  S  S  E  G  A  Q  E  L  V  E  N  A  D  A  I  L
tgtctggcaccggtattcaacgactatgctaccgttggctggaactcctggccgaaaggc
 C  L  A  P  V  F  N  D  Y  A  T  V  G  W  N  S  W  P  K  G
gacaatgtcatggtcatggacaccgaccgcgtcactttcgcaggacagtccttcgaaggt
 D  N  V  M  V  M  D  T  D  R  V  T  F  A  G  Q  S  F  E  G
ctgtcattgagcaccttcgccgcagcactggctgagaaagcaccttctcgcccggcaacg
 L  S  L  S  T  F  A  A  A  L  A  E  K  A  P  S  R  P  A  T
actcaaggcactcaagcaccggtactgggtattgaggccgcagagcccaatgcaccgctg
 T  Q  G  T  Q  A  P  V  L  G  I  E  A  A  E  P  N  A  P  L
accaatgacgaaatgacgcgtcagatccagtcgctgatcacttccgacactactctgaca
 T  N  D  E  M  T  R  Q  I  Q  S  L  I  T  S  D  T  T  L  T
gcagaaacaggtgactcttggttcaacgcttctcgcatgccgattcctggcggtgctcgt
 A  E  T  G  D  S  W  F  N  A  S  R  M  P  I  P  G  G  A  R
gtcgaactggaaatgcaatggggtcatatcggttggtccgtaccttctgcattcggtaac
 V  E  L  E  M  Q  W  G  H  I  G  W  S  V  P  S  A  F  G  N
gccgttggttctccggagcgtcgccacatcatgatggtcggtgatggctcttttccagctg
 A  V  G  S  P  E  R  R  H  I  M  M  V  G  D  G  S  F  Q  L
actgctcaagaagttgctcagatgatccgctatgaaatcccggtcatcatcttcctgatc
 T  A  Q  E  V  A  Q  M  I  R  Y  E  I  P  V  I  I  F  L  I
```

Fig. 4-2

```
aacaaccgcggttacgtcatcgaaatcgctatccatgacggcccttacaactacatcaaa
 N  N  R  G  Y  V  I  E  I  A  I  H  D  G  P  Y  N  Y  I  K
aactggaactacgctggcctgatcgacgtcttcaatgacgaagatggtcatggcctgggt
 N  W  N  Y  A  G  L  I  D  V  F  N  D  E  D  G  H  G  L  G
ctgaaagcttctactggtgcagaactagaaggcgctatcaagaaagcactcgacaatcgt
 L  K  A  S  T  G  A  E  L  E  G  A  I  K  K  A  L  D  N  R
cgcggtccgacgctgatcgaatgtaacatcgctcaggacgactgcactgaaaccctgatt
 R  G  P  T  L  I  E  C  N  I  A  Q  D  D  C  T  E  T  L  I
gcttggggtaaacgtgtagcagctaccaactctcgcaaaccacaagcgtaa
 A  W  G  K  R  V  A  A  T  N  S  R  K  P  Q  A  -
```

Fig. 5-1

```
                    -35                             -10        ?  ?
gccgtaaattcatatatttTTGAtAtgggttgtccgtcattcaTATAtTggacatttgca    60
                    ttgaca-------N18--------tataat
gaggcgggttttacaatgagcgcaatcgctatcctgcgtctcattggagtattccgacc   120
gtgacctatactgttggcatgtatcttgcagaacgccttgtacagatcgggctgaagcat  180
          M  T  Y  T  V  G  M  Y  L  A  E  R  L  V  Q  I  G  L  K  H   20
cacttcgccgtgggcggcgactacaatctcgttcttctggatcagttgctcctcaacaag  240
 H  F  A  V  G  G  D  Y  N  L  V  L  L  D  Q  L  L  L  N  K    40
gacatgaaacagatctattgctgcaatgagttgaactgtggcttcagcgcggaaggctac  300
 D  M  K  Q  I  Y  C  C  N  E  L  N  C  G  F  S  A  E  G  Y    60
gcccgttctaacggggctgcggcagcggttgtccttcagcgttggcgccatttccgcc   360
 A  R  S  N  G  A  A  A  V  V  T  F  S  V  G  A  I  S  A       80
atgaacgccctcggcggcgcctatgccgaaaacctgccggttatcctgatttccggcgcg  420
 M  N  A  L  G  G  A  Y  A  E  N  L  P  V  I  L  I  S  G  A   100
cccaacagcaatgatcagggcacaggtcatatcctgcatcacacaatcggcaagacggat  480
 P  N  S  N  D  Q  G  T  G  H  I  L  H  H  T  I  G  K  T  D   120
tacagctaccagcttgaaatggcccgtcaggtcacctgtgccgccgaaagcattaccgac  540
 Y  S  Y  Q  L  E  M  A  R  Q  V  T  C  A  A  E  S  I  T  D   140
gctcactccgccccggccaagattgaccacgtcattcgcacggcgctgcgcgagcgtaag  600
 A  H  S  A  P  A  K  I  D  H  V  I  R  T  A  L  R  E  R  K   160
ccggcctatctggacatcgcgtgcaacattgcctccgagccctgcgtgcggcctggccct  660
 P  A  Y  L  D  I  A  C  N  I  A  S  E  P  C  V  R  P  G  P   180
gtcagcagcctgctgtccgagcctgaaatcgaccacacgagcctgaaggccgcagtggac  720
 V  S  S  L  L  S  E  P  E  I  D  H  T  S  L  K  A  A  V  D   200
gccacggttgccttgctgaaaaatcggccagcccccgtcatgctgctgggcagcaagctg  780
 A  T  V  A  L  L  K  N  R  P  A  P  V  M  L  L  G  S  K  L   220
cgggccgccaacgcactggccgcaaccgaaacgctggcagacaagctgcaatgcgcggtg  840
 R  A  A  N  A  L  A  A  T  E  T  L  A  D  K  L  Q  C  A  V   240
accatcatggcggccgcgaaaggcttttttccccgaagaccacgcgggttttccgcggcctg  900
 T  I  M  A  A  A  K  G  F  F  P  E  D  H  A  G  F  R  G  L   260
tactggggcgaagtctcgaaccccggcgtgcaggaactggtggagacctccgacgcactg  960
 Y  W  G  E  V  S  N  P  G  V  Q  E  L  V  E  T  S  D  A  L   280
ctgtgcatcgcccccgtattcaacgactattcaacagtcggctggtcgggcatgcccaag 1020
 L  C  I  A  P  V  F  N  D  Y  S  T  V  G  W  S  G  M  P  K   300
ggccccaatgtgattctggctgagcccgaccgcgtaacggtcgatggccgcgcctatgac 1080
 G  P  N  V  I  L  A  E  P  D  R  V  T  V  D  G  R  A  Y  D   320
ggctttaccctgcgcgccttcctgcaggctctggcggaaaaagccccgcgcgcccggcc  1140
 G  F  T  L  R  A  F  L  Q  A  L  A  E  K  A  P  A  R  P  A   340
tccgcacagaaaagcagcgtcccgacgtgctcgctcaccgcgacatccgatgaagccggt 1200
 S  A  Q  K  S  S  V  P  T  C  S  L  T  A  T  S  D  E  A  G   360
ctgacgaatgacgaaatcgtccgtcatatcaacgccctgctgacatcaaacacgacgctg 1260
 L  T  N  D  E  I  V  R  H  I  N  A  L  L  T  S  N  T  T  L   380
gtggcagaaaccggcgattcatggttcaatgccatgcgcatgaccctggccggtgcgcgc 1320
 V  A  E  T  G  D  S  W  F  N  A  M  R  M  T  L  A  G  A  R   400
gtggaactggaaatgcagtggggccatatcggctggtccgtgccctccgcgttcggcaat 1380
 V  E  L  E  M  Q  W  G  H  I  G  W  S  V  P  S  A  F  G  N   420
```

Fig. 5-2

```
gccatgggctcgcaggaccgccagcatgtggtgatggtaggcgatggctccttccagctt 1440
 A  M  G  S  Q  D  R  Q  H  V  V  M  V  G  D  G  S  F  Q  L   440
accgcgcaggaagtggctcagatggtgcgctacgaactgcccgtcattatctttctgatc 1500
 T  A  Q  E  V  A  Q  M  V  R  Y  E  L  P  V  I  I  F  L  I   460
aacaaccgtggctatgtcattgaaatcgccattcatgacggcccgtacaactatatcaag 1560
 N  N  R  G  Y  V  I  E  I  A  I  H  D  G  P  Y  N  Y  I  K   480
aactgggattacgccggcctgatggaagtcttcaacgccggagaaggccatggacttggc 1620
 N  W  D  Y  A  G  L  M  E  V  F  N  A  G  E  G  H  G  L  G   500
ctgaaagccaccaccccgaaggaactgacagaagccatcgccagggcaaaagccaatacc 1680
 L  K  A  T  T  P  K  E  L  T  E  A  I  A  R  A  K  A  N  T   520
cgcggccccgacgctgatcgaatgccagatcgaccgcacggactgcacggatatgctggtt 1740
 R  G  P  T  L  I  E  C  Q  I  D  R  T  D  C  T  D  M  L  V   540
caatggggccgcaaggttgcctcaaccaacgcgcgcaagaccactctggcctgaaagccc 1800
 Q  W  G  R  K  V  A  S  T  N  A  R  K  T  T  L  A  *         557
gcgggtgtgctcccggcacgcccgaaccgggaaaccggctgacacacacaagacccatc 1860
         →→   →→ ←← ←←                                ─────────
ctgcacaaacaggatgggtcttttttgcataagtcgtgcgccggaaaagccctgctcac 1920
 →→        ←←
gcctgcgcagggccttggctgttagcgcatggagcctgcgacaatggcggaaataatgcc 1980
```

Fig. 6-1

```
                -35                         -10        ?  ??
AAATTTAAAAATAACATCAGATAAATCGTTTATATTAATTTTTACTAAAAGCTATTTAAA

SD
GGTGTATTATATATACATAGTTTATCTTATAAATAAAAAATGAATTGGAGGAAATACATA

ATGAAAATAACAATTGCAGAATACTTATTAAAAAGATTAAAAGAAGTAAATGTAGAGCAT
 M  K  I  T  I  A  E  Y  L  L  K  R  L  K  E  V  N  V  E  H
 M  K  I  I  A  E  Y  L  L  K  R  L  K  E  V  N  V  E  H
ATGTTTGGAGTTCCTGGAGATTATAACTTAGGATTTTTAGATTATGTTGAAGATTCTAAA
 M  F  G  V  P  G  D  Y  N  L  G  F  L  D  Y  V  E  D  S  K
 M  F  G  V  P  G  D  Y  N  L  G  F  L  D  Y  V
GATATTGAATGGGTTGGAAGCTGTAATGGACTTAATGCAGGATATGCAGCAGATGGATAT
 D  I  E  W  V  G  S  C  N  G  L  N  A  G  Y  A  A  D  G  Y

GCAAGACTTAGAGGATTTGGTGTAATACTTACAACTTATGGAGTTGGTTCACTTAGTGCA
 A  R  L  R  G  F  G  V  I  L  T  T  Y  G  V  G  S  L  S  A

ATAAATGCTACAACAGGTTCATTTGCAGAAAATGTTCCAGTATTACATATATCAGGTGTA
 I  N  A  T  T  G  S  F  A  E  N  V  P  V  L  H  I  S  G  V

CCATCAGCTTTAGTTCAACAAAACAGAAAGCTAGTTCACCATTCAACTGCTAGAGGAGAA
 P  S  A  L  V  Q  Q  N  R  K  L  V  H  H  S  T  A  R  G  E

TTCGACACTTTTGAAAGAATGTTTAGAGAAATAACAGAATTTCAATCAATCATAAGCGAA
 F  D  T  F  E  R  M  F  R  E  I  T  E  F  Q  S  I  I  S  E

TATAATGCAGCTGAAGAAATCGATAGAGTTATAGAATCAATATATAAATATCAATTACCA
 Y  N  A  A  E  E  I  D  R  V  I  E  S  I  Y  K  Y  Q  L  P

GGTTATATAGAATTACCAGTTGATATAGTTTCAAAAGAAATAGAAATCGACGAAATGAAA
 G  Y  I  E  L  P  V  D  I  V  S  K  E  I  E  I  D  E  M  K

CCGCTAAACTTAACTATGAGAAGCAACGAGAAAACTTTAGAGAAATTCGTAAATGATGTA
 P  L  N  L  T  M  R  S  N  E  K  T  L  E  K  F  V  N  D  V

AAAGAAATGGTTGCAAGCTCAAAAGGACAACATATTTTAGCTGATTATGAAGTATTAAGA
 K  E  M  V  A  S  S  K  G  Q  H  I  L  A  D  Y  E  V  L  R

GCTAAAGCTGAAAAAGAATTAGAAGGATTTATAAATGAAGCAAAAATCCCAGTAAACACT
 A  K  A  E  K  E  L  E  G  F  I  N  E  A  K  I  P  V  N  T

TTAAGTATAGGAAAGACAGCAGTATCAGAAAGCAATCCATACTTTGCTGGATTATTCTCA
 L  S  I  G  K  T  A  V  S  E  S  N  P  Y  F  A  G  L  F  S

GGAGAAACTAGTTCAGATTTAGTTAAAGAACTTTGCAAAGCTTCTGATATAGTTTTACTA
 G  E  T  S  S  D  L  V  K  E  L  C  K  A  S  D  I  V  L  L

TTTGGAGTTAAATTCATAGATACTACAACAGCTGGATTTAGATATATAAATAAAGATGTT
 F  G  V  K  F  I  D  T  T  T  A  G  F  R  Y  I  N  K  D  V

AAAATGATAGAAATTGGTTTAACTGATTGTAGAATTGGAGAAACTATTTATACTGGACTT
 K  M  I  E  I  G  L  T  D  C  R  I  G  E  T  I  Y  T  G  L
```

Fig. 6-2

```
TACATTAAAGATGTTATAAAAGCTTTAACAGATGCTAAAATAAAATTCCATAACGATGTA
 Y  I  K  D  V  I  K  A  L  T  D  A  K  I  K  F  H  N  D  V

AAAGTAGAAAGAGAAGCAGTAGAAAAATTTGTTCCAACAGATGCTAAATTAACTCAAGAT
 K  V  E  R  E  A  V  E  K  F  V  P  T  D  A  K  L  T  Q  D

AGATATTTCAAACAAATGGAAGCGTTCTTAAAACCTAATGATGTATTAGTTGGTGAAACA
 R  Y  F  K  Q  M  E  A  F  L  K  P  N  D  V  L  V  G  E  T

GGAACATCATATAGTGGAGCATGTAATATGAGATTCCCAGAAGGATCAAGCTTTGTAGGT
 G  T  S  Y  S  G  A  C  N  M  R  F  P  E  G  S  S  F  V  G

CAAGGATCTTGGATGTCAATTGGATATGCTACTCCTGCAGTTTTAGGAACTCATTTAGCT
 Q  G  S  W  M  S  I  G  Y  A  T  P  A  V  L  G  T  H  L  A

GATAAGAGCAGAAGAAACATTCTTTTAAGTGGTGATGGTTCATTCCAATTAACAGTTCAA
 D  K  S  R  R  N  I  L  L  S  G  D  G  S  F  Q  L  T  V  Q

GAAGTTTCAACAATGATAAGACAAAAATTAAATACAGTATTATTTGTAGTTAACAATGAT
 E  V  S  T  M  I  R  Q  K  L  N  T  V  L  F  V  V  N  N  D

GGATATACAATTGAAAGATTAATCCACGGACCTGAAAGAGAATATAACCATATTCAAATG
 G  Y  T  I  E  R  L  I  H  G  P  E  R  E  Y  N  H  I  Q  M

TGGCAATATGCAGAACTTGTAAAAACATTAGCTACTGAAAGAGATATACAACCAACTTGT
 W  Q  Y  A  E  L  V  K  T  L  A  T  E  R  D  I  Q  P  T  C

TTCAAAGTTACAACTGAAAAAGAATTAGCAGCTGCAATGGAAGAAATAAACAAAGGAACA
 F  K  V  T  T  E  K  E  L  A  A  A  M  E  E  I  N  K  G  T

GAAGGTATTGCTTTTGTTGAAGTAGTAATGGATAAAATGGATGCTCCAAAATCATTAAGA
 E  G  I  A  F  V  E  V  V  M  D  K  M  D  A  P  K  S  L  R

CAAGAAGCAAGTCTATTTAGTTCTCAAAATAACTACTAATATATATTATATATAAATAAA
 Q  E  A  S  L  F  S  S  Q  N  N  Y  *

AATTAAAAGATTGTAAATTAAATTTAAAGGTGACTTCTATTAATAGAGGTCATCTTTTT
           →   →   →   →   ←   ←   ←

ATGCTTATAAGTTTAATTTTATAAAATACAATTAGTAATTAAACACTTTATAAGAAAAAA
←
```

Fig. 9-1

```
ZpaPDC    1  ----------------------------------------------- MYTVGMYLAERLAQ
ApePDC    1  ----------------------------------------------- VTYTVGMYLAERLVQ
ZmoPDC    1  ----------------------------------------------- VSYTVGTYLAERLVQ
ZmaPDC    1  METLLAGNPANGVAKPTCNGVGALPVANSHAIIATPAAAAATLAPAGA TLGRHLARRLVQ
ScePDC1   1  ----------------------------------------------- MSEITLGKYLFERLKQ
SvePDC    1  ----------------------------------------------- VKITIAEYLLKRLKE

*  *                           *                  *  *
ZpaPDC   15  IGLKHHFAVAGDYNLVLLDQLLLNKDMEQVYCCNELNCGFSAEGYARARGAAAAIVTFSV
ApePDC   16  IGLKHHFAVGGDYNLVLLDQLLLNKDMKQIYCCNELNCGFSAEGYARSNGAAAAVVTFSV
ZmoPDC   16  IGLKHHFAVAGDYNLVLLDNLLLNKNMEQVYCCNELNCGFSAEGYARAKGAAAAVVTYSV
ZmaPDC   61  IGASDVFAVPGDFNLTLLDYLIAEPGLTLVGCCNELNAGYAADGYARSRGVGACAVTFTV
ScePDC1  17  VNVNTVFGLPGDFNLSLLDKIYEVEGMRWAGNANELNARYAADGYARIKGMSCIITTFGV
SvePDC   16  VNVEHMFGVPGDYNLGFLDYVEDSKDIEWVGSCNELNAGYAADGYARLRGFSVILTTYGV

*                           **
ZpaPDC   75  GAISAMNAIGGAYAENLPVILISGSPNTNDYGTGHILHHTIGTTDYNYQLEMVKHVTCAR
ApePDC   76  GAISAMNALGGAYAENLPVILISGAPNSNDQGTGHILHHTIGKTDYSYQLEMARQVTCAA
ZmoPDC   76  GALSAFDAIGGAYAENLPVILISGAPNNNDHAAGHVLHHALGKTDYHYQLEMAKNITAAA
ZmaPDC  121  GGLSVLNAIAGAYSENLPVVCIVGGPNSNDYGTNRILHHTIGLPDFSQELRCFQTITCYQ
ScePDC1  77  GELSALNGIAGSYAEHVGVLHVVGVPSISSQAKQLLLHHTLGNGDFTVFHRMSANISETT
SvePDC   76  GSLSAINATTGSFAENVPVLHISGVPSALVQQNRKLVHHSTARGEFDTFERMFREITEFQ

|
ZpaPDC  135  ESIVSAEEAPAKIDHVIRTALRERKPAYLEIACNVA--GAECVRPGPINSLLRELEVDQT
ApePDC  136  ESITDAHSAPAKIDHVIRTALRERKPAYLDIACNIA--SEPCVRPGPVSSLLSLPEIDHT
ZmoPDC  136  EAIYTPEEAPAKIDHVIKTALREKKPVYLEIACNIA--SMPCAAPGPASALFNLEASDEA
ZmaPDC  181  AMINNLDDAHEQIDTAIATALRESKPVYISVSCNLAGLSHPTFSRDPVPMFISPRLSNKA
ScePDC1 137  AMITDICTAPAEIDRCIRTTYVTQRPVYLGLPANIVD-LNVPAKLLQTPIDMSLKPNDAE
SvePDC  136  SIISEYN-AAEEIDRVIESIYKYQLPGYIELPVDIVS--K-EIEIDEMKPLNLTMRSNEK

|
ZpaPDC  193  SYTAAVDAAVEWLQDRQNVVMLVGSKLRAAAAEKQAVALADRLGCAVTIMAAEKGFFPED
ApePDC  194  SLKAAVDATVALLKNRPAPVMLLGSKLRAANALAATETLADKLQCAVTIMAAAKGFFPED
ZmoPDC  194  SLNAAVEETIKFIANRDKVAVLVGSKLRAAGAEEAAVKFADALGGAVATMAAAKSFFPEE
ZmaPDC  241  NLEYAVEAAADFLNKAVKPVMVGGPKIRVAKAREAFAIVADASGYPFAVMPAAKGLVPEH
ScePDC1 196  SEKEVIDTILVLAKDAKNPVILADACCSRHDVKAETKKLIDLTQFPAFVTPMGKGSISEQ
SvePDC  192  ILEKFVIDVKEMVASSKGQHILADYEVLRAKAEKELECFINEAKIPVNTLSIGKTAVSES

ZpaPDC  253  HPNFRGLYWGEVSSECAQELVENADAILCIAPVFNDYATVGWNSWPKGDNVMVMDTDRVT
ApePDC  254  HAGFRGLYWGEVSNPGVQELVETSDALLCIAPVFNDYSTVGWSGVPKGPNVILAEPDRVT
ZmoPDC  254  NPHYIGTSWGEVSYPGVEKTMKEADAVIALAPVFNDYSTTGWIDIPDPKKLVIAEPRSVV
ZmaPDC  301  HPRFIGTYWGAVSTTFCAEIVESADAYLFAGPIFNDYSSVGYSLLLKREKAVIVQPDRMV
ScePDC1 256  HPRYGGVYVGTLSKPEVKEAVESADLIILSVGALLSDFNTGSFSYSYKTKNIVEFHSDHMK
SvePDC  252  NPYFAGLFSGETSSDLVKEICKASDIVLLFGVKFIDTTTAGERYINKDVKMIEIGLTDCR
```

Fig. 9-2

```
ZpaPDC    313  EAGQSEEGLSLSTEAAALAEKAPSRP----ATTQGTQAPVLGIEAAEPNAPLTNDEMTRQ
ApePDC    314  VDGRAVDGFTLRAFLQALAEKAPARP----ASAQKSSVPTCSLTATSDEAGLTNDEIVRH
ZmoPDC    314  VNGIREPSVHLKDYLTRLAQKVSKKTGALDFFKSLNACELKKAAPADPSAPIVNAEIARQ
ZmaPDC    361  VCDGPAFGCILMPEFLRALAKRLRRNTTAYDNYRRIFVPDREPPNCKPNEPLRVNVLEKH
ScePDC1   316  IRNATEPGVQMKFVLQKLLTNIADAAKG--YKPVAVPARTPANAAVPASTPLKQEWMWNQ
SvePDC    312  IGETIYTGLYLKDVLKALTDAKIKFHN------DVKVEREAVEKFVPTIAKLTQDRYEKQ

**                    * *
ZpaPDC    369  IQSLLTSDTTILTAETGDSWFNASRMPLPGGARVELEMQWGHIGWSVPSAEGNAVGSPER-
ApePDC    370  INALLTSNTTLVAETGDSWFNAMRMTLAG-ARVELEMQWGHIGWSVPSAEGNAMGSQDR-
ZmoPDC    374  VEALLTPNTTVIAETGDSWFNAQRMKLPNGARVEYEMQWGHIGWSVPAAFGYAVGAPER-
ZmaPDC    421  IKCMLSGDSAVVAETGDSWFNCQKLRLPEGCGYEFQMQYGSIGWSVGATIGYAQAAKDK-
ScePDC1   374  EGNELQEGDVVIAETGTSAFGIAQTTFPNNTYGISQVLWGSIGFTGATICAAFAAEEID
SvePDC    366  VEAFLKPNDVLVGETGTSYSGACNMRFPEGSSFVGQGSWMSIGYATPAVLGTHLADKSR-

** *                  * * *  **
ZpaPDC    428  ---RHIMMVGDGSFQLTAQEVAQMIRYELPVIIFLINNRGVVIELAIH--DGPYNYIKNW
ApePDC    428  ---QHVVMVGDGSFQLTAQEVAQMVRYELPVIIFLINNRGVVIELAIH--DGPYNYIKNW
ZmoPDC    433  ---RNILMVGDGSFQLTAQEVAQMVRLKLPVIIFLINNYGYTIEVMIH--DGPYNNIKNW
ZmaPDC    480  ---RVIACIGDGSFQVTAQDVSTMLRCGQKSIIFLINNGGYTIEVEIH--DGPYNVIKNW
ScePDC1   434  PKKRVILFIGDGSLQLTVQEISTMIRWGLKPYLFVLNNDGYTIEKLIHGPKAQYNEIQGW
SvePDC    425  ---RNILLSGDGSFQLTVQEVSTMIRQKLNTVLFVVNNDGYTIERLIHGPEREYNHIQMW

ZpaPDC    483  NYAGLIDVFND----EDGHGLGLKASTGAELEGAIKKAL-DNRRGPTLIECNIAQDDCTE
ApePDC    483  DYAGLMEVFNA----GEGHGLGLKAITPKEITEAIARAK-ANTRGPTLIECQIDRTDCTD
ZmoPDC    488  DYAGLMEVFNCNGGYDSGAGKGLKAKTGGEIAEAIKVAL-ANTDGPTLIECFIGREDCTE
ZmaPDC    535  DYTGLVNAIHN----SLGNCWTMKVRTEEQIKEAIATVTGAKKDCLCFIEVIVHKDDTSK
ScePDC1   494  DHLSLLPTEGAK---D---YETHRVATTGEWDKLTQDKSFNCNSKIRMIEVMLPVFDAPQ
SvePDC    482  QYAELVKTLATER---DIQPTCEKVTTEKELAAAMEEIN-KGTEGIAFVEVVVDKMDAPK

ZpaPDC    538  TLIAWGKRVAATNSRKEQA---
ApePDC    538  MLVQWGRKVASTNARKTTLA--
ZmoPDC    547  ELVKWGKRVAAANSRKPVNKLL
ZmaPDC    591  ELLEWGSRVSAANSRPENPQ--
ScePDC1   548  NLVEQAKLTAATNAKQ------
SvePDC    538  SLRQEASLFSSQNNY-------
```

CLONING AND SEQUENCING OF PYRUVATE DECARBOXYLASE (PDC) GENES FROM BACTERIA AND USES THEREFOR

RELATED INFORMATION

This application claims priority to U.S. provisional application No. 60/288,638, entitled "High-Level Production of Active *Sarcina ventriculi* Pyruvate Decarboxylase in Recombinant *Bacillus megaterium*"; U.S. provisional application No. 60/288,671, entitled "Cloning, Expression, and Characterization of Pyruvate Decarboxylase from the Acid-Tolerant, Anaerobic Gram-Positive Bacterium *Sarcina ventriculi* Goodsir"; U.S. provisional application No. 60/288, 698, entitled "*Acetobacter pasteurianus* Pyruvate Decarboxylase: Biochemical, Genetic, and Physiological Properties"; U.S. provisional application No. 60/288,622, entitled "Biochemical and Biophysical Characterization of Pyruvate Decarboxylase from the Acetic Acid Bacterium *Acetobacter pasteurianus*"; and U.S. provisional application No. 60/288,699, entitled "Pyruvate Decarboxylase: A Key Enzyme for the Oxidative Metabolism of Lactic Acid by *Acetobacter pasteurianus*"; all of which were filed on May 4, 2001 and are incorporated herein in their entireties by this reference. The contents of all patents, patent applications, and references cited throughout this specification are hereby incorporated by reference in their entireties.

GOVERNMENT SPONSORED RESEARCH

This work was supported, in part, by grants from the U.S. Department of Energy's National Renewable Energy Laboratory (ZDH-9-29009-04), Energy Biosciences Program (FG02-96ER20222), and the Florida Agricultural Experiment Station. The Government has certain rights in the invention.

BACKGROUND OF THE INVENTION

Many environmental and societal benefits would result from the replacement of petroleum-based automotive fuels with renewable fuels obtained from plant materials (Lynd et al., (1991) *Science* 251:1318-1323; Olson et al., (1996) *Enzyme Microb. Technol.* 18:1-17; Wyman et al., (1995) *Amer. Chem. Soc. Symp.* 618:272-290). Each year, the United States burns over 120 billion gallons of automotive fuel, roughly equivalent to the total amount of imported petroleum. The development of ethanol as a renewable alternative fuel has the potential to eliminate United States dependence on imported oil, improve the environment, and provide new employment (Sheehan, (1994) ACS Symposium Series No. 566, ACS Press, pp 1-53).

In theory, the solution to the problem of imported oil for automotive fuel appears quite simple. Rather than using petroleum, a finite resource, ethanol, a renewable resource, can be produced efficiently by the fermentation of plant material. Indeed, Brazil has demonstrated the feasibility of producing ethanol and the use of ethanol as a primary automotive fuel for more than 20 years. Similarly, the United States produces over 1.2 billion gallons of fuel ethanol each year. Currently, fuel ethanol is produced from corn starch or cane syrup utilizing either *Saccharomyces cerevisiae* or *Zymomonas mobilis* (*Z. mobilis*). However, neither of these sugar sources can supply the volumes needed to realize a replacement of petroleum-based automotive fuels. In addition, both cane sugar and corn starch are relatively expensive starting materials, which have competing uses as food products.

Moreover, these sugar substrates represent only a fraction of the total carbohydrates in plants. Indeed, the majority of the carbohydrates in plants are in the form of lignocellulose, a complex structural polymer containing cellulose, hemicellulose, pectin, and lignin. Lignocellulose is found in, for example, the stems, leaves, hulls, husks, and cobs of plants. Hydrolysis of these polymers releases a mixture of neutral sugars including glucose, xylose, mannose, galactose, and arabinose. No known natural organism can rapidly and efficiently metabolize all of these sugars into ethanol.

Nonetheless, in an effort to exploit this substrate source, the Gulf Oil Company developed a method for the production of ethanol from cellulose using a yeast-based process termed simultaneous saccharification and fermentation (SSF) (Gauss et al. (1976) U.S. Pat. No. 3,990,944). Fungal cellulase preparations and yeasts were added to a slurry of the cellulosic substrate in a single vessel. Ethanol was produced concurrently during cellulose hydrolysis. However, Gulf's SSF process has some shortcomings. For example, the cell cycle time for yeast is relatively long (24-36 hours) and they are unable to ferment complex sugars. Further, fungal cellulases have to be added which have been considered, thus far, to be too expensive for use in large scale bioethanol processes (Himmel et al., (1997) Amer. Chem. Soc. pp. 2-45; Ingram et al., (1987) *Appl. Environ. Microbiol.* 53:2420-2425; Okamoto et al., (1994) *Appl. Microbiol. Biotechnol.* 42:563-568; Philippidis, G., (1994) Amer. Chem. Soc. pp. 188-217; Saito et al., (1990) *J. Ferment. Bioeng.* 69:282-286; Sheehan, J., (1994) Amer. Chem. Soc. pp 1-52; Su et al., (1993) *Biotechnol. Lett.* 15:979-984).

Moreover, producing ethanol using other organisms is difficult because pyruvate decarboxylase (PDC), a key enzyme for fermenting ethanol, is common only to plants, yeast, and fungi; and is rarely found in bacteria and is absent in animals (9, 25).

SUMMARY OF THE INVENTION

The development of inexpensive enzymatic methods for ethanol fermentation has great potential for improving the efficiency of substrate utilization and the economics of the fermentation process. Accordingly, developing enzymes and, advantageously, biocatalysts that produce such enzymes which can be used for the efficient depolymerization of complex sugars and subsequent rapid fermentation of the sugar into alcohol, would be of great benefit.

Certain microbes, such as Gram-negative and Gram-positive bacteria produce a number of fermentation enzymes, which are capable of catalyzing, for example, the depolymerization of cellulose and hemicellulose to produce fermentable sugars, conversion of a sugar into pyruvate, the substrate pyruvate into acetaldehyde, and finally, the substrate acetaldehyde into ethanol. However, such organisms rarely produce all of the necessarily enzymes at the most desirable levels.

Accordingly, the invention provides genes encoding pyruvate decarboxylases which can be expressed at high levels in a range of organisms. Thus, when expressed in an organism, or cultured with an organism, that produces the remaining key enzymes needed for ethanol fermentation, superior levels of ethanol production can be achieved. These enzymes, for example pyruvate decarboxylase (PDC), alone or in combination with alcohol dehydrogenase (ADH), can be used as a crude extract having a desired mixture of activity or, can be used as a purified composition.

Moreover, a biocatalyst, advantageously a recombinant bacterium, more advantageously a ethanologenic bacterium, can be engineered to express one or more of these enzymatic activities in particular amounts sufficient for fermenting a sugar(s). Such a biocatalyst is suitable for the efficient degradation of complex sugars and subsequent fermentation into alcohol by a process known as simultaneous saccharification and fermentation (SSF).

The present invention is based, at least in part, on the discovery of key enzyme-encoding genes of ethanol fermentation in bacteria. In particular, the identification of the pdc gene of *Zymobacter palmae, Acetobacter pasteurianus*, and *Sarcina ventriculi* has been achieved. These genes have been determined to encode pyruvate decarboxylase enzymes having superior pyruvate decarboxylase activity, substrate affinity, for, e.g., pyruvate, as well as thermostability, and superior activity at different pH. Still further, the pdc genes of the invention have a codon usage that affords for their high expression in a range of organisms.

Accordingly, in one aspect, the invention provides isolated nucleic acid molecules encoding pyruvate decarboxylase polypeptides (PDC) or biologically active portions thereof, as well as nucleic acid fragments suitable as primers or hybridization probes for the detection of PDC-encoding nucleic acids.

In one embodiment, an pyruvate decarboxylase (pdc) nucleic acid molecule of the invention is at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identical to the nucleotide sequence (e.g., when compared to the overall length of the nucleotide sequence) shown in SEQ ID NO:1, 3, 5, or a complement thereof.

In a particular embodiment, the isolated nucleic acid molecule includes the nucleotide sequence shown in SEQ ID NO:1, 3, 5, or a complement thereof.

In another embodiment, a pdc nucleic acid molecule includes a nucleic acid sequence encoding a polypeptide having an amino acid sequence sufficiently homologous to the amino acid sequence of SEQ ID NO:2, 4, or 6. In a particular embodiment, a pdc nucleic acid molecule includes a nucleotide sequence encoding a (PDC) polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to the amino acid sequence shown in SEQ ID NO:2, 4, or 6.

In one particular embodiment, an isolated nucleic acid molecule encodes the amino acid sequence of the pyruvate decarboxylase enzyme of *Zymobacter palmae* having the amino acid sequence of SEQ ID NO:2.

In another particular embodiment, an isolated nucleic acid molecule encodes the amino acid sequence of the pyruvate decarboxylase enzyme of *Acetobacter pasteurianus* having the amino acid sequence of SEQ ID NO:4.

In yet another particular embodiment, an isolated nucleic acid molecule encodes the amino acid sequence of the pyruvate decarboxylase enzyme of *Sarcina ventriculi* having the amino acid sequence of SEQ ID NO:6.

In another particular embodiment, the nucleic acid molecule is at least about 1600 nucleotides in length and encodes a polypeptide having pyruvate decarboxylase activity (as described herein).

In a more particular embodiment, the invention provides a plasmid, pJAM3440, encoding a pdc gene derived from *Zymobacter palmae* represented by a deposit with the American Type Culture Collection designated as deposit number ATCC PTA-4254. In a related embodiment, the invention provides a plasinid, pJAM304, encoding a pdc gene derived from *Acetobacter pasteurianus* represented by a deposit with the American Type Culture Collection designated as deposit number ATCC PTA-4252. In another related embodiment, the invention provides a plasmid, pJAM419, encoding a pdc gene derived from *Sarcina ventriculi* represented by a deposit with the American Type Culture Collection designated as deposit number ATCC PTA-4253.

Another embodiment of the invention features nucleic acid molecules, advantageously pyruvate decarboxylase nucleic acid molecules, which specifically detect pyruvate decarboxylase nucleic acid molecules (i.e., pdc gene(s)) relative to nucleic acid molecules encoding non-pyruvate decarboxylase (PDC) polypeptides. For example, in one embodiment, such a nucleic acid molecule is at least 50, 60, 70, 80, 90, 100, 150, 200, 300, 400, 500, 500-1000, 1000-1500, 1500-2000 or more nucleotides in length and/or hybridizes under stringent conditions to a nucleic acid molecule comprising the nueleotide sequence shown in SEQ ID NO: 1, 3, or 5,or a complement thereof. It should be understood that the nucleic acid molecule can be of a length within a range having one of the numbers listed above as a lower limit and another number as the upper limit for the number of nucleotides in length, e.g., moiccules that are 60-80, 300-1000, or 150-400 nucleotides in length.

In particular embodiments, the nucleic acid molecules are at least 15 (e.g., contiguous) nucleotides in length and hybridize under stringent conditions to the nucleotide sequence of SEQ ID NO:1, 3, or 5. Accordingly, the invention provides a method for detecting the presence of a pdc nucleic acid of the invention using the foregoing nucleic acid.

In other particular embodiments, the nucleic acid molecule encodes a naturally occurring allelic variant of a polypeptide comprising the amino acid sequence of SEQ ID NO:2, 4, or 6, wherein the nucleic acid molecule hybridizes to a nucleic acid molecule comprising SEQ ID NO:1, 3, or 5, respectively, under stringent conditions.

In another embodiment, the nucleic acid molecule of the invention is in a vector and may be optionally linked to a surrogate promoter and/or additional nucleic acid sequences encoding a heterologous polypeptide.

In a particular embodiment, the invention provides a host cell containing a nucleic acid molecule of the invention, for example, contained in a vector or stably integrated into the host cell genome.

In one particular embodiment, the host cell comprises a heterologous nucleic acid sequence encoding pyruvate decarboxylase derived from a bacterial cell such as *Zymobacter palmae, Acetobacter pasteurianus*, or *Sarcina ventriculi*, for example, as provided, in SEQ ID NO:1, SEQ ID NO:3, or SEQ ID NO:5.

In another embodiment, the host cell containing a pdc gene can be ethanologenic, for example, naturally ethanologenic and/or further comprise an ethanologenic gene(s) encoding alcohol dehydrogenase, glucanase, secretase, or a combination thereof. In a related embodiment, the host cell is suitable for fermenting ethanol from a sugar. In a particular embodiment, the host cell is a recombinant ethanologenic host cell comprising a heterologous nucleic acid encoding a PDC shown in SEQ ID NO:2, SEQ ID NO:4, or SEQ ID NO:6. The heterologous nucleic acid can be under the control of exogenous surrogate promoter.

The aforementioned host cell can be a Gram-negative bacterial cell or a Gram-positive bacterial cell.

A Gram-negative host cell of the invention can be, e.g., *Gluconobacter, Rhizobium, Bradyrhizobium, Alcaligenes, Rhodobacter, Rhodococcus. Azospirillum, Rhodospirillum, Sphingomonas, Burkholderia, Desuifomonas, Geospirillum, Succinomonas, Aeromonas, Shewanella, Halochromatium, Citrobacter, Escherichia, Klebsiella, Zymomonas Zymobacter*, or *Acetobacter*.

A Gram-positive host cell of the invention can be, e.g., *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, or *Sarcina*.

In another aspect, the invention provides an isolated polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to the amino acid sequence shown in SEQ ID NO:2, 4, or 6.

In one embodiment, the isolated polypeptide of the invention has the amino acid sequence of SEQ ID NO:2, 4, or 6.

In a related embodiment, the isolated polypeptide has pyruvate decarboxylase activity. The pyruvate decarboxylase of the invention can be selected for improved activity, e.g., pyruvate decarboxylase activity, but also, for example, improved codon usage, substrate (e.g., pyruvate) affinity, thermal stability, and/or activity at a certain pH. Such a pyruvate decarboxylase of the invention can be an altered or chimeric polypeptide to achieve any of the aforementioned properties. In addition, the polypeptide can further comprises heterologous amino acids, for example, an immunotag for purification or detection.

In another aspect, the invention provides an antibody which selectively binds to a polypeptide of invention (or fragment thereof), for example, a pyruvate decarboxylase enzyme as shown, for example, in SEQ ID NO:2, 4, or 6. Accordingly, the invention provides a method for detecting a pyruvate decarboxylase of the invention using such an antibody.

In another aspect, the invention provides a method for producing a pyruvate decarboxylase of the invention by expressing in a host cell one of the foregoing nucleic acids of the invention under suitable culture conditions. The nucleic acid may be altered or mutated to improve the codon usage of the nucleic acid or decarboxylase activity of the encoded product (e.g., thermal stability, substrate affinity, or activity at various pH).

In another aspect, the invention provides a method for producing acetaldehyde by culturing one of the aforementioned hosts under conditions whereby pyruvate decarboxylase is expressed at sufficient levels such that acetaldehyde is produced from pyruvate. In a related embodiment, the method for producing acetaldehyde is performed by contacting a cell lysate obtained from the above host cell under conditions whereby acetaldehyde is produced from pyruvate. Accordingly, the invention provides enzyme extracts having improved decarboxylase activity, and having, for example, thermal stability, activity at various pH, and/or superior substrate affinity.

In another aspect, the invention provides a method for producing ethanol by culturing the above host cell under conditions whereby pyruvate decarboxylase and alcohol dehydrogenase are expressed at sufficient levels such that ethanol is produced as a primary fermentation product.

In another as aspect, the invention provides a method for selecting a pyruvate decarboxylase enzyme with improved decarboxylase activity (e.g., improved affinity for pyruvate, thermal stability, activity at different pH) by comparing the amino acid sequence of a pyruvate decarboxylase with the amino acid sequence of SEQ ID NO:2, SEQ ID NO:4, or SEQ ID NO:6; and altering at least one amino acid residue of the pyruvate decarboxylase to have identity with the corresponding amino acid residue of SEQ ID NO:2, SEQ ID NO:4, or SEQ ID NO:6, such that a polypeptide with improved pyruvate decarboxylase activity is achieved.

In a related embodiment, the invention provides a method for selecting a pyruvate decarboxylase enzyme for expression in a recipient host cell by comparing the nucleic acid sequence encoding a pyruvate decarboxylase with the nucleic acid sequence of SEQ ID NO:1, SEQ ID NO:3, or SEQ ID NO:5; and altering at least one codon of the nucleic acid encoding the pyruvate decarboxylase enzyme to have identity with the corresponding codon of SEQ ID NO:1, SEQ ID NO:3, or SEQ ID NO:5, such that improved expression of the altered nucleic acid encoding pyruvate decarboxylase enzyme is achieved in the host cell.

In another related embodiment, the invention provides a method for selecting a pyruvate decarboxylase enzyme with improved expression in a recipient host cell by comparing the nucleic acid sequence encoding a pyruvate decarboxylase with the codon usage of the recipient host cell and altering at least one codon of the nucleic acid encoding the pyruvate decarboxylase enzyme to correspond with the codon usage of the recipient host cell such that improved expression of the altered nucleic acid encoding pyruvate decarboxylase enzyme is achieved in the host cell.

In yet another related embodiment, the invention provides a method for selecting a pyruvate decarboxylase enzyme with improved expression in a recipient host cell by comparing the nucleic acid sequence encoding a pyruvate decarboxylase with the codon usage of the recipient host cell and altering the recipient host cell to recombinantly produce at least one tRNA corresponding to a codon of the nucleic acid encoding the pyruvate decarboxylase enzyme such that improved expression of the nucleic acid encoding pyruvate decarboxylase enzyme is achieved in the altered host cell.

Other features and advantages of the invention will be apparent from the following detailed description and claims.

BRIEF DESCRIPTION OF THE DRAWINGS

FIG. 4 shows the nucleic acid sequence (SEQ ID NO:1) and amino acid sequence (SEQ ID NO:2) for the pdc gene and gene product of *Zymobacter palmae*.

FIG. 5 shows the nucleic acid sequence (SEQ ID NO:3) and amino acid sequence (SEQ ID NO:4) for the pdc gene and gene product of *Acetobacter pasteurianus*. A putative promoter is double underlined with the −35 and −10 promoter consensus sequence indicated directly below the sequence predicted for PDC and highlighted by capital letters in the nucleic acid sequence of pdc. Arrowheads above the DNA sequence indicate transcription start sites. Underlined bases indicate a "Shine-Dalgarno" ribosome binding-site. An asterisk indicates translation stop codon. Arrows below the DNA sequence indicate a stem-loop structure, which can facilitate ρ-independent transcription termination.

FIG. 6 shows the nucleic acid sequence (SEQ ID NO:5) and amino acid sequence (SEQ ID NO:6) for the pdc gene and gene product of *Sarcina ventriculi*.

FIG. 9 shows a multiple amino acid sequence alignment of the deduced PDC polypeptide of *Z. palmae* (SEQ ID NO:2) aligned with selected PDC polypeptides, i.e., *Z. mobilis* (SEQ ID NO:8), *A. pasteurianus* (SEQ ID NO:4), *S. ventriculi* (SEQ ID NO:6), *Z mays* (SEQ ID NO:9), and *S. cerevisiae* (SEQ ID NO:10). Functionally conserved (black highlight) and semi-conserved (gray highlight) amino acid residues. Gaps introduced in alignment (--). Residues within 0.4 nm of the $Mg^{2+}$ and TPP binding sites of the yeast and *Z. mobilis* PDC polypeptides (*). Yeast PDC1 residues forming hydrogen bonds with pyruvamide (■). Double underlined residues are conserved among TPP-dependent enzymes. Abbreviation and GenBank or SwissProt accession number: Zpa, *Z. palmae*, AF474145; Apa, *A. pasteurianus*, AR368435; Sce, *Saccharomyces cerevisiae*, P06169; Sve, *Sarcina ventriculi*, AF354297; Zma, *Zea mays*, P28516; Zmo, *Zymomonas mobilis*, P06672.

DETAILED DESCRIPTION OF THE INVENTION

Figure 1:
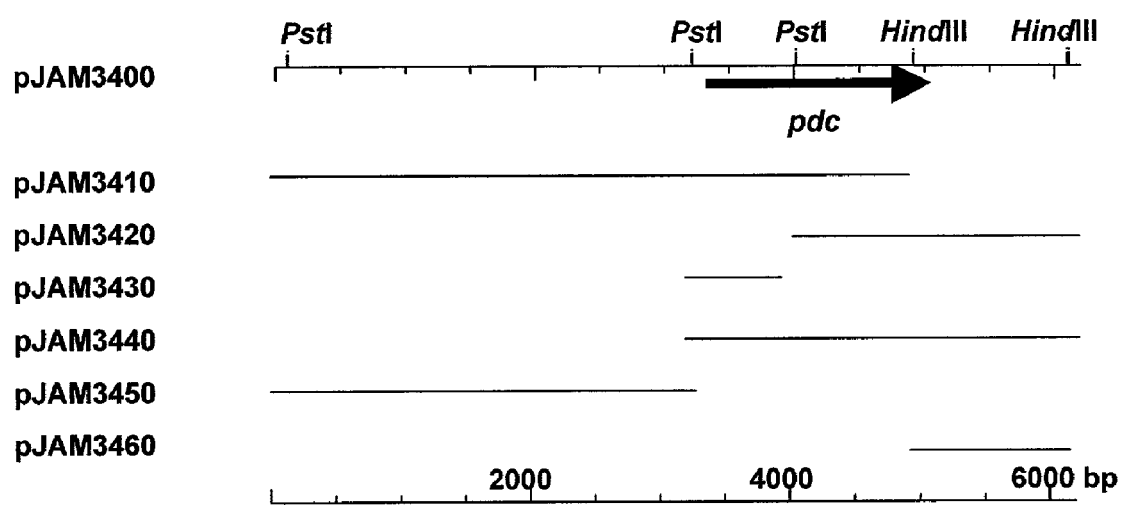
FIG. 1 shows a schematic representation of the *Zymobacter palmae* pdc gene. Plasmid pJAM3400 carries a 6-kb BamHI fragment of *Z. palmae* genomic DNA blunt-ended and ligated into plasmid vector pLITMUS28. The remaining plasmids were derived from pJAM3400 and were used for DNA sequence analysis of a 2.9-kb region that included the pdc gene. Plasmid pJAM3440 was used to produce the *Z. palmae* PDC polypeptide in recombinant *E. coli*. The arrowhead indicates the direction of pdc gene transcription.

In order for the full scope of the invention to be clearly understood, the following definitions are provided.

I. Definitions

As used herein the term "alcohol dehydrogenase" is intended to include the enzyme capable of converting acetaldehyde into an alcohol, advantageously, ethanol.

The term "chimeric" includes a mutant or altered PDC where an entire domain derived from another PDC is engineered (fused, exchanged) with a corresponding domain in a PDC, using, e.g., genetic engineering.

The term "codon usage" is intended to include analyzing a given nucleic acid being considered for expression in a recipient host organism (or acellular extract thereof) for the occurrence or "usage" of certain codons that the host organism will require (advantageously at sufficient levels) in order to translate the nucleic acid into a corresponding polypeptide. Based on such observations the recipient host may be recombinantly supplemented with any necessary codon. Alternatively, another host can be selected with superior codon usage or the nucleic acid can be altered to no longer comprise a limiting codon (e.g., by introducing a silent mutation(s)).

The term "decarboxylase activity" is intended to include the ability of a polypeptide to enzymatically convert pyruvate into acetaldehyde. Typically, the activity of a selected polypeptide encompasses the total enzymatic activity associated with the produced polypeptide, comprising, e.g., the superior substrate affinity of the enzyme, thermostability, stability at different pHs, or a combination of these attributes.

The term "derived from" is intended to include the isolation (in whole or in part) of a polynucleotide segment from an indicated source. The term is intended to include, for example, direct cloning, PCR amplification, or artificial synthesis from, or based on, a sequence associated with the indicated polynucleotide source.

The term "ethanologenic" is intended to include the ability of a microorganism to produce ethanol from a carbohydrate as a primary fermentation product. The term is intended to include naturally occurring ethanologenic organisms, ethanologenic organisms with naturally occurring or induced mutations, and ethanologenic organisms which have been genetically modified.

The terms "fermenting" and "fermentation" are intended to include the enzymatic process (e.g., cellular or acellular, e.g., a lysate or purified polypeptide mixture) by which ethanol is produced from a carbohydrate, in particular, as a primary product of fermentation.

The term "gene involved in ethanologenesis" is intended to include any gene capable of conferring on a cell ethanologenic properties or capable of improving any aspect of cellular ethanologenesis, such as, e.g., substrate uptake, substrate processing, ethanol tolerance, etc. Genes involved in ethanologenesis are, e.g., alcohol dehydrogenase, pyruvate decarboxylase, secretory polypeptide/s, and polysaccharases, and these genes, or their homologs, can be derived from any appropriate organism.

The term "glucanase" is intended to include a polypeptide capable of catalyzing the degradation or depolymerization of any linked sugar moiety, e.g., disaccharides, trisaccharides, oligosaccharides, including, complex carbohydrates, also referred to herein as complex sugars, e.g., cellooligosaccharide and lignocellulose, which comprises cellulose, hemicellulose, and pectin. The terms are intended to include cellulases such as glucanases, including advantageously, endoglucanases but also including, e.g., exoglucanase, β-glucosidase, cellobiohydrolase, endo-1,4-β-xylanase, β-xylosidase, α-glucuronidase, α-L-arabinofuranosidase, acetylesterase, acetylxylanesterase, α-amylase, β-amylase, glucoamylase, pullulanase, β-glucanase, hemicellulase, arabinosidase, mannanase, pectin hydrolase, pectate lyase, or a combination of any of these cellulases.

The term "Gram-negative bacterial cell" is intended to include the art recognized definition of this term. Typically, Gram-negative bacteria include *Gluconobacter, Rhizobium, Bradyrhizobium, Alcaligenes, Rhodobacter, Rhodococcus. Azospirillum, Rhodospirillum, Sphingomonas, Burkholderia, Desuifomonas, Geospirillum, Succinomonas, Aeromonas, Shewanella, Halochromatium, Citrobacter, Escherichia, Klebsiella, Zymomonas* (e.g., *Zymomonas mobilis*), *Zymobacter* (e.g., *Zymobacter palmae*), and *Acetobacter* (e.g., *Acetobacter pasteurianus*).

The term "Gram-positive bacteria" is intended to include the art recognized definition of this term. Typically, Gram-positive bacteria include *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Sarcina* (e.g. *Sarcina ventriculi*).

The term "heterologous polypeptide" is intended to include a polypeptide or portion thereof that can be encoded by a heterologous nucleic acid derived from any source, e.g., eukaryotes, prokaryotes, virii, or synthetic nucleic acid fragments.

The term "homologous" is intended to include a first amino acid or nucleotide sequence which contains a sufficient or minimum number of identical or equivalent amino acid residues or nucleotides, e.g., an amino acid residue which has a similar side chain, to a second amino acid or nucleotide sequence such that the first and second amino acid or nucleotide sequences share common structural domains and/or a common functional activity.

The terms "host cell" and "recombinant host cell" are intended to include a cell suitable for genetic manipulation, e.g., which can incorporate heterologous polynucleotide sequences, e.g., which can be transfected. The cell can be a microorganism or a higher eukaryotic cell, such as an animal cell or a plant cell. The term is intended to include progeny of the cell originally transfected. In particular embodiments, the cell is a bacterial cell, e.g., a Gram-negative bacterial cell or a Gram-positive cell. Particularly, the term recombinant host cell is intended to include a cell that has already been selected or engineered to have certain desirable properties and suitable for further modification using the compositions and methods of the invention.

The term an "isolated polypeptide" (e.g., an isolated or purified biosynthetic enzyme) is substantially free of cellular material or other contaminating polypeptides from the microorganism from which the polypeptide is derived, or substantially free from chemical precursors or other chemicals when chemically synthesized.

The term "nucleic acid" is intended to include nucleic acid molecules, e.g., polynucleotides which include an open reading frame encoding a polypeptide, and can further include non-coding regulatory sequences, and introns. In addition, the terms are intended to include one or more genes that map to a functional locus. In addition, the terms are intended to include a specific gene for a selected purpose. The gene can be endogenous to the host cell or can be recombinantly introduced into the host cell, e.g., as a plasmid maintained episomally or a plasmid (or fragment thereof) that is stably integrated into the genome. In one embodiment, the gene of polynucleotide segment is involved in at least one step in the bioconversion of a carbohydrate to ethanol. Accordingly, the term is intended to include any gene encoding a polypeptide such as a pyruvate decarboxylase, an alcohol dehydrogenase, a secretory polypeptide/s, or a polysaccharase, e.g., a glucanase, or a combination thereof.

The phrase "mutant nucleic acid molecule" or "mutant gene" is intended to include a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene.

The phrase "operably linked" means that the nucleotide sequence of the nucleic acid molecule or gene of interest is linked to the regulatory sequence(s) in a manner which allows for expression (e.g., enhanced, increased, constitutive, basal, attenuated, decreased or repressed expression) of the nucleotide sequence, advantageously expression of a gene product encoded by the nucleotide sequence (e.g., when the recombinant nucleic acid molecule is included in a recombinant vector, as defined herein, and is introduced into a microorganism).

The term "pH" is intended to include its art recognized meaning. Typically, the pyruvate decarboxylase enzymes of the invention exhibit decarboxylase activity at a pH of about 4 to about 8, more particularly at a pH of about 5 to about 7, even more particularly at a pH of about 5.5 to about 6.0.

The term "pyruvate decarboxylase" is intended to include the enzyme described herein capable of decarboxylating pyruvate into acetaldehyde. By convention, the term "pdc" refers to a pyruvate decarboxylase gene whereas the term "PDC" refers to a pdc gene product, i.e., a pyruvate decarboxylase polypeptide or enzyme.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). Advantageously, a recombinant nucleic acid molecule (e.g., a recombinant DNA molecule) includes an isolated nucleic acid molecule or gene of the present invention (e.g., an isolated pdc gene) operably linked to regulatory sequences.

The term "secretase" is intended to include any polypeptide/s, alone or in combination with other polypeptides, that facilitate the transport of another polypeptide from the intracellular space of a cell to the extracellular milieu. In one embodiment, the secretory polypeptidels encompass all the necessary secretory polypeptides sufficient to impart secretory activity to a Gram-negative or Gram-positive host cell.

The term "simultaneous saccharification and fermentation" or "SSF" is intended to include the use of one or more recombinant hosts (or extracts thereof, including purified or unpurified extracts, and if desired, other enzyme additions, e.g., from one or more different sources) for the contemporaneous degradation or depolymerization of a complex sugar and bioconversion of that sugar residue into acetaldehyde and subsequently, if desired, into ethanol by fermentation.

The term "substrate affinity" is intended to include the binding kinetics of an enzyme for a substrate, for example, the $K_M$ of the enzyme pyruvate decarboxylase for its substrate pyruvate (or analog thereof). Typically, the pyruvate decarboxylase enzymes of the invention exhibit a substrate affinity (e.g., for pyruvate) having a $K_M$ of about 0.1 to about 1, more particularly a $K_M$ of about 0.1 to about 0.5, even more particularly a $K_M$ of about 0.2 to about of about 0.4.

The term "sugar" is intended to include any carbohydrate source comprising a sugar molecule(s). Such sugars are potential sources of sugars for depolymerization (if required) and subsequent bioconversion to acetaldehyde and subsequently to ethanol by fermentation according to the products and methods of the present invention.

The term "surrogate promoter" is intended to include a polynucleotide segment that can transcriptionally control a gene-of-interest, e.g., a pyruvate decarboxylase gene, that it does not transcriptionally control in nature. In one embodiment, the transcriptional control of a surrogate promoter results in an increase in expression of the gene-of-interest. In another embodiment, a surrogate promoter is placed 5' to the gene-of-interest. A surrogate promoter can be used to replace the natural promoter, or can be used in addition to the natural promoter. A surrogate promoter can be endogenous with regard to the host cell in which it is used or it can be a heterologous polynucleotide sequence introduced into the host cell, e.g., exogenous with regard to the host cell in which it is used. Other promoters suitable for use in bacteria include, e.g., lacZ, T7, and SP6 (see, e.g., Ausubel et al. infra).

The terms "thermal stability" and "thermostability" are used interchangeably and are intended to include the ability of a enzyme (e.g., whether expressed in a cell, present in an cellular extract, cell lysate, or in purified or partially purified form) to exhibit the ability to catalyze a reaction (e.g., the conversion of pyruvate to acetaldehyde) at least at about 20° C., advantageously at about 25° C. to 35° C., more advantageously at about 37° C. or higher, in particular, at about 50° C. or higher, for example, at least about 60° C. or higher.

II Isolated Nucleic Acid Molecules and Genes

The present invention features nucleic acid molecules comprising pyruvate decarboxylase genes (pdc) that encode pyruvate decarboxylase polypeptide enzymes (PDC) wherein the nucleic acids have been isolated from Gram-negative and Gram-positive bacteria, for example, the Gram-negative bacteria *Zymobacter palmae, Acetobacter pasteurianus* and from the Gram-positive bacterium *Sarcina ventriculi*. Also featured are isolated genomic nucleic acids comprising any one of the above mentioned pyruvate decarboxylase genes (i.e., pdc) but also other flanking regions which comprise regulatory regions (e.g., promoter(s) and ribosome binding sites(s)) as well as other associated genes involved in ethanologenesis, e.g., alcohol dehydrogenase (adh)).

The nucleic acid molecule includes DNA molecules (e.g., linear, circular, cDNA or chromosomal DNA) and RNA molecules (e.g., tRNA, rRNA, mRNA) and analogs of the DNA or RNA generated using nucleotide analogs. The nucleic acid molecule can be single-stranded or double-stranded, but advantageously is double-stranded DNA. The isolated nucleic acid molecule of the invention includes a nucleic acid molecule which is free of sequences which naturally flank the nucleic acid molecule (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 bp or 10 bp of nucleotide sequences which naturally flank the nucleic acid molecule in chromosomal DNA of the microorganism from which the nucleic acid molecule is derived. Moreover, an "isolated" nucleic acid molecule, such as a cDNA molecule, can be substantially free of other cellular materials when produced by recombinant techniques, or substantially free of chemical precursors or other chemicals when chemically synthesized.

The pdc genes, as described herein (and italicized by convention), include a nucleic acid molecule (e.g., a DNA molecule or segment thereof), for example, a polypeptide or RNA-encoding nucleic acid molecule that, in an organism, is separated from another gene or other genes, by intergenic DNA (i.e., intervening or spacer DNA which naturally flanks the gene and/or separates genes in the chromosomal DNA of the organism). A gene can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered in an operon, as defined herein, wherein the operon is separated from other genes and/or operons by intergenic DNA. Individual genes contained within an operon can overlap without intergenic DNA between the individual genes.

An isolated gene as described herein, includes a gene which is essentially free of sequences which naturally flank the gene in the chromosomal DNA of the organism from which the gene is derived (i.e., is free of adjacent coding sequences which encode a second or distinct polypeptide or RNA molecule, adjacent structural sequences or the like) and optionally includes 5' and 3' regulatory sequences, for example promoter sequences and/or terminator sequences. In one embodiment, an isolated gene includes predominantly coding sequences for a polypeptide (e.g., sequences which encode PDC polypeptides).

In another embodiment, an isolated gene includes coding sequences for a polypeptide (e.g., for a PDC polypeptide) and adjacent 5' and/or 3' regulatory sequences from the chromosomal DNA of the organism from which the gene is derived (e.g., adjacent 5' and/or 3' pdc regulatory sequences). Advantageously, an isolated gene contains less than about 10 kb, 5 kb, 2 kb, 1 kb, 0.5 kb, 0.2 kb, 0.1 kb, 50 bp, 25 bp or 10 bp of nucleotide sequences which naturally flank the gene in the chromosomal DNA of the organism from which the gene is derived.

In one aspect, the present invention features isolated pdc nucleic acid sequences or genes, isolated alcohol dehydrogenase (adh) nucleic acid sequences or genes advantageously derived from a Gram-positive or Gram-negative bacteria. Advantageously, the pdc nucleic acid or gene is derived from a Gram-negative microorganism selected from the group consisting of *Gluconobacter, Rhizobium, Bradyrhizobium, Alcaligenes, Rhodobacter, Rhodococcus. Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas* (e.g., *Zymomonas mobilis*), *Zymobacter* (e.g., *Zymobacter palmae*), and *Acetobacter* (e.g., *Acetobacter pasteurianus*).

In another embodiment, the pdc nucleic acid or gene is derived from a Gram-positive microorganism selected from the group consisting of *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Sarcina* (e.g. *Sarcina ventriculi*).

In one embodiment, the pdc nucleic acid or gene is derived from Gram-negative bacteria *Zymobacter palmae*.

In another embodiment, the pdc nucleic acid or gene is derived from the Gram-negative *Acetobacter pasteurianus*.

In yet another embodiment, the pdc nucleic acid or gene is derived from the Gram-positive bacterium *Sarcina ventriculi*.

In another embodiment, an isolated nucleic acid molecule of the present invention comprises a nucleotide sequence which is at least about 60-65%, advantageously at least about 70-75%, more preferable at least about 80-85%, and even more advantageously at least about 90-95% or more identical to a nucleotide sequence set forth as SEQ ID NO:1, SEQ ID NO:3, or SEQ ID NO:5.

In another embodiment, an isolated nucleic acid molecule hybridizes under stringent conditions to a nucleic acid molecule having a nucleotide sequence set forth as SEQ ID NO:1, SEQ ID NO:3, or SEQ ID NO:5. Such stringent conditions are known to those skilled in the art and can be found in *Current Protocols in Molecular Biology*, John Wiley & Sons, N.Y. (1989), 6.3.1-6.3.6. A particular, non-limiting example of stringent (e.g. high stringency) hybridization conditions are hybridization in 6×sodium chloride/sodium citrate (SSC) at about 45° C., followed by one or more washes in 0.2×SSC, 0.1% SDS at 50-65° C. Advantageously, an isolated nucleic acid molecule of the invention that hybridizes under stringent conditions to the sequence of SEQ ID NO:1, SEQ ID NO:3, or SEQ ID NO:5 corresponds to a naturally-occurring nucleic acid molecule. Typically, a naturally-occurring nucleic acid molecule includes an RNA or DNA molecule having a nucleotide sequence that occurs in nature.

A nucleic acid molecule of the present invention (e.g., a nucleic acid molecule having the nucleotide sequence of SEQ ID NO:1, SEQ ID NO:3, or SEQ ID NO:5 can be isolated using standard molecular biology techniques and the sequence information provided herein. For example, nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989) or can be isolated by the polymerase chain reaction using synthetic oligonucleotide primers designed based upon the sequence of SEQ ID NO:1, SEQ ID NO:3, or SEQ ID NO:5. A nucleic acid of the invention can be amplified using cDNA, mRNA or alternatively, genomic DNA, as a template and appropriate oligonucleotide primers according to standard PCR amplification techniques. In another embodiment, an isolated nucleic acid molecule of the invention comprises a nucleic acid molecule which is a complement of the nucleotide sequence shown in SEQ ID NO:1, SEQ ID NO:3, or SEQ ID NO:5.

Additional pdc nucleic acid sequences are those that comprise the nucleotide sequence of SEQ ID NO:1, SEQ ID NO:3, or SEQ ID NO:5, that encode a homologue of the polypeptide having the amino acid sequence set forth in SEQ ID NO:2, SEQ ID NO:4, or SEQ ID NO:6 (e.g., encode a polypeptide having at least 30%, 40%, 50%, 60%, 70%, 80%, 90%, 95% or more identity to the polypeptide having the amino acid sequence as set forth in SEQ ID NO:2, SEQ ID NO:4, or SEQ ID NO:6, and having a substantially identical activity as the polypeptide), hybridize under stringent conditions to all or a portion of a nucleic acid molecule having the nucleotide sequence of SEQ ID NO:1, SEQ ID NO:3, or SEQ ID NO:5 or to all or a portion of a nucleic acid molecule that encodes a polypeptide having the amino acid sequence of SEQ ID NO:2, SEQ ID NO:4, or SEQ ID NO:6, or are complementary to a pdc nucleotide sequence as set forth herein.

In yet another embodiment, an isolated pdc nucleic acid molecule or gene encodes a homologue of the PDC polypeptide having the amino acid sequence of SEQ ID NO:2, SEQ ID NO:4, or SEQ ID NO:6. Typically, the term "homologue" includes a polypeptide or polypeptide sharing at least about 30-35%, advantageously at least about 35-40%, more advantageously at least about 40-50%, and even more advantageously at least about 60%, 70%, 80%, 90% or more identity with the amino acid sequence of a wild-type polypeptide or polypeptide described herein and having a substantially equivalent functional or biological activity as the wild-type polypeptide or polypeptide. For example, a PDC homologue shares at least about 30-35%, advantageously at least about 35-40%, more advantageously at least about 40-50%, and even more advantageously at least about 60%, 70%, 80%, 90% or more identity with the polypeptide having the amino acid sequence set forth as SEQ ID NO:2, SEQ ID NO:4, or SEQ ID NO:6, and has a substantially equivalent functional or biological activity (i.e., is a functional equivalent) of the polypeptide having the amino acid sequence set forth as SEQ ID NO:2, SEQ ID NO:4, or SEQ ID NO:6 (e.g., has a substantially equivalent pyruvate decarboxylase activity).

In an embodiment, an isolated pdc nucleic acid molecule or gene comprises a nucleotide sequence that encodes a polypeptide as set forth in any one of SEQ ID NO:2, SEQ ID NO:4, or SEQ ID NO:6.

In another embodiment, an isolated pdc nucleic acid molecule hybridizes to all or a portion of a nucleic acid molecule having the nucleotide sequence set forth in SEQ ID NO:1, SEQ ID NO:3, or SEQ ID NO:5 or hybridizes to all or a portion of a nucleic acid molecule having a nucleotide sequence that encodes a polypeptide having the amino acid sequence of any of SEQ ID NO:2, SEQ ID NO:4, or SEQ ID NO:6.

Such hybridization conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A particular, non-limiting example of stringent hybridization conditions includes hybridization in 4×sodium chloride/sodium citrate (SSC), at about 65-70° C. (or hybridization in 4×SSC plus 50% formamide at about 42-50° C.) followed by one or more washes in 1×SSC, at about 65-70° C. A particular, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A particular, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.)=2(# of A+T bases)+4(# of G+C bases). For hybrids between 18 and 49 base pairs in length, $T_m$(° C.)=81.5+16.6 ($\log_{10}$[Na$^+$])+0.41 (% G+C)−(600/N), where N is the number of bases in the hybrid, and [Na$^+$] is the concentration of sodium ions in the hybridization buffer ([Na$^+$] for 1×SSC=0.165 M).

It will also be recognized by the skilled practitioner that additional reagents can be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional, non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or, alternatively, 0.2×SSC, 1% SDS). In another embodiment, an isolated nucleic acid molecule comprises a nucleotide sequence that is complementary to a pdc nucleotide sequence as set forth herein (e.g., is the full complement of the nucleotide sequence set forth as SEQ ID NO:1, SEQ ID NO:3, or SEQ ID NO:5).

Yet another embodiment of the present invention features mutant or chimeric pdc nucleic acid molecules or genes. Typically, a mutant nucleic acid molecule or mutant gene as described herein, includes a nucleic acid molecule or gene having a nucleotide sequence which includes at least one alteration (e.g., substitution, insertion, deletion) such that the polypeptide or polypeptide that can be encoded by said mutant exhibits an activity that differs from the polypeptide or polypeptide encoded by the wild-type nucleic acid molecule or gene. Typically, a chimeric pdc includes an entire domain derived from another PDC that is engineered (fused, exchanged) with a corresponding domain in a PDC. Advantageoulsy, a mutant nucleic acid molecule or mutant gene (e.g., a mutant pdc gene) encodes a PDC polypeptide having improved activity, e.g., decarboxylase activity (e.g., substrate affinity (e.g., to pyruvate); thermostability; activity at a different pH; or codon usage (e.g., for improved expression in the recipient host cell).

III. Recombinant Nucleic Acid Molecules and Vectors

The present invention further features recombinant nucleic acid molecules (e.g., recombinant DNA molecules) that include nucleic acid molecules and/or genes described herein (e.g., isolated nucleic acid molecules and/or genes), advantageously pdc genes, more advantageously pdc genes derived from a Gram-negative or Gram-positive bacterium.

The present invention further features vectors (e.g., recombinant vectors) that include nucleic acid molecules (e.g., isolated or recombinant nucleic acid molecules and/or genes) described herein. In particular, recombinant vectors are featured that include nucleic acid sequences that encode bacterial gene products as described herein, advantageously pdc gene products, more advantageously pdc gene products of a Gram-negative or a Gram-positive bacterium, even more advantageously pdc gene products derived from *Zymobacter palmae*, *Acetobacter pasteurianus*, or *Sarcina ventriculi*.

The recombinant vector (e.g., plasmid, phage, phasmid, virus, cosmid or other purified nucleic acid vector) can been altered, modified or engineered such that it contains greater, fewer or different nucleic acid sequences than those included in the native or natural nucleic acid molecule from which the recombinant vector was derived. Advantageously, the recombinant vector includes a pdc gene or recombinant nucleic acid molecule including such a pdc gene, operably linked to regulatory sequences, for example, promoter sequences, terminator sequences and/or artificial ribosome binding sites (RBSs), as defined herein.

Typically, the pdc gene is operably linked to regulatory sequence(s) in a manner which allows for expression (e.g., enhanced, increased, constitutive, basal, attenuated, decreased or repressed expression) of the nucleotide sequence, advantageously expression of a gene product encoded by the nucleotide sequence (e.g., when the recombinant nucleic acid molecule is included in a recombinant vector, as defined herein, and is introduced into a microorganism).

The regulatory sequence includes nucleic acid sequences which affect (e.g., modulate or regulate) expression of other nucleic acid sequences. In one embodiment, a regulatory sequence is included in a recombinant nucleic acid molecule or recombinant vector in a similar or identical position and/or orientation relative to a particular gene of interest as is observed for the regulatory sequence and gene of interest as it appears in nature, e.g., in a native position and/or orientation. For example, a gene of interest can be included in a recombinant nucleic acid molecule or recombinant vector operably linked to a regulatory sequence which accompanies or is adjacent to the gene of interest in the natural organism (e.g., operably linked to "native" regulatory sequences, for example, to the "native" promoter). Alternatively, a gene of interest can be included in a recombinant nucleic acid molecule or recombinant vector operably linked to a regulatory sequence which accompanies or is adjacent to another (e.g., a different) gene in the natural organism. Alternatively, a gene of interest can be included in a recombinant nucleic acid molecule or recombinant vector operably linked to a regulatory sequence from another organism. For example, regulatory sequences from other microbes (e.g., other bacterial regulatory sequences, bacteriophage regulatory sequences and the like) can be operably linked to a particular gene of interest.

In one embodiment, a regulatory sequence is a non-native or non-naturally-occurring sequence (e.g., a sequence which has been modified, mutated, substituted, derivatized, deleted including sequences which are chemically synthesized). Advantageous regulatory sequences include promoters, enhancers, termination signals, anti-termination signals and other expression control elements (e.g., sequences to which repressors or inducers bind and/or binding sites for transcriptional and/or translational regulatory polypeptides, for example, in the transcribed mRNA). Such regulatory sequences are described, for example, in Sambrook, J., Fritsh, E. F., and Maniatis, T. *Molecular Cloning: A Laboratory Manual.* 2nd, ed, Cold Spring Harbor Laboratory, Cold Spring Harbor Laboratory Press, Cold Spring Harbor, N.Y., 1989. Regulatory sequences include those which direct constitutive expression of a nucleotide sequence in a microorganism (e.g., constitutive promoters and strong constitutive promoters); those which direct inducible expression of a nucleotide sequence in a microorganism (e.g., inducible promoters, for example, xylose inducible promoters); and those which attenuate or repress expression of a nucleotide sequence in a microorganism (e.g., attenuation signals or repressor sequences). It is also within the scope of the present invention to regulate expression of a gene of interest by removing or deleting regulatory sequences. For example, sequences involved in the negative regulation of transcription can be removed such that expression of a gene of interest is enhanced.

In one embodiment, a recombinant nucleic acid molecule or recombinant vector of the present invention includes a nucleic acid sequence or gene that encodes at least one bacterial pdc gene product operably linked to a promoter or promoter sequence. Advantageous promoters of the present invention include native promoters, surrogate promoters and/or bacteriophage promoters. In one embodiment, a promoter is a promoter associated with a biochemical housekeeping gene or a promoter associated with a ethanologenic pathway. In another embodiment, a promoter is a bacteriophage promoter. Other promoters include tef (the translational elongation factor (TEF) promoter) and pyc (the pyruvate carboxylase (PYC) promoter), which promote high level expression in Bacillus (e.g. Bacillus subtilis). Additional advantageous promoters, for example, for use in Gram positive microorganisms include, but are not limited to, the amyE promoter or phage SP02 promoters. Additional advantageous promoters, for example, for use in Gram negative microorganisms include, but are not limited to tac, trp, tet, trp-tet, lpp, lac, lpp-lac, lacIq, T7, T5, T3, gal, trc, ara, SP6, $\lambda$-$p_R$ or $\lambda$-$P_L$.

In another embodiment, a recombinant nucleic acid molecule or recombinant vector of the present invention includes a terminator sequence or terminator sequences (e.g., transcription terminator sequences). Typically, terminator sequences refer to the regulatory sequences which serve to terminate transcription of a gene. Terminator sequences (or tandem transcription terminators) can further serve to stabilize mRNA (e.g., by adding structure to mRNA), for example, against nucleases.

In yet another embodiment, a recombinant nucleic acid molecule or recombinant vector of the present invention includes sequences which allow for detection of the vector containing said sequences (i.e., detectable and/or selectable markers), for example, sequences that overcome auxotrophic mutations, for example, ura3 or ilvE, fluorescent markers, and/or calorimetric markers (e.g., lacZ/$\beta$-galactosidase), and/or antibiotic resistance genes (e.g., bla or tet).

It is understood that any one of the pdc genes of the invention can be introduced into a vector also comprising one or more ethanologenic genes (e.g., alcohol dehydrogenase (i.e., adh)) and/or a gene encoding a gene product suitable for fermenting a sugar or degrading a sugar for subsequent fermentation as described for example, in Examples 8 and 9 and as provided in U.S. Pat. Nos. 5,821,093; 5,482,846; 5,424,202; 5,028,539; 5,000,000; 5,487,989, 5,554,520, and 5,162,516. Such two or more genes can be expressed independently using separate regulatory elements (e.g., promoters), common regulatory element(s), native regulatory element(s), or a combination thereof.

IV. Isolated Polypeptides

Another aspect of the present invention features isolated polypeptides (e.g., isolated ethanologenic enzymes, for example, pyruvate decarboxylase (PDC)). In one embodiment, PDC polypeptides are produced by recombinant DNA techniques and can be isolated from microorganisms of the present invention by an appropriate purification scheme using standard polypeptide purification techniques. In another embodiment, polypeptides are synthesized chemically using standard peptide synthesis techniques.

An isolated or purified polypeptide (e.g., an isolated or purified PDC) is substantially free of cellular material or other contaminating polypeptides from the microorganism from which the polypeptide is derived, or substantially free from chemical precursors or other chemicals when chemically synthesized. In one embodiment, an isolated or purified polypeptide has less than about 30% (by dry weight) of contaminating polypeptide or chemicals, more advantageously less than about 20% of contaminating polypeptide or chemicals, still more advantageously less than about 10% of contaminating polypeptide or chemicals, and most advantageously less than about 5% contaminating polypeptide or chemicals.

In one embodiment, the PDC polypeptide or gene product is derived from a Gram-positive or Gram-negative bacterium. Advantageously, the PDC polypeptide or gene product is derived from a Gram-negative microorganism selected from the group consisting of *Gluconobacter, Rhizobium, Bradyrhizobium, Alcaligenes, Rhodobacter, Rhodococcus. Azospirillum, Rhodospirillum, Sphingomonas, Burkholderia, Desuljomonas, Geospirillum, Succinomonas, Aeromonas, Shewanella, Halochromatium, Citrobacter, Escherichia, Klebsiella, Zymomonas* (e.g, *Zymomonas mobilis*), *Zymobacter* (e.g., *Zymobacter palmae*), and *Acetobacter* (e.g, *Acetobacter pasteurianus*).

In another embodiment, the PDC polypeptide or gene product is derived from a Gram-positive microorganism selected from the group consisting of *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Sarcina* (e.g. *Sarcina ventriculi*). Advantageously, the gene product is derived from a microorganism selected from the group consisting of the Gram-negative bacteria *Zymobacter palmae, Acetobacter pasteurianus*, and the Gram-positive bacterium *Sarcina ventriculi*.

Included within the scope of the present invention are PDC polypeptides or gene products that are *Zymobacter palmae, Acetobacter pasteurianus*, or *Sarcina ventriculi*—derived polypeptides or gene products encoded by naturally-occurring bacterial genes. Further included within the scope of the present invention are bacterial-derived polypeptides or gene products which differ from naturally-occurring bacterial and/or *Zymobacter palmae, Acetobacter pasteurianus*, or *Sarcina ventriculi* genes (e.g., pdc), for example, genes which have nucleic acids that are mutated, inserted or deleted, but which encode polypeptides substantially similar to the naturally-occurring gene products of the present invention, e.g., comprise a pyruvate decarboxylase activity.

For example, it is well understood that one of skill in the art can mutate (e.g., substitute) nucleic acids which, due to the degeneracy of the genetic code, encode for an identical amino acid as that encoded by the naturally-occurring gene. This may be desirable in order to improve the codon usage of a nucleic acid to be expressed in a particular organism. Moreover, it is well understood that one of skill in the art can mutate (e.g., substitute) nucleic acids which encode for conservative amino acid substitutions. It is further well understood that one of skill in the art can substitute, add or delete amino acids to a certain degree without substantially affecting the function of a gene product (e.g., decarboxylase activity) as compared with a naturally-occurring gene product, each instance of which is intended to be included within the scope of the present invention. The decarboxylase activity and, for example, enzyme/substrate affinity, enzyme thermostability, and/or enzyme activity at various pHs, can be readily determined using the assays described herein.

In an embodiment, an isolated polypeptide of the present invention (e.g., an isolated pyruvate decarboxylase enzyme, for example isolated PDC polypeptide has an amino acid sequence shown in SEQ ID NO:2, SEQ ID NO:4, SEQ ID NO:6, or SEQ ID NO:8. In other embodiments, an isolated polypeptide of the present invention is a homologue of the at least one of the polypeptides set forth as SEQ ID NO:2, SEQ ID NO:4, SEQ ID NO:6, or SEQ ID NO:8 (e.g., comprises an amino acid sequence at least about 30-40% identical, advantageously about 40-50% identical, more advantageously about 50-60% identical, and even more advantageously about 60-70%, 70-80%, 80-90%, 90-95% or more identical to the amino acid sequence of SEQ ID NO:2, SEQ ID NO:4, SEQ ID NO:6, or SEQ ID NO:8, and has an activity that is substantially similar to that of the polypeptide encoded by the amino acid sequence of SEQ ID NO:2, SEQ ID NO:4, SEQ ID NO:6, or SEQ ID NO:8, respectively.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions×100), advantageously taking into account the number of gaps and size of said gaps necessary to produce an optimal alignment.

The comparison of sequences and determination of percent identity between two sequences can be accomplished using a mathematical algorithm. A particular, non-limiting example of a mathematical algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST polypeptide searches can be performed with the XBLAST program, score=50, wordlength=3 to obtain amino acid sequences homologous to polypeptide molecules of the invention. To obtain gapped alignments for comparison purposes, Gapped BLAST can be utilized as described in Altschul et al. (1997) Nucleic Acids Research 25(17): 3389-3402. When utilizing BLAST and Gapped BLAST programs, the default parameters of the respective programs (e.g., XBLAST and NBLAST) can be used. See http://www.ncbi.nlm.nih.gov. Another particular, non-limiting example of a mathematical algorithm utilized for the comparison of sequences is the algorithm of Myers and Miller (1988) *Comput Appl Biosci.* 4:11-17. Such an algorithm is incorporated into the ALIGN program available, for example, at the GENESTREAM network server, IGH Montpellier, FRANCE or at the ISREC server. When utilizing the ALIGN program for comparing amino acid sequences, a PAM120 weight residue table, a gap length penalty of 12, and a gap penalty of 4 can be used.

In another embodiment, the percent identity between two amino acid sequences can be determined using the GAP program in the GCG software package, using either a Blossom 62 matrix or a PAM250 matrix, and a gap weight of 12, 10, 8, 6, or 4 and a length weight of 2, 3, or 4. In yet another embodiment, the percent homology between two nucleic acid sequences can be accomplished using the GAP program in the GCG software package (available at http://www.gcg.com), using a gap weight of 50 and a length weight of 3.

Based on the foregoing isolated PDC polypeptides, immunospecific antibodies can be raised against a PDC polypeptide, or portion thereof, using standard techniques as described herein.

V. Methods of Use

Methods for Producing Acetaldehyde

The clean and efficient production of acetaldehyde as a desirable product has widespread commercial and industrial applications. For example, acetaldehyde is used in the production of acetic acid, flavorings, foods, beverages, perfumes, plastics, aniline dyes, synthetic rubber manufacturing, the silvering of mirrors, gelatin fiber hardening, and in laboratory research. In addition, acetaldehyde serves as a substrate for the production of ethanol through, for example, fermentation.

Accordingly, the present invention includes methods for the conversion of a substrate, for example, pyruvate or a pyruvate analog, into acetaldehyde, using the PDC enzymes of the invention. In one embodiment, the invention provides methods for producing acetaldehyde form pyruvate using microorganisms (e.g., a recombinant microorganisms) expressing a pdc gene and gene product (PDC) as described herein. The methods also include biological processes which result in the production (e.g., transformation or conversion) of pyruvate, or convertible analog thereof, which can be converted or decarboxylated to acetaldehyde, or an analog thereof.

The method comprises contacting a microorganism which expresses a pdc gene and gene product of the invention, and optionally, one or more ethanologenic genes, with a sugar, carbon skeleton capable of being converted into pyruvate, pyruvate, or an analog thereof, under culture conditions such that acetaldehyde (or analog thereof) is produced.

In another embodiment of the invention, the above-mentioned microorganism can be processed into a enzymatic lysate for performing the above conversion reaction. In yet another embodiment, the pdc gene product is purified, as described herein, for carrying out the conversion reaction.

The microorganism(s) and/or enzymes (e.g., in the form of a lysate, partially purified, or purified)) used in the conversion reactions are in a form allowing them to perform their intended function (e.g., producing a desired compound, e.g., acetaldehyde). The microorganisms can be whole cells, or can be only those portions of the cells necessary to obtain the desired end result. The microorganisms can be suspended (e.g., in an appropriate solution such as buffered solutions or media), rinsed (e.g., rinsed free of media from culturing the microorganism), acetone-dried, immobilized (e.g., with polyacrylamide gel or k-carrageenan or on synthetic supports, for example, beads, matrices and the like), fixed, cross-linked or permeabilized (e.g., have permeabilized membranes and/or walls such that compounds, for example, substrates, intermediates or products can more easily pass through said membrane or wall).

Purified or unpurified PDC enzymes (alone or in combination with other ethanologenic enzyme(s)) can also be used in the conversion reactions. The enzyme can be in a form that allows it to perform its intended function (e.g., obtaining the desired compound, e.g., acetaldehyde, or, if in the presence of the necessary ethanologenic gene products, ethanol). For example, the enzyme can be in free form or immobilized.

Methods for Producing Ethanol

In one embodiment of the present invention, the host cell having the above mentioned attributes is also ethanologenic. Accordingly, the invention provides methods for producing ethanol using such host cells (or extracts/enzymes derived therefrom). In addition, the host cells can be applied in synergistically degrading or depolymerizing a complex saccharide into a monosaccharide. Subsequently, the cell can catabolize the simpler sugar into ethanol by fermentation. This process of concurrent complex saccharide depolymerization into smaller sugar residues followed by fermentation is referred to as simultaneous saccharification and fermentation (SSF).

Typically, fermentation conditions are selected that provide an optimal pH and temperature for promoting the best growth kinetics of the producer host cell strain and catalytic conditions for the enzymes produced by the culture (Doran et al., (1993) *Biotechnol. Progress.* 9:533-538). For example, for *Klebsiella*, e.g., the P2 strain, optimal conditions were determined to be between 35-37° C. and pH 5.0-pH 5.4. Under these conditions, even exogenously added fungal endoglucanases and exoglucanases are quite stable and continue to function for long periods of time. Other conditions are discussed in the Examples. Moreover, it will be appreciated by the skilled artisan, that only routine experimentation is needed, using techniques known in the art, for optimizing a given fermentation reaction of the invention. See, for example, U.S. Pat. Nos. 5,424,202 and 5,916,787, which are specifically incorporated herein by this reference.

This invention is further illustrated by the following examples, which should not be construed as limiting.

Exemplification

Throughout the examples, the following materials and methods are used unless otherwise stated. Abbreviation are as follows: PDC, pyruvate decarboxylase; ADH, alcohol dehydrogenase; SDS-PAGE, sodium dodecyl sulfate-polyacrylamide gel electrophoresis; TPP, thiamine diphosphate; PCMS, para-chloromercuriphenyl-sulfonic acid; PCMB, para-chloromecuribenzoic acid; DTT, dithiothreitol; Apa, *Acetobacter pasteurianus*; Sve, *Sarcina ventriculi*; Zpa, *Zymobacter palmae*; Zmo *Z. mobilis*.

Materials and Methods

Strains and Media—*Z. palmae* strain T109 (IAM 14233, ATCC51623) was cultivated in ATCC1956 MY medium (10 g yeast extract, 20 g maltose, 2 g $KH_2PO_4$, and 5 g NaCl per liter) at 26° C. (200 rpm). *A. pasteurianus* strain NCIB8618 (ATCC 12874) was grown with aeration at 25° C. in minimal medium (H 5.0 to 5.5) supplemented with 2% (v/v) D-L-lactate as described previously (3, 13) with the addition of 0.1 ml per liter of 1% (v/v) antifoam. *E. coli* strains ER1648 $F^-$ fhuA2Δ(lacZ) r1 supE44 trp31 mcrA1272::Tn10($Tet^r$) his-1 rpsL104 ($Str^r$)xyl-7 mt1-2 metB1 Δ(mcrC-mrr)102:: Tn10($Tet^r$) (New England Biolabs, Beverly, Mass.), DH5α $F^-$ recA1 endA1 hsdR17($r_k^- m_k^+$) supE44 thi-1 gyrA relA1 (Life Technologies, Rockville, Md.), BL21 -CodonPlus-RIL $F^-$ ompT hsdS($r_B^- m_B^-$) dcm$^+$ $Tet^r$ galλ (DE3) endA Hte [argU ileY leuW $Cam^r$] (an *E. coli* B strain) (Stratagene, LaJolla, Calif.), and Rosetta (DE3) $F^-$ ompT $hsdS_B$ ($r_B^- M_B^-$) gal dcm lacY1 (pRARE) (Novagen, Madison, Wis.) were used for recombinant DNA experiments. *E. coli* strains were grown at 37° C. (200 rpm) in Luria-Bertani (LB) medium. Medium was supplemented with 2% (w/v) glucose and antibiotics including ampicillin (100 mg per liter), kanomycin (100 mg per liter), and chloramphenicol (30 mg per liter) as needed.

DNA Isolation and Cloning—Plasmid DNA was isolated using a Quantum Prep Plasmid Miniprep Kit from BioRad (Hercules, Calif.). DNA fragments were eluted from 0.8% SeaKem GTG agarose (FMC Bioproducts, Rockland, Me.) gels with 1×TAE buffer (40 mM Tris acetate, 2 mM EDTA, pH 8.5) using the Q1Aquick gel extraction kit from Qiagen (Valencia, Calif.). Genomic DNA was isolated using the method described by Harwood and Cutting (17).

Analysis of DNA and Polypeptide Sequences of *Z. palmae*—Plasmids were sequenced using the Sanger dideoxy method (42) using a LICOR sequencer (DNA Sequencing Facility, Department of Microbiology and Cell Science, University of Florida). Genpro 5.0 (Hoefer Scientific, San Francisco, Calif.), ClustalW version 1.81 (46), Treeview version 1.5 (39), and MultiAln (12) were used for DNA and polypeptide sequence alignments and comparisons. Deduced amino acid sequences were compared to polypeptide sequences in the GenBank, EMBL, and SwissProt at the National Center for Biotechnology Information (Bethesda, Md.) using the BLAST network server.

Purification of PDC Polypeptides—PDC purifications were performed as presented in Table 2. All procedures were performed at room temperature and all purification buffers contained 1 mM TPP and 1 mM $MgCl_2$ unless otherwise indicated. *S. ventriculi* PDC was purified from recombinant *E. coli* BL21-CodonPlus-RIL(pJAM419) and Rosetta (DE3) (pRARE, pJAM419) as previously described (45). *Z. mobilis* PDC was purified from recombinant *E. coli* DH5α (pLOI276) (11) using thermal treatment, Q-Sepharose, and Superdex 200 procedures as described below for the *Z. palmae* PDC with the exception that the *Z. mobilis* PDC was eluted from Q-Sepharose at 0.22 to 0.32 M NaCl.

(i) Purification of *Z. palmae* PDC—*Z. palmae* and *E. coli* DH5α (pJAM3440) cells were grown to stationary phase and harvested by centrifugation at 10,000×g (10 min, 4° C.). Cells (12 to 15 g wet wt) were resuspended in 6 volumes of 50 mM sodium phosphate buffer at pH 6.5 containing 1 mM TPP and 1 mM $MgCl_2$ (buffer A) and passed through a chilled French pressure cell at 20,000 lb per in$^2$. Cell debris was removed by centrifugation at 16,000×g (20 min, 4° C.). Cell lysate was heated to 60° C. for 30 min, chilled on ice for 15 min, and centrifuged at 16,000×g (30 min at 4° C.) to remove denatured polypeptides. The supernatant was applied to a HiLoad Q-Sepharose 26/10 column (Amersham Pharmacia Biotech, Piscataway, N.J.) equilibrated in 50 mM buffer A. The column was washed with 200 ml of 50 mM buffer A and a 400-ml linear 0-1 M NaCl gradient was applied at 4.0 ml per min. The peak of PDC activity eluted between 0.4 and 0.5 M NaCl and was pooled. The recombinant *Z. palmae* PDC from *E. coli* was purified to homogeneity by injecting aliquots (0.5 ml) onto a Superdex 200 10/30 column (Amersham Pharmacia Biotech) equilibrated with 50 mM buffer A containing 150 mM NaCl and 10% glycerol at 0.2 ml per min.

Purification of "native" PDC from *Z. palmae* required additional steps. Heat-treated lysate was applied to a hydroxyapatite CHT5-1 column (BioRad) equilibrated with 10 mM buffer A. The column was washed with 30 ml of 10 mM buffer A and a 30-ml linear 10 mM-1M sodium phosphate gradient was applied at 0.5 ml per min. The peak of PDC activity eluted at 0.45 to 0.5 M sodium phosphate and was pooled. Aliquots were further purified using a Superdex 200 10/30 column as described above. Solid ammonium sulfate was added to the combined active fractions to 1 M and then loaded onto a Phenyl Sepharose 6 Fast Flow (low sub) column (Amersham Pharmacia Biotech) equilibrated with 50 mM buffer A containing 1 M ammonium sulfate. After a 15-ml wash, the column was developed with a 15-ml decreasing linear gradient of 1-0 M ammonium sulfate at 0.5 ml per min. The peak of "native" PDC activity was eluted between 0.55 and 0.3 M salt.

(ii) Purification of *A. pasteurianus* PDC—PDC was purified from *A. pasteurianus* and *E. coli* ER1648(pJAM304) using heat-treatment, Q-Sepharose, Superdex 200, and hydroxyapatite as described for the *Z. palmae* PDC with the following modifications. Cells were passed through a French pressure cell at 30,000 lb per in$^2$. The PDC activity, which was eluted at 0.17 to 0.26 M NaCl from the Q-Sepharose column, was pooled and concentrated by dialysis against PEG8000 prior to loading onto the Superdex 200 column.

The *Z. palmae* and *A. pasteurianus* PDCs were stored for up to one month in 10% glycerol under liquid nitrogen without loss of activity. The *S. ventriculi* and *Z. mobilis* PDCs were stored at 4° C.

PDC Quantitation and Enzyme Activity Assay—Polypeptide concentration was determined using Bradford reagent with bovine serum albumin as the standard (BioRad). PDC activity was measured by the coupled assay with baker's yeast alcohol dehydrogenase (ADH) (Sigma-Aldrich, St. Louis, Mo.) as previously described (11). The reaction mixture contained 0.15 mM NADH, 5 mM MgCl$_2$, 0.1 mM TPP, 5 mM pyruvate, and 10 U ADH in 50 mM sodium citrate buffer at pH 5.0 and was measured at 25° C. unless otherwise indicated. One unit of enzyme activity is defined as the amount of enzyme that generates 1 µmol of acetaldehyde per min.

Molecular Mass and Amino Acid Sequence Determination of the PDC Polypeptide—Subunit molecular masses and enzyme purity were determined by sodium dodecyl sulfate-polyacrylamide gel electrophoresis (SDS-PAGE) using 12% polyacrylamide gels stained with Coomassie blue R-250 (26). Molecular weight standards for SDS-PAGE were as follows: phosphorylase b (97.4 kDa), serum albumin (66.2 kDa), ovalbumin (45 kDa), carbonic anhydrase (31 kDa), trypsin inhibitor (21.5 kDa), and lysozyme (14.4 kDa). For the determination of native molecular mass, samples were applied to a Superdex 200 10/30 column equilibrated in 50 mM sodium phosphate buffer at pH 6.5 with 150 mM NaCl. Molecular mass standards included: serum albumin (66 kDa), alcohol dehydrogenase (150 kDa), α-amylase (200 kDa), apoferritin (443 kDa), and thyroglobulin (669 kDa).

The N-terminal sequences of the purified PDC polypeptides were determined after SDS-PAGE and electroblotting of the polypeptides onto a polyvinylidene difluoride membrane (PVDF-PLUS) (Micron Separations Inc., Westborough, Mass.). Sequences were determined by automated Edman degradation at the Polypeptide Chemistry Core Facility of the University of Florida Interdisciplinary Center for Biotechnology Research.

Apoenzyme Preparation—Purified PDC (0.75 mg per 0.5 ml) was diluted with 1.5 ml of 50 mM sodium phosphate buffer at pH 9.0 and immediately concentrated 8-fold using a Centricon YM30 concentrator (Millipore, Bedford, Mass.). After adjusting the volume to 0.5 ml, the polypeptide was incubated at 25° C. for 45 min. PDC was purified from unbound cofactors by application to a Superdex 200 10/30 column equilibrated with 50 mM sodium phosphate buffer at pH 9.0 with 10% glycerol and 150 mM NaCl. Immediately after elution, the apoenzyme was diluted 5-fold into 50 mM sodium citrate buffer at pH 5.0, stored at 4° C., and used within 16 h for reconstitution assays. TPP was measured by fluorescence after oxidation to thichrome diphosphate using K$_3$Fe(CN)$_6$ in 15% NaOH (15). Excitation and emission wavelengths were 375$_{nm}$ and 430$_{nm}$, respectively. For reconstitution, apoenzyme (755 ng) was diluted into 1 ml of 50 mM sodium citrate buffer at pH 5.0 with 1 mM TPP and/or 1 mM of MgCl$_2$. The mixture was assayed for PDC activity in the same buffer.

Materials—Biochemicals were purchased from Sigma-Aldrich. Other organic and inorganic analytical grade chemicals were from Fisher Scientific (Atlanta, Ga.). Restriction endonucleases and DNA-modifying enzymes were from New England BioLabs. Digoxigenin-11-dUTP (2'-deoxyuridine-5'-triphosphate coupled by an 11-atom spacer to digoxigenin), alkaline phosphatase conjugated antibody raised against digoxigenin, and nylon membranes for colony and plaque hybridizations were from Roche Molecular Biochemicals. Positively charged nylon membranes for Southern hybridization were from Ambion (Austin, Tex.).

Example 1

Identification and Characterization of PDC Gene From Gram-Negative Bacterium *Zymobacter Palmae*

In this example, the identification and characterization of a PDC gene from the Gram-negative bacterium *Z. palmae* is described.

Briefly, a pyruvate decarboxylase (pdc) operon was isolated from a genomic library of *Zymobacter palmae* using a degenerate oligonucleotide probe based on the N-terminal amino acid sequence of the purified protein (FIG. 1). A 1.7-kb PstI to BamHI subclone of this fragment (pJAM3440) was found to be required for PDC activity in recombinant *E. coli*. Based on DNA sequence, a 1668-bp ORF (55 mol % G+C content) was identified in this region that encoded a putative PDC polypeptide (FIG. 1). A canonical Shine-Dalgarno sequence (GGAGG) was 10 bp upstream of the translation start codon (ATG). In addition, a putative −35 and −10 promoter (TTcACt-N$_{17}$-atTAAT, where N is any nucleotide and uppercase letters match the bacterial promoter consensus) was located 16 to 44 bp upstream of the start codon (18). Downstream (21 bp) of the translation stop codon was a 62 bp sequence predicted to form two stem-loop structures followed by a 16 bp AT-rich region, consistent with ρ-independent transcription termination (18). All four bacterial pdc genes, including those from *Z. mobilis*, *S. ventriculi*, and *A. pasteurianus*, are predicted to be independently transcribed from a monocistronic operon (11, 40, 45).

The deduced PDC polypeptide of *Z. palmae* (ZpaPDC) contained 556 amino acids (including the N-terminal methionine) with an anhydrous molecular mass of 60,113 Da (FIG. 4). This is similar to the three other bacterial PDCs which range from 552 to 568 amino acids and 59,830 to 61,809 Da. GenBank accession number AF474145 has been assigned to the *Z. palmae* sequence.

Example 2

Identification and Characterization of PDC Gene From Gram-Negative Aerobic Bacterium *Acetobacter Pasteurianus*

In this example, the identification and characterization of a PDC gene from the Gram-negative bacterium *Acetobacter pasteurianus* is described.

Briefly, a chromosomal DNA was isolated from cells of *A. pasteurianus* using the method described by Harwood et al. (17). For Southern analysis, the genomic DNA (1 to 2 μg per lane) was cleaved with restriction enzymes (AatII, BamHI, ClaI, EcoRI, and HincII), separated by gel electrophoresis (0.8% agarose), and transferred by downward capillary action to positively charged nylon membranes. Membranes were equilibrated at 60° C. for 2 h in 5×SSC (1×SSC is 0.15 M NaCl plus 0.015 M sodium citrate) containing 1% blocking reagent, 0.1% N-lauroylsarcosine, and 0.02% sodium dodecyl sulfate (SDS). Random primers were used to label a probe with dixoigenin-11-dUTP using a 0.7-kb KpnI fragment of the Z. mobilis pdc gene as the template. After the labeled-probe (1 ng per ml) was added, membranes were incubated at 60° C. for 14 h and washed twice with a solution containing 2×SSC and 0.1% SDS (5 min per wash) and twice with a solution containing 0.5×SSC and 0.1% SDS (15 min per wash at 60° C.). Signals were visualized by chemiluminescence using X-ray film.

A sub-genomic library was generated using 5- to 7-kb AatII fragments of *A. pasteurianus* chromosomal DNA. Overhangs were converted to blunt ends using Vent DNA polymerase and ligated into the blunt (Vent DNA polymerase), de-phosphorylated (calf intestinal alkaline phosphatase) XhoI site of pLITMUS28. After transformation, recombinants were screened by hybridization using conditions similar to those for Southern analysis, which allowed the isolation of plasmid pJAM301 containing the full-length pdc and aldI genes (FIG. 2).

The *A. pasteurians* DNA fragment (4.2 kb) in pJAM301 was then subcloned (FIG. 2) and sequenced by the Sanger dideoxy method (42) using a LICOR sequencer (DNA Sequencing Facility, Department of Microbiology and Cell Science, University of Florida). GenBank accession number AF368435 has been assigned to this sequence.

Genepro 5.0 (Riverside Scientific, Seattle, Wash.), ClustalW version 1.81 (Thompson et al., 1994), Treeview version 1.5 (Page, 1996), and MultiAln (Corpet, 1988) were used for DNA and/or polypeptide sequence alignments and comparisons. Deduced amino acid sequences were compared to polypeptide sequences available in the GenBank, EMBL, and SwissProt databases at the National Center for Biotechnology Information (Bethesda, Md.) using the BLAST network server.

Figure 2:
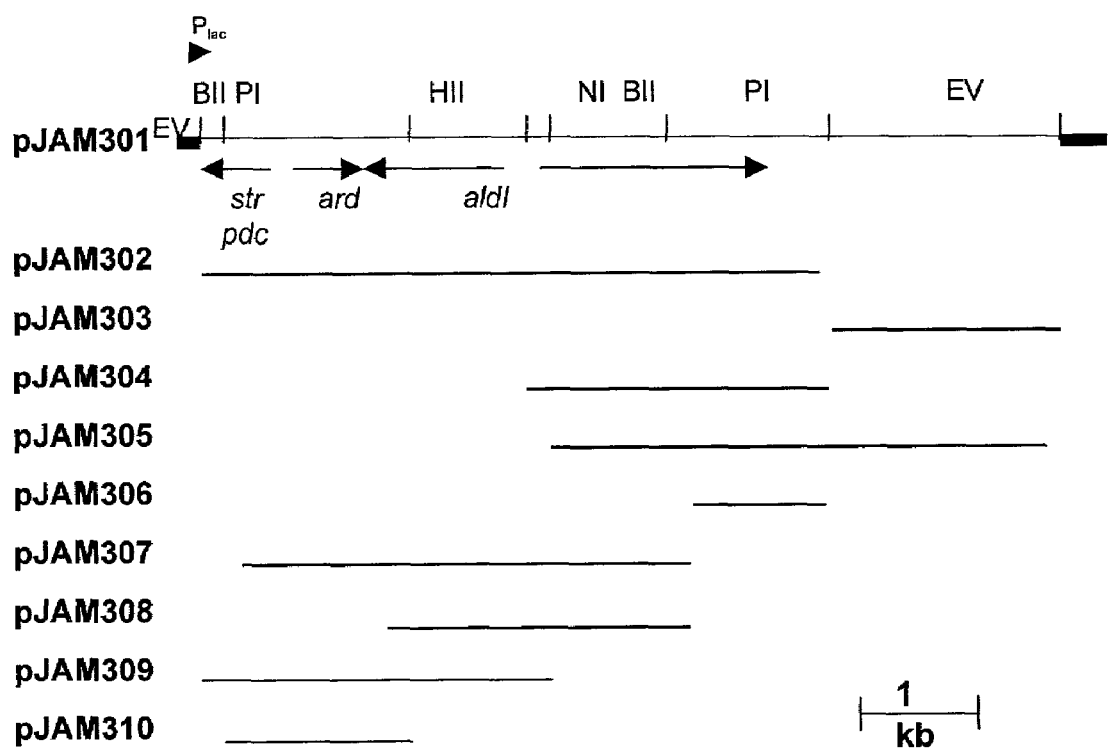
FIG. 2 shows a schematic representation of the *Acetobacter pasteurianus* pdc gene. The plasmid pJAM301 carries a 6,337-bp AatII fragment of *A. pasteurianus* genomic DNA ligated into the XhoI site of plasmid vector pLITMUS28. The 3'- and 5'-overhangs generated by AatII and XhoI were blunt-ended with Vent DNA polymerase prior to ligation. The remaining plasmids were derived from pJAM301 and were used for DNA sequence analysis. Plasmid pJAM304 was used to produce the *A. pasteurianus* PDC protein in recombinant *E. coli*. Arrowheads indicate the directions of transcription and translation of the deduced ORFs.

A fragment of the pyruvate decarboxylase (pdc) gene from Z. mobilis was used as a DNA-hybridization probe to isolate a 6,337 bp AatII fragment with 58.5% G+C content from *A. pasteurians* genomic DNA (FIG. 2). Based on a Blast analysis of the DNA sequence, a pdc gene was identified. This gene is predicted to encode a polypeptide of 548 amino acids (including the N-terminal formyl-methionine) with a calculated pI of 5.49 and an anhydrous molecular mass of 58,873 Da (FIG. 5). The codon usage of the pdc gene was compared to the two other bacterial pdc genes, Z. mobilis (11, 34, Reynen and Sahm, J Bacteriol. 170:3310-3313 (1988)) and S. ventriculi, as well as the E. coli K-12 genome (Table 1). Consistent with high G+C content for the *A. pasteurians* pdc gene (60.4%), the codons had a predominance of C and/or G in the third base position with exception of those for Glu, His, and Tyr (Table 1). This is in contrast to the Z. mobilis (52.4%) and S. ventriculi (30.9%) pdc genes that have lower G+C content and differ in their codon usage.

Analysis of the 5'-end of the *A. pasteurians* pdc gene revealed a canonical Shine-Dalgarno sequence that is 8 bp upstream of the predicted translation start codon of GTG. In addition, a region 72 to 101 bp upstream of the pdc gene has high identity to eubacterial −35 and −10 consensus sequence for a $\sigma^{70}$-dependent promoter. Immediately downstream (17 bp) of the pdc translation stop codon is a series of predicted hairpin loop structures that are followed by an AT-rich region, indicating p-independent termination of pdc transcription. Thus, the *A. pasteurians* pdc gene was determined to be transcribed as a monocistronic operon like that of Z. mobilis (11) and S. ventriculi pdc genes.

Additional open reading frames (ORFs) were identified in the pdc gene region including an ORF denoted as aldI, which is divergently transcribed from pdc (FIG. 2). The putative aldI gene is predicted to encode a polypeptide of 357 amino acids (including the N-terminal formyl-methionine) with a calculated molecular mass of 38,108 Da and pI of 6.32. The deduced polypeptide sequence (AldI) is very similar to members of the $Zn^{2+}$- and $NAD^+$-dependent medium-chain ADH family (class III) most notably the glutathione-dependent formaldehyde dehydrogenases (GSH-FDH) (Jornvall et al., *Eur. J. Biochem* 167:195-201 (1987)). Amino acid residues that are probable ligands for both the structural (C-92, C-95, C-98, and C-1 06) and catalytic (C-40, H-62, and C-169) zinc ions important for GSH-FDH activity are conserved. A Rossman fold consensus sequence (residues 194-GLGGIG-199) is also present and indicates that AldI can bind $NAD(P)^+$. The predicted *A. pasteurians* AldI polypeptide has little sequence identity to the three subunits of the membrane-bound ALD or ADH enzymes, necessary for ethanol oxidation in Acetobacter (Thumer et al., 1997; Kondo and Horinouchi, J. Bacteriol. 177:5048-5055 (1997)). Instead, this predicted polypeptide was determined to have close evolutionary ties to GSH-FDH polypeptides. Most notably, the *A. pasteurianus* polypeptide encoded by aldI clusters with GSH-FDH enzymes from the α-proteobacteria, the cynaobacterium *Anabaena azolla*, and to a lesser extent with the β- and and γ-proteobacteria consistent with the taxonomic classification of the acetic acid bacteria.

Subclones of the *A. pasteurians* AatII 6.3-kb genomic fragment carrying the pdc gene on a high copy number plasmid were analyzed for PDC activity by the ADH coupled assay. Significant levels of PDC activity were only detected for strains carrying plasmid pJAM304, which has the complete pdc open reading frame in addition to 124 bp upstream and 236 bp downstream of the gene (FIGS. 2 and 5). GenBank accession number AR368435 has been assigned to the *Acetobacter pasteurianus* sequence.

Example 3

Identification and Characterization of PDC Gene From Gram-Positive Bacterium *Sacina Ventriculi*

In this example, the identification and characterization of a PDC gene from the Gram-positive bacterium *Sarcina ventriculi* is described.

Briefly, a degenerate oligonucleotide 5'-AARGARGTNAAYGTNGARCAYATGTTYGGNGT-3' (SEQ ID NO:11) was synthesized based on the N-terminal amino acid sequence of PDC purified from *S. ventriculi* (Lowe and Zeikus, 1992)(where, R is A or G; N is A, C, G, or T; Y is C or T). This oligonucleotide was labeled at the 3'-end using terminal transferase with digoxigenin-11-dUTP and dATP as recommended by the supplier (Roche Molecular Biochemicals) and was used to screen genomic DNA from S. ventriculi.

For Southern analysis, genomic DNA was digested with BglI, EcoRI, or HincII, separated by 0.8% agarose electrophoresis, and transferred to positively charged nylon membranes (Southern, 1975). Membranes were equilibrated at 58° C. for 2 h in 5×SSC (1×SSC is 0.15 M NaCl plus 0.015 M sodium citrate) containing 1% blocking reagent (Roche Molecular Biochemicals), 0.1% N-lauroylsarcosine, and 0.02% SDS. After the probe (0.2 pmol per ml) and Poly(A) (0.01 mg per ml) were added, membranes were incubated at 58° C. for 18.5 h. Membranes were washed twice with 2×SSC containing 0.1% SDS (5 min per wash) at 25° C. and twice with 0.5×SSC containing 0.1% SDS (15 min per wash) at 58° C. Signals were visualized using colorimetric detection according to supplier (Roche Molecular Biochemicals).

Figure 3:
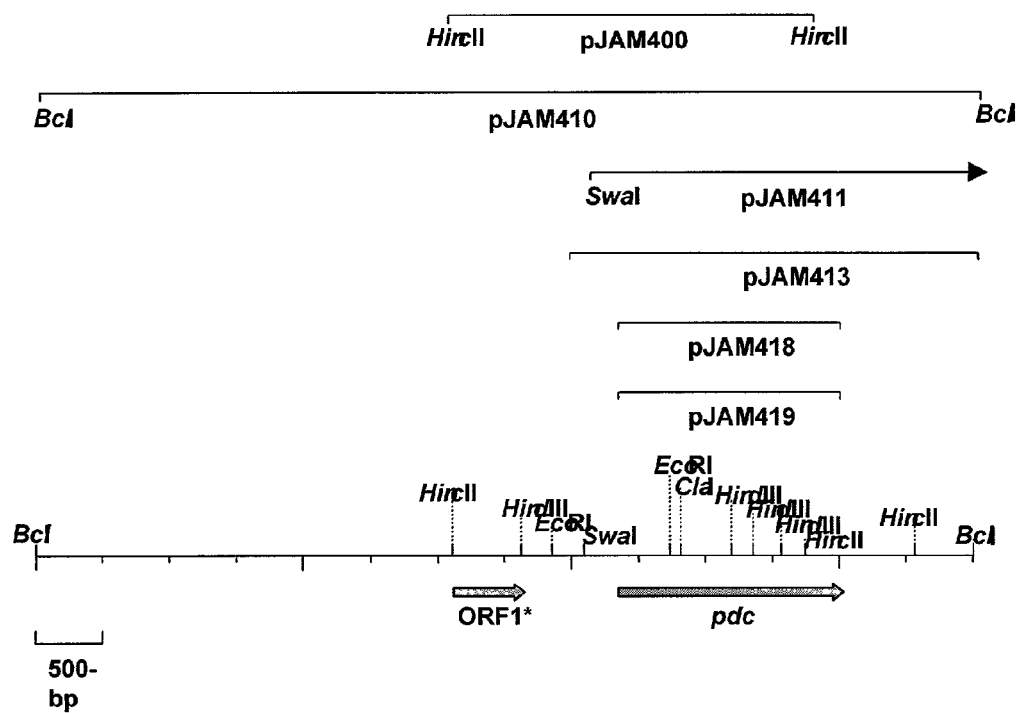
FIG. 3 shows a schematic representation of the *S. ventriculi* pdc gene, various plasmids produced for sequencing and characterizing the pdc locus and the plasmids pJAM413, pJAM419, and pJAM418 which comprise the pdc open reading frame and are suitable for the high expression of the pdc gene in bacteria.

For generation of a subgenomic library in plasmid pBR322, S. ventriculi chromosomal DNA was digested with HincII and fractionated by electrophoresis. The 2.5- to 3.5-kb HincII DNA fragments were ligated into the EcoRV site of pBR322 and transformed into E. coli SE2309. Colonies were screened with the degenerate oligonucleotide by colorimetric detection. By this method, plasmid pJAM400 that carries HincII fragment containing 1,350 bp of the pdc gene was isolated (FIG. 3).

The λ BlueSTAR Vector System (Novagen) was used to create an additional subgenomic library to facilitate isolation of the full-length pdc gene from S. ventriculi. Genomic DNA was digested with BclI, separated by electrophoresis in 0.8% agarose, and the 6.5- to 8.5-kb fragments were ligated with the λBlueSTAR BamHI arms. In vitro packaging and plating of phage was performed according to the supplier (Novagen). A DNA probe was generated using an 800-bp EcoRI fragment of the pdc gene from pJAM400 that was labeled with digoxigenin-11-dUTP using the random primed method as recommended by the supplier (Roche Molecular Biochemicals). Plaques were screened using colorimetric detection. Cre-loxP-mediated subcloning was used to circularize the DNA of the positive plaques by plating λ BlueSTAR phage with E. coli BM25.8 that expresses Cre recombinase (Novagen). The circularized plasmid pJAM410 was then purified and electroporated into E. coli DH5α.

For generation of a pdc expression vector, the promoterless pdc gene was subcloned into pET21d after amplification from pJAM413 (FIG. 3) by the polymerase chain reaction (PCR). Primers were designed for directional insertion using BspHI (oligo 1) and XhoI (oligo 2) restriction sites. The resulting fragment was ligated into compatible NcoI and XhoI sites of pET21d (Novagen) to produce pJAM419 (FIG. 3). The fidelity of the pdc gene was confirmed by DNA sequencing.

To determine the S. ventriculi pyruvate decarboxylase operon, the N-terminal amino acid sequence of the PDC polypeptide purified from S. ventriculi (Lowe and Zeikus, 1992) was used to generate a degenerate oligonucleotide for hybridization to genomic DNA. This approach facilitated the isolation of a 7.0-kb BclI genomic DNA fragment from S. ventriculi. The fragment was further subcloned in order to sequence both strands of a 3,886 bp HincII-to-HincII region that hybridized to the oligonucleotide probe (FIG. 3). Analysis of the DNA sequence reveals an open reading frame (ORF) of 1,656 bp encoding a polypeptide with an N-terminus identical to that of the previously purified S. ventriculi PDC (FIG. 6). The ORF is therefore designated pdc. A canonical Shine-Dalgarno sequence is present 7 bp upstream of the pdc translation start codon. In addition, a region 82 to 110 bp upstream of pdc has limited identity to the eubacterial –35 and –10 promoter consensus sequence. Downstream (43 bp) of the pdc translation stop codon is a region predicted to form a stem-loop structure followed by an AT-rich region, consistent with a p-independent transcription terminator. Thus, the S. ventriculi pdc is transcribed as a monocistronic operon like the Z. mobilis pdc gene (Conway et al., 1987).

A partial ORF was identified 722 bp upstream of pdc which encodes a 177 amino acid polypeptide fragment (ORF1*) (FIG. 3). ORF1* has identity (28-29%) to several hypothetical membrane polypeptides (GenBank accession numbers CAC11620, CAC24018, CAA22902) and is predicted to form several transmembrane spanning domains (data not shown). The gene encoding ORF1* is not predicted to be transcribed from the putative –35 and –10 promoter of the pdc operon.

Based on the above studies, the S. ventriculi pdc gene was determined to encode a polypeptide of 552 amino acids (including the N-terminal methionine) with a calculated pI of 5.16 and anhydrous molecular mass of 61,737 Da. GenBank accession number AF354297 has been assigned to the Sarcina ventriculi sequence.

Example 4

Methods for Producing an Antibody that Specifically Binds a PDC Polypeptide

In this example, methods for making an immunospecific antibody against a pyruvate decarboxylase are described.

In brief, purified recombinant A. pasteurians PDC polypeptide (300 μg) was separated by SDS-PAGE. A gel fragment containing the PDC protein was excised prior to staining with Coomassie blue R-250. This was used as antigen for polyclonal antibody production in rabbits (anti-ApPDC) as recommended by the supplier (Cocalico Biologicals, Reamstown, Pa.). For immunoblot analysis, proteins were separated by SDS-PAGE and transferred to PVDF membranes in 10 mM MES at pH 6.0 with 10% methanol for 16 h at 20 volts at 4° C. For detection of antigen, immunoblot procedures and colorimetric detection were using standard techniques. The primary antibody, anti-ApPDC, was diluted 1:7,000. The alkaline phosphatase linked goat anti-rabbit secondary antibody (Fisher Biotech) was diluted 1:7,500. Using the foregoing method, a polyclonal antisera that specifically bound a PDC polypeptide was identified.

If desired, the antibody molecules directed against PDC can be isolated from the mammal (e.g., from the blood) and further purified by well known techniques, such as protein A chromatography to obtain the IgG fraction. In addition, at an appropriate time after immunization, e.g., when the anti-PDC antibody titers are highest, antibody-producing cells can be obtained from the subject and used to prepare monoclonal antibodies by standard techniques, such as the hybridoma technique originally described by Kohler and Milstein (1975) Nature 256:495-497; see also, e.g., Using Antibodies: A Laboratory Manual, Harlow et al., C.S.H.L. Press, Pub. (1999)).

Example 5

Methods for Identifying Codon Usage of PDC Genes in Different Host Cells

In this example, methods for identifying PDC polypeptides suitable for improved expression based on codon usage are described.

Bacterial PDC can be used to engineer ethanol pathways in a wide variety of organisms. However, compatible patterns of codon usage are advantageously determined in order to ensure for functional expression in heterologous systems (4, 14, 16, 22). A simple tabulation of G+C content can serve as an initial guide. G+C contents for these four pdc genes range from 60% for *A. pasteurians* to 31% for *S. ventriculi*. The average G+C content for *E. coli* ORFs is 52%, identical to that for *Z. mobilis* pdc (52%) and similar to *Z. palmae* pdc (55%). For most amino acids, patterns of codon usage for these two organisms were quite similar to each other and to *E. coli*. The *Z. palmae* pdc was functionally expressed at high levels (approximately ⅓ of polypeptide based on activity) in recombinant *E. coli*. The *Z. mobilis* pdc and *A. pasteurianus* pdc were expressed at lower levels (7 to 9% of polypeptide based on activity) and *S. ventriculi* pdc was poorly expressed in recombinant *E. coli* (less than 0.3% of polypeptide based on activity)(45).

To produce larger amounts of functional recombinant *S. ventriculi* PDC, the use of a modified *E. coli* host containing additional tRNA genes for rare codons such as AGA (arginine), GGA (glycine), AUA (isoleucine), and CUA (leucine) proved important for high-level polypeptide production (almost ¼ of polypeptide based on activity) (45). The pattern of codon usage in *S. ventriculi* pdc is particularly useful for the genetic engineering of an ethanol pathway in low G+C Gram-positive bacteria as illustrated by the comparison to *B. subtilis* ORFs (Table 1). In contrast, *A. pasteurians* pdc can be selected for engineering a homoethanol pathway in to high G+C cellulolytic bacteria such as Thermobifidia sp. (23) or Cellulomonas sp. (35).

TABLE 1

Codon Usage of Bacterial pdc Genes

| Amino Acid | Codon | Zpa pdc* | Apa pdc* | Zmo pdc* | Sve pdc* | Eco K-12 genome[†] | Bsu genome[†] |
|---|---|---|---|---|---|---|---|
| Ala | GCA | 41.3 (32) | 17.9 (14) | 31.6 (21) | 32.5 (47) | 20.1 (21) | 21.7 (28) |
|  | GCC | 39.5 (30) | 73.5 (56) | 31.6 (21) | 0 (—) | 25.5 (27) | 15.8 (21) |
|  | GCG | 3.6 (03) | 30.5 (23) | 10.5 (07) | 1.8 (03) | 33.6 (36) | 20.2 (26) |
|  | GCU | 46.7 (36) | 9.0 (07) | 75.6 (51) | 34.4 (50) | 15.3 (16) | 19.0 (25) |
| Arg | AGA | 0 (—) | 0 (—) | 0 (—) | 39.8 (100) | 2.1 (04) | 10.6 (26) |
|  | AGG | 0 (—) | 1.8 (04) | 0 (—) | 0 (—) | 1.2 (02) | 3.9 (09) |
|  | CGC | 23.3 (50) | 28.7 (64) | 14.1 (47) | 0 (—) | 22.0 (40) | 8.6 (21) |
|  | CGG | 0 (—) | 5.4 (12) | 1.8 (06) | 0 (—) | 5.4 (10) | 6.5 (16) |
|  | CGU | 23.3 (50) | 9.0 (20) | 14.1 (47) | 0 (—) | 20.9 (38) | 7.6 (18) |
|  | CGA | 0 (—) | 0 (—) | 0 (—) | 0 (—) | 3.6 (07) | 4.1 (10) |
| Asn | AAC | 41.3 (77) | 32.3 (67) | 49.2 (82) | 19.9 (42) | 21.7 (55) | 17.3 (44) |
|  | AAU | 12.6 (23) | 16.1 (33) | 10.5 (18) | 27.1 (58) | 17.7 (45) | 22.1 (56) |
| Asp | GAC | 37.7 (78) | 32.3 (67) | 22.8 (54) | 3.6 (07) | 19.1 (37) | 18.8 (36) |
|  | GAU | 10.8 (22) | 16.1 (33) | 19.3 (46) | 47.0 (93) | 32.1 (63) | 33.0 (64) |
| Cys | UGC | 10.8 (60) | 32.3 (67) | 10.5 (85) | 1.8 (20) | 6.5 (56) | 4.3 (55) |
|  | UGU | 7.2 (40) | 16.1 (33) | 1.8 (15) | 7.2 (80) | 5.2 (44) | 3.6 (45) |
| Gln | CAA | 9.0 (25) | 3.6 (11) | 0 (—) | 28.9 (100) | 15.3 (35) | 19.8 (51) |
|  | CAG | 26.9 (75) | 28.7 (89) | 17.6 (100) | 0 (—) | 28.8 (65) | 18.7 (49) |
| Glu | GAA | 61.0 (87) | 43.0 (80) | 63.3 (92) | 85.0 (94) | 39.4 (69) | 48.9 (68) |
|  | GAG | 9.0 (13) | 10.8 (20) | 5.3 (08) | 5.4 (06) | 17.8 (31) | 23.1 (32) |
| Gly | GGA | 1.8 (02) | 3.6 (05) | 1.8 (02) | 50.6 (72) | 8.0 (11) | 21.7 (31) |
|  | GGC | 35.9 (44) | 64.5 (82) | 19.3 (24) | 0 (—) | 29.6 (40) | 23.4 (34) |
|  | GGG | 0 (—) | 3.6 (05) | 0 (—) | 0 (—) | 11.1 (15) | 11.2 (16) |
|  | GGU | 44.9 (54) | 7.2 (09) | 59.8 (74) | 19.9 (28) | 24.7 (34) | 12.8 (19) |
| His | CAC | 14.4 (67) | 10.8 (43) | 12.3 (58) | 3.6 (22) | 9.7 (43) | 7.5 (33) |
|  | CAU | 7.2 (33) | 14.3 (57) | 8.8 (42) | 12.7 (78) | 12.9 (57) | 15.2 (67) |
| Ile | AUA | 0 (—) | 0 (—) | 0 (—) | 39.8 (56) | 4.4 (07) | 9.3 (13) |
|  | AUC | 55.7 (89) | 34.1 (66) | 36.9 (78) | 9.0 (13) | 25.1 (42) | 27.0 (37) |
|  | AUU | 7.2 (11) | 17.9 (34) | 10.5 (22) | 21.7 (31) | 30.3 (51) | 36.8 (50) |
| Leu | CUA | 7.2 (09) | 0 (—) | 0 (—) | 7.2 (09) | 3.9 (04) | 4.9 (05) |
|  | CUC | 5.4 (07) | 9.0 (08) | 19.3 (22) | 0 (—) | 11.1 (10) | 10.8 (11) |
|  | CUG | 59.2 (73) | 69.9 (64) | 33.4 (38) | 0 (—) | 52.6 (50) | 23.1 (24) |
|  | CUU | 3.6 (04) | 10.8 (10) | 15.8 (18) | 14.5 (18) | 11.0 (10) | 23.0 (24) |
|  | UUA | 0 (—) | 0 (—) | 1.8 (02) | 59.7 (73) | 13.9 (13) | 19.1 (20) |
|  | UUG | 5.4 (07) | 19.3 (18) | 17.6 (20) | 0 (—) | 13.7 (13) | 15.3 (16) |
| Lys | AAA | 26.9 (94) | 12.5 (35) | 35.1 (56) | 63.3 (92) | 33.6 (76) | 49.1 (70) |
|  | AAG | 1.8 (06) | 23.3 (65) | 28.1 (44) | 5.4 (08) | 10.3 (24) | 20.8 (30) |
| Met | AUG | 26.9 (100) | 26.9 (100) | 21.0 (100) | 27.1 (100) | 27.9 (100) | 26.9 (100) |
| Phe | UUC | 23.3 (87) | 19.7 (78) | 28.1 (89) | 18.1 (38) | 16.6 (43) | 14.2 (32) |
|  | UUU | 3.6 (13) | 5.4 (22) | 3.5 (11) | 28.9 (62) | 22.3 (57) | 30.2 (68) |
| Pro | CCA | 1.8 (04) | 1.8 (04) | 5.3 (11) | 18.1 (67) | 8.4 (19) | 7.0 (19) |
|  | CCC | 1.8 (04) | 21.5 (50) | 3.5 (07) | 0 (—) | 5.5 (12) | 3.3 (09) |
|  | CCG | 30.5 (74) | 14.3 (33) | 28.1 (59) | 1.8 (07) | 23.2 (53) | 16.1 (44) |
|  | CCU | 7.2 (17) | 5.4 (13) | 10.5 (22) | 7.2 (27) | 7.0 (16) | 10.6 (29) |
| Ser | AGC | 12.6 (26) | 19.7 (35) | 15.8 (37) | 12.7 (20) | 16.1 (28) | 14.2 (23) |
|  | AGU | 1.8 (04) | 0 (—) | 5.3 (13) | 12.7 (20) | 8.8 (15) | 6.6 (10) |
|  | UCA | 3.6 (07) | 7.2 (13) | 1.8 (04) | 32.5 (50) | 7.2 (12) | 14.8 (23) |
|  | UCC | 9.0 (19) | 19.7 (35) | 14.1 (33) | 0 (—) | 8.6 (15) | 8.1 (13) |
|  | UCG | 1.8 (04) | 7.2 (13) | 0 (—) | 0 (—) | 8.9 (15) | 6.4 (10) |
|  | UCU | 19.7 (41) | 1.8 (03) | 5.3 (13) | 7.2 (11) | 8.5 (15) | 12.9 (21) |

TABLE 1-continued

Codon Usage of Bacterial pdc Genes

| Amino Acid | Codon | Zpa pdc* | Apa pdc* | Zmo pdc* | Sve pdc* | Eco K-12 genome† | Bsu genome† |
|---|---|---|---|---|---|---|---|
| Thr | ACA | 5.4 (09) | 10.8 (16) | 0 (—) | 34.4 (53) | 7.1 (13) | 22.3 (41) |
|  | ACC | 19.7 (34) | 30.5 (45) | 28.1 (62) | 0 (—) | 23.4 (43) | 8.6 (16) |
|  | ACG | 10.8 (19) | 23.3 (34) | 10.5 (23) | 0 (—) | 14.4 (27) | 14.6 (27) |
|  | ACU | 21.5 (38) | 3.6 (05) | 7.0 (15) | 30.7 (47) | 9.0 (17) | 8.7 (16) |
| Trp | UGG | 16.2 (100) | 12.5 (100) | 12.3 (100) | 5.4 (100) | 15.2 (100) | 10.3 (100) |
| Tyr | UAC | 18.0 (59) | 14.3 (47) | 12.3 (32) | 7.2 (18) | 12.2 (43) | 12.0 (35) |
|  | UAU | 12.6 (41) | 16.1 (53) | 26.4 (68) | 32.5 (82) | 16.2 (57) | 22.6 (65) |
| Val | GUA | 14.4 (20) | 7.2 (10) | 0 (—) | 36.2 (46) | 10.9 (15) | 13.4 (20) |
|  | GUC | 34.1 (49) | 23.3 (32) | 31.6 (40) | 0 (—) | 15.3 (22) | 17.3 (26) |
|  | GUG | 3.6 (05) | 26.9 (38) | 5.3 (07) | 0 (—) | 26.4 (37) | 17.7 (26) |
|  | GUU | 18.0 (26) | 14.3 (20) | 42.2 (53) | 43.4 (54) | 18.3 (26) | 19.2 (28) |
| Coding DNA mol % G + C |  | 55 | 60 | 52 | 31 | 52 | 44 |

Codon usage for pdc (*) and genomic DNA (†) represented as frequency per thousand bases. Percent codon usage per amino acid indicated in parentheses. Stop codons are not included. Abbreviations (Genbank accession number): Apa, *A. pasteurianus* pdc (AF368435) Zpa, *Z. palmae* pdc (AF474145); Zmo, *Z. mobilis* (M15393); Sve, *S. ventriculi* (AF354297); Eco, *E. coli*; Bsu, *B. subtilis*.

Example 6

Biochemical Characterization of PDC Activity

In this example, the biochemical characterization of several representative PDC polypeptides is described.

The purification of four representative bacterial PDC polypeptides was performed as presented in Table 2, infra. ZpaPDC was purified to homogeneity from *Z. palmae* and recombinant *E. coli*. For comparison, three other bacterial PDCs were purified from recombinant *E. coli*. PDC was also purified from *A. pasteurians*. In general, purification of the 'native' PDCs required additional steps (i.e., phenyl Sepharose and hydroxyapatite chromatography). This was due to the 10- to 250-fold lower levels of PDC activity of 'native' compared to 'recombinant' cell lysate. All of the PDC polypeptides had subunit molecular masses of 55 to 60 kDa, as estimated by reducing SDS-PAGE, which were consistent with the masses calculated from the deduced polypeptide sequences.

The N-terminal amino acid sequence of PDC purified from *Z. palmae* (MYTVGMYLAE) was identical to the sequence deduced from the gene and included the N-terminal methionine. Previous studies have demonstrated that the PDC purified from *S. ventriculi* also retains the N-terminal methionine which is amino to a lysine residue (28, 45). In contrast, the N-terminal sequence of PDC purified from *A. pasteurianus* (TYTVGMYLAERL) lacked an N-terminal methionine indicating that cleavage by a native methionine aminopeptidase. The PDC purified from *Z. mobilis* also was determined to be cleaved to expose an N-terminal serine (34). These results are consistent with the highly conserved substrate specificity of methionine aminopeptidases which is dictated by the $P_1'$ residue (5). The N-terminal methionine is only removed if the second residue is small and uncharged. This substrate preference is opposite to the 'N-end rule' for polypeptide degradation (47).

A determination of the quaternary structure of the PDC polypeptides was also performed. The ZmoPDC associates as a tetramer of 240 kDa even after removal of the cofactors TPP and $Mg^{2+}$ (15). Likewise the SvePDC and ZpaPDC associated as tetramers of 240 kDa even after cofactor dissociation (data not shown). Interestingly, the ApaPDC formed both tetramers and octamers (224 and 447 kDa) of similar specific activity, and dissociated into dimers (120 kDa) after cofactor extraction. Activity and tetrameric configuration of the ApaPDC apoenzyme were fully restored after addition of $Mg^{2+}$ and TPP with half saturation constants of 3.1 μM and 5.8 μM and Hill constants of 1.17 to 1.22, respectively. The tetrameric configuration observed for all four bacterial PDCs is consistent with the quaternary structure of the majority of eukaryotic PDCs. However, similar to ApaPDC higher order structures have been observed for the PDC from the filamentous fungus *Neurospora crassa*, which associates as a homopolymeric filament of 8 to 10 nm (1). Likewise, in plants (maize, pea, and wheat germ) PDC forms complexes up to 1 MDa (24, 27, 32). The dissociation of ApaPDC into dimers after removal of the cofactors is also consistent with eukaryotic PDCs (25).

TABLE 2

Purification of Bacterial PDC Polypeptides.

| Purification Step | Sp. Activity (U mg$^{-1}$) | Purification Fold |
|---|---|---|
| ZpaPDC |  |  |
| Lysate | 0.13 | 1 |
| Q-Sepharose | 1.3 | 10 |
| (Phenyl Sepharose) | 66 | 510 |
| ZpaPDC-R |  |  |
| Lysate | 32 | 1 |
| Q-Sepharose | 92 | 3 |
| (Superdex 200) | 100 | 4 |
| ApaPDC |  |  |
| Lysate | 0.62 | 1 |
| Q-Sepharose | 12 | 18 |
| (Hydroxyapatite) | 71 | 110 |
| ApaPDC-R |  |  |
| Lysate | 6.7 | 1 |
| Q-Sepharose | 58 | 9 |
| (Superdex 200) | 92 | 14 |
| ZmoPDC-R |  |  |
| Lysate | 6.2 | 1 |
| Q-Sepharose | 57 | 9 |
| (Superdex 200) | 72 | 12 |

TABLE 2-continued

Purification of Bacterial PDC Polypeptides.

| Purification Step | Sp. Activity (U mg$^{-1}$) | Purification Fold |
|---|---|---|
| SvePDC-R | | |
| Lysate | 8.7 | 1 |
| Q-Sepharose | 33 | 2 |
| (Superdex 200) | 37 | 6 |

PDC-R, PDC purified from recombinant E. coli. SvePDC-R represents polypeptide purified from E. coli Rosetta(DE3)(pRARE, pJAM419). Sve-PDC-R activity was not detected in cell lysate of E. coli BL21-CodonPlus-RIL(pJAM419). Parentheses indicate final purification step. Q-Sepharose and Superdex 200 were common purification steps for all of the bacterial PDCs.

Example 7

Characterization of PDC Thermostability

In this example, the thermostability of several representative PDC polypeptides is described.

Figure 7:
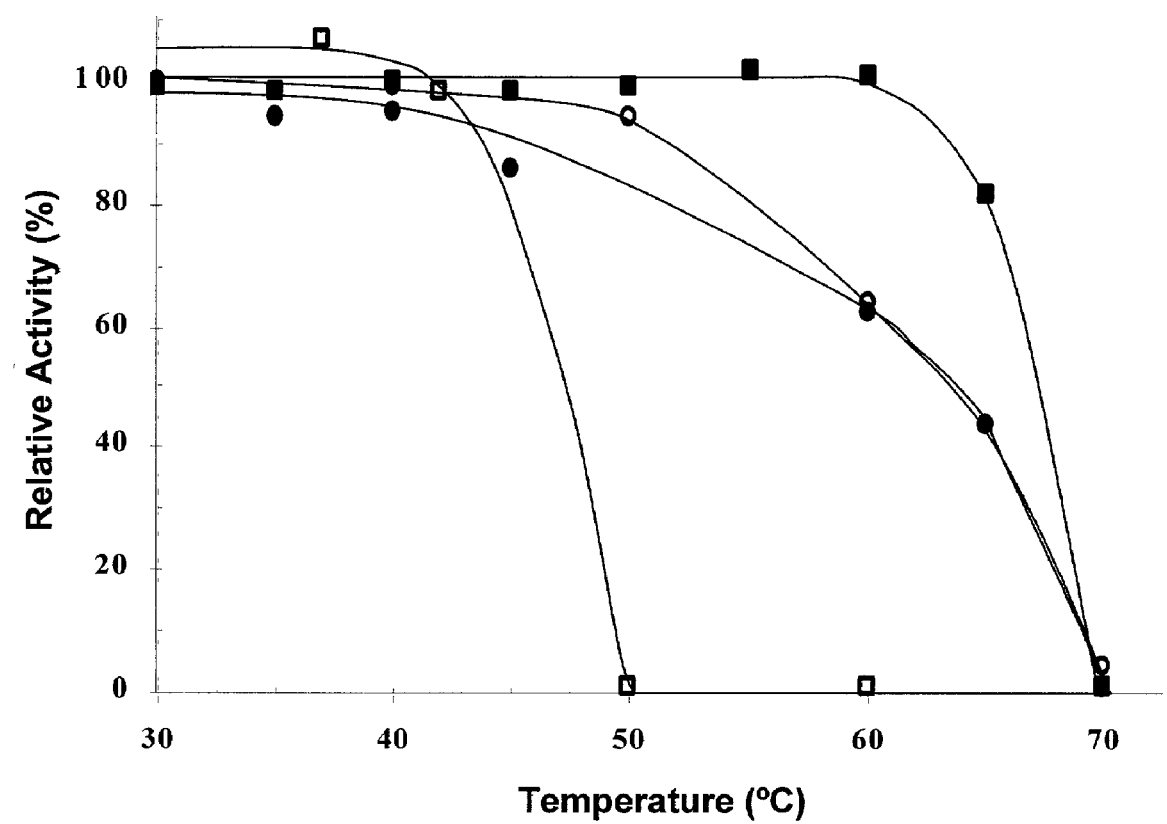
FIG. 7 shows a graph depicting the thermostability of different bacterial PDC enzymes. 'Recombinant' Zmo (●), Zpa (■), Apa (○) and Sve (□) PDC polypeptides were pre-incubated at the temperatures indicated in 50 mM sodium citrate buffer at pH 5.0 with 1 mM TPP and 1 mM $MgCl_2$ for 30 min, cooled to 0° C., and assayed for residual activity at 25° C. in the same buffer. 100% is activity after pre-incubated at 0° C. SvePDC was purified from recombinant *E. coli* BL21-CodonPlus-RIL (pJAM419).

It has been observed that the ZmoPDC is thermostable after heating cell lysate to 60° C. in the presence of cofactors (TPP and Mg$^{2+}$) (11). To further address this phenomenon, activity of the purified bacterial PDCs was analyzed at 25° C. after exposure to various temperatures in the presence of saturating cofactors (FIG. 7). All three Gram-negative PDCs were relatively thermostable and retained 60 to 100% activity after heating to 60° C. for 30 min. In contrast, the purified SvePDC was completely inactivated after exposure to temperatures of 50° C. or higher. Although amino acid composition cannot be used as a universal guide to thermostability (30, 31, 48), it was observed that the three thermostable PDCs contained higher levels of alanine and cysteine and lower levels of phenylalanine. These changes are consistent with an increase in thermostability based on compositional comparisons of homologous enzymes (2, 31). Increased levels of alanine can stabilize Gram-negative PDC polypeptides at high temperature by facilitating the formation of helices and a more compact polypeptide core. Accordingly, the present invention also includes pdc genes which have been altered to express a PDC polypeptide comprising corresponding cysteine and/or alanine amino acid changes to achieve improved thermostability. In addition, analysis of the thermostable PDCs from the Gram-negative bacteria revealed an over 2.5-fold increase in activity when assayed at their temperature optima of 60° C. compared to room temperature. Based on Arrhenius plots, these enzymes were estimated to have activation enthalpy in the range of 12.6 to 14.2 kJ mol$^{-1}$ and entropy values of −92.8 to −98.2 J mol$^{-1}$ K$^{-1}$.

Example 8

Characterization of PDC Substrate Affinities and pH Optima

In this example, the characterization of substrate affinity for several representative PDC polypeptides as well as pH optima are described.

Figure 8:
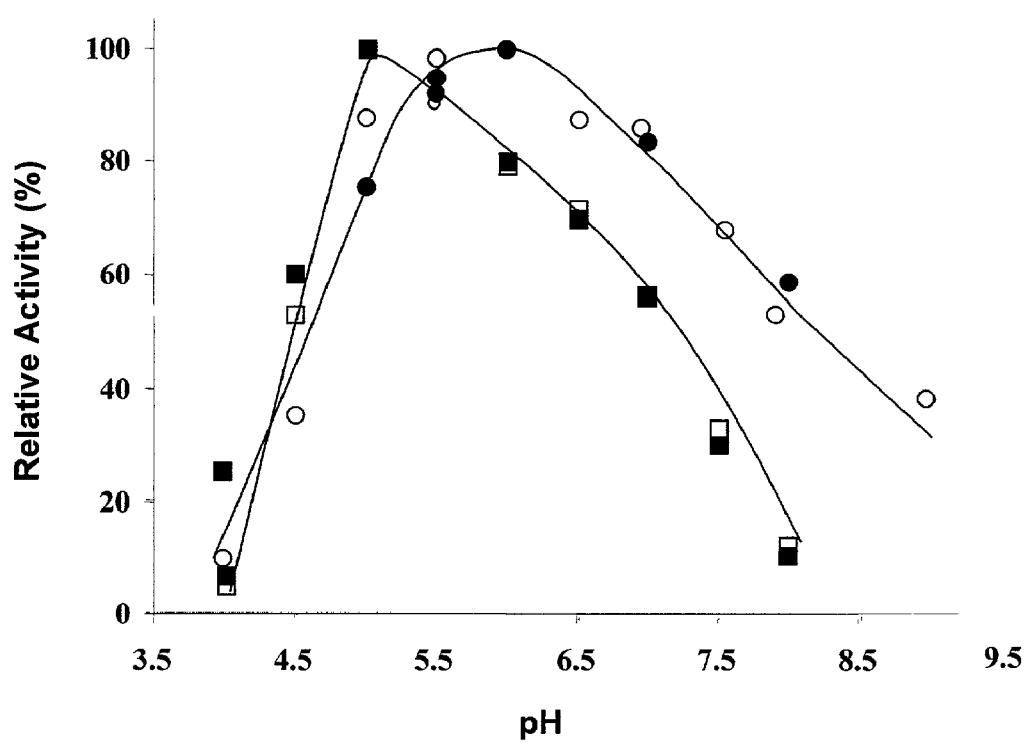
FIG. 8 shows a graph depicting the effect of pH on the activity of bacterial PDC enzymes. 'Recombinant' ZpaPDC (●) and ApaPDC (■). 'Native' ZpaPDC (○) and ApaPDC (□). Activity was measured at 25° C. in 50 mM sodium citrate buffer from pH 4.0 to 5.0 and 50 mM sodium phosphate buffer from pH 5.5 to pH 8.0. 100% is activity at optimal pH.

In particular, significant differences in pH optima were observed for the bacterial PDC polypeptides. The ZpaPDC was most active at pH 5.5 to 6.0 (FIG. 8), similar to ZmoPDC which has a pH optimum of 6.0 (34). The pH optimum of ApaPDC, however, was significantly lower than that observed for the other two Gram-negative PDCs and ranged from 5.0 to 5.5 (FIG. 8). The pH optimum for the Gram-positive SvePDC (pH 6.3 to 7.6) has been shown to be much broader and more neutral than the Gram-negative PDCs (28). This indicates that there are differences in the conformation and/or composition of charged residues at or near the active site.

The eukaryotic and bacterial SvePDC exhibit positive cooperative kinetics in the presence of the substrate pyruvate (9, 25, 28). The ZpaPDC and ApaPDC, however, exhibited normal Michaelis-Menten kinetics with $K_m$ values of 0.2 to 0.4 mM for pyruvate and $k_{cat}$ values of 20,500 to 30,500 min$^{-1}$ (pH optimum, 25° C.) (Table 3). The lack of allosteric control with respect to pyruvate, which was observed for these Gram-negative PDC enzymes, is similar to that established for the highly related PDC from Z. mobilis (7, 34). As a further comparison, the kinetic constants of all four bacterial PDC polypeptides were determined at their pH optimum as well as at pH 7.0 (Table 3). This approach was chosen to analyze the bacterial PDC enzymes to more closely reflect the neutral cytosol of recombinant hosts used previously for high-level ethanol production (e.g. E. coli, Erwinia spp.). These modest pH changes had only a slight effect on the maximum rate of the reaction for all four bacterial PDC polypeptides. In contrast, pH significantly influenced the affinity of the Gram-negative PDCs for pyruvate. Most notably, an over 13-fold increase in $K_m$ was observed when ApaPDC was shifted from its pH optimum to neutral conditions.

TABLE 3

Kinetic Parameters of Recombinant Bacterial PDC Enzymes.

| Parameters | ZpaPDC | ApaPDC | ZmoPDC | SvePDC |
|---|---|---|---|---|
| Type of kinetics | N | N | N | S |
| pH optimum | 5.5–6.0 | 5.0–5.5 | 6.0 | 6.3–6.7 |
| $K_m$ (pH) | 0.24 (6.0) | 0.39 (5.0) | 0.43 (6.0) | 5.7 (6.5) |
|  | 0.71 (7.0) | 5.1 (7.0) | 0.94 (7.0) | 4.0 (7.0) |
| $V_{max}$ (pH) | 130 (6.0) | 97 (5.0) | 100 (6.0) | 45 (6.5) |
|  | 140 (7.0) | 79 (7.0) | 78 (7.0) | 35 (7.0) |

Abbreviations: N, normal Michaelis-Menten kinetics; S, sigmoidal kinetics. SvePDC was purified from E. coli Rosetta(DE3)(pRARE, pJAM419).

These results indicate that all three Gram-negative PDCs have an amino acid residue(s) that enables the enzyme to more efficiently bind pyruvate when protonated (at the pH optimum) than deprotonated (neutral pH). However, the protonated state of this residue does not influence the overall rate of decarboxylation. Because the changes in $K_m$ for the Gram-negative PDCs were observed between pH values of 5 to 7, it is possible that the residue involved in modulating substrate binding for all three enzymes is a histidine. The $pK_a$ for free histidine is 6.04; whereas, the $pK_a$ for pyruvate as well as the other ionizable amino acid residues (i.e. Asp, Glu, Lys, and Arg) does not fall within this pH range.

Protonation of one or more histidines is important to facilitate substrate binding by forming an ion pair with the carboxyl group of pyruvate or by making the active site more substrate accessible. It is also possible that a different residue(s) is involved modulating substrate binding; however, its $pK_a$ is modified by the polypeptide environment.

The effect of pH on $k_{cat}/K_m$ compared to $k_{cat}$ for the PDC enzyme of Z. mobilis was determined using titration curves with $pK_a$ values estimated at 6.23 to 6.45 for the residue involved in modulating substrate binding (21, 43). The deprotonation of His113 has been indicated to lead to conformational changes that result in a flexible loop (residues 105 to 112) to close over the active site during catalysis (43). Both His113 and His114 are conserved in all PDC polypeptides that have been characterized. Thus, His113 is a logical candidate for the observed pH-dependent changes in $K_m$ observed for all three Gram-negative PDCs. However, five crucial residues with ionizable side-chains protruding into the active site of Z. mobilis PDC (Asp27, Glu50, His113, His114, and Glu473) were modified to residues that were non-ionizable or had altered $pK_a$ values (21). The pH-dependence of $k_{cat}/K_m$ was relatively unaffected by these modifications indicating that these residues, including His113, is not involved. Importantly, in this same study modification of His113 to a residue with significantly higher $pK_a$ value (i. e. Arg and Lys) increased the affinity of ZmoPDC for pyruvate by over 20-fold.

These results show that the positively charged form of His113 keeps the active site open for substrate binding.

Example 9

Comparison alignment of PDC Genes from Different Organisms

In this example, a comparison alignments of the amino acid sequences of pyruvate decarboxylase enzymes (PDC) from different organisms are compared and contrasted.

The deduced PDC polypeptide of Z. palmae (ZpaPDC) contained 556 amino acids (including the N-terminal methionine) with an anhydrous molecular mass of . 60,113 Da. This is similar to the three other bacterial PDCs which range from 552 to 568 amino acids and 59,830 to 61,809 Da. The ZpaPDC had a calculated pI of 4.93 analogous to the pI determined experimentally (4.87 to 5.3) for the Z. mobilis PDC (7, 33). The relatively high alanine content of ZpaPDC (13.1%) was comparable to that of the Gram-negative Z. mobilis and A. pasteurians PDCs (Zmo and ApaPDC) but almost 2-fold higher than that of the Gram-positive S. ventriculi PDC (SvePDC) (6.9%). Multiple amino acid sequence alignment (FIG. 9) and dendrogram cluster analysis revealed that ZpaPDC was most closely related to ApaPDC (72% identity) and highly related to ZmoPDC (62% identity). All three of the Gram-negative PDCs clustered in sequence similarity with the plant PDCs (e.g. Zea mays PDC; 39 to 40% identity).

In contrast, the Gram-positive SvePDC was only 30 to 31% identical to the Gram-negative PDCs and instead grouped with the majority of filamentous fungi and yeast PDCs (e.g. Saccharomyces cerevisiae PDC1; 38% identity). The N-terminal extension common to PDCs of the plant kingdom was absent from all four of the bacterial PDCs. Residues involved in TPP and $Mg^{2+}$ binding, based on the crystal structures of the Z. mobilis and yeast PDCs, were conserved in all four bacterial PDCs. In contrast, residues of the yeast PDC1 (Tyr157 and Arg224) are involved in substrate activation, based on binding to the pyruvate analog pyruvamide (29), were only noted in the bacterial SvePDC and not found in the remaining three bacterial PDCs.

The deduced A. pasteurians PDC amino acid sequence was aligned with PDC sequences from Z. mobilis and yeast (PDC1), both of which have been analyzed by x-ray crystallography (Dyda et al., 1993; Arjunan et al., 1996; Lu et al., 2000; Dobritzsch et al., 1998), as well as from Zea mays (FIG. 9). The multiple alignments revealed that the A. pasteurians PDC is most similar to Z. mobilis PDC (62% identity and 74% similarity). The N-terminal extension of the Z. mays PDC, common to other plant PDCs, is not found in the fungal or bacterial PDC polypeptides including that of A. pasteurianus. Residues demonstrated to be within 0.4 nm of the TPP and $Mg^{2+}$ binding sites of the yeast and Z. mobilis PDC enzymes were highly conserved in the A. pasteurianus PDC polypeptide sequence (V24, D27, E50, T72, V75, N82, H113, H114, T384, D386. G408, I410, D435, S437, L440, I460, N462, G464, I467, E468). In addition, the motif identified in TPP-dependent enzymes which was proposed by Hawkins et al. (1989) to be involved in $Mg^{2+}$ and TPP binding is also conserved in the A. pasteurians PDC polypeptide sequence (G435 to N462). Residues of the yeast PDC1 (Tyr157 and R224) proposed to be involved in allosteric control and demonstrated to bind the pyruvate analog pyruvamide (Lu et al., 2000), were not conserved in the A. pasteurians, Z. mobilis, or Z. mays PDC polypeptides. Instead these residues are restricted to the majority of fungal PDCs and related PDC polypeptide from the Gram-positive bacterium S. ventriculi which is substrate activated (Lowe and Zeikus, 1992). Based on the kinetics of $CO_2$ production from pyruvate observed for cell lysate of acetic acid bacteria (King and Cheldelin, 1953), it is concluded that the A. pasteurianus PDC polypeptide, similar to the Z. mobilis PDC, is not substrate activated. However, the plant PDCs do not contain these conserved residues but are regulated by substrate, indicating some differences in the mechanism of allosteric control among PDC polypeptides.

Based on cluster analysis of PDC polypeptides, the A. pasteurians PDC is most closely related to the Z. mobilis PDC. This is consistent with the classification of these two bacteria as Gram-negative oc-proteobacteria. In contrast to the low G+C Gram-positive S. ventriculi PDC which shares close evolutionary roots with the majority of fungal PDCs, the PDC polypeptides from the α-proteobacteria are more closely related to plant and a couple of out-grouping fungal PDCs.

Equivalents

Those skilled in the art will recognize, or be able to ascertain using no more than routine experimentation, many equivalents to the specific embodiments of the invention described herein. Such equivalents are intended to be encompassed by the following claims. Moreover, any number of genetic constructs, host cells, and methods described in U.S. Pat. Nos. 5,821,093; 5,482,846; 5,424,202; 5,028, 539; 5,000,000; 5,487,989, 5,554,520, and 5,162,516, can be employed in carrying out the present invention and are hereby incorporated by reference.

LITERATURE CITED

1. Alvarez, M. E., A. L. Rosa, E. D. Temporini, A. Wolstenholme, G. Panzetta, L. Patrito, and H. J. Maccioni. 1993. The 59-kDa polypeptide constituent of 8-10-nm cytoplasmic filaments in Neurospora crassa is a pyruvate decarboxylase. Gene 130:253-258.
2. Argos, P., M. G. Rossman, U. M. Grau, H. Zuber, G. Frank, and J. D. Tratschin. 1979. Thermal stability and polypeptide structure. Biochemistry 18:5698-5703.
3. Atkinson, D. E. 1956. Hydrogen metabolism in Acetobacter peroxydans.J. Bacteriol. 72:189-194.
4. Barbosa, M. F. S. and L. O. Ingram. 1994. Expression of the Zymomonas mobilis alcohol dehydrogenase II (adhB) and pyruvate decarboxylase (pdc) genes in Bacillus. Curr. Microbiol. 28:279-282.
5. Bradshaw, R. A., W. W. Brickey, and K. W. Walker. 1998. N-terminal processing:

the methionine aminopeptidase and N<sup>α</sup>-acetyl transferase families. Trends Biochem. Sci. 23:263-267.
6. Braü, B. and H. Sahm. 1986. Cloning and expression of the structural gene for pyruvate decarboxylase of *Zymomonas mobilis* in *Escherichia coli*. Arch. Microbiol. 144:296-301.
7. Bringer-Meyer, S., K.-L. Schimz, and H. Sahm. 1986. Pyruvate decarboxylase from *Zymomonas mobilis*. Isolation and partial characterization. Arch. Microbiol. 146: 105-110.
8. Bucher, M., R. Braendle, and C. Kuhlemeier. 1994. Ethanolic fermentation in transgenic tobacco expressing *Zymomonas mobilis* pyruvate decarboxylase. EMBO J. 13:2755-2763.
9. Candy, J. M. and R. G. Duggleby. 1998. Structure and properties of pyruvate decarboxylase and site-directed mutagenesis of the *Zymomonas mobilis* enzyme. Biochim. Biophys. Acta 1385:323-338.
10. Candy, J. M., R. G. Duggleby, and J. S. Mattick. 1991. Expression of active yeast pyruvate decarboxylase in *Escherichia coli*. J. Gen. Microbiol. 137:2811-2815.
11. Conway, T., Y. A. Osman, J. I. Konnan, E. M. Hoffmann, and L. O. Ingram. 1987. Promoter and nucleotide sequences of the *Zymomonas mobilis* pyruvate decarboxylase. J. Bacteriol. 169:949-954.
12. Corpet, F. 1988. Multiple sequence alignment with hierarchical clustering. Nucleic Acids Res. 16:10881-10890.
13. DeLey, J. 1958. Studies on the metabolism of *Acetobacter peroxydans*. Part I. General properties and taxonomic position of the species. Antonie Van Leeuwenhoek J. Microbiol. Serol. 24:281-297.
14. Deng, M. D. and J. R. Coleman. 1999. Ethanol synthesis by genetic engineering in cyanobacteria. Appl. Environ. Microbiol. 65:523-528.
15. Diefenbach, R. J. and R. G. Duggleby. 1991. Pyruvate decarboxylase from *Zymomonas mobilis*. Structure and re-activation of apoenzyme by the cofactors thiamin diphosphate and magnesium ion. Biochem. J. 276:439-445.
16. Gold, R. S., M. M. Meagher, S. Tong, R. W. Hutkins, and T. Conway. 1996. Cloning and expression of the *Zymomonas mobilis* "production of ethanol" genes in *Lactobacillus casei*. Curr. Microbiol. 33:256-260.
17. Harwood, C. R. and S. M. Cutting. 1990. In Molecular Biological Methods for Bacillus. Wiley, New York.
18. Hénaut, A. and A. Danchin. 1996. Analysis and predictions from *Escherichia coli* sequences, or *E. coli* in silico, p. 2047-2066. In F. C. Neidhardt and et al. (eds.), *Escherichia coli* and Salmonella Cellular and Molecular Biology. ASM Press, Washington, D.C.
19. Hoppner, T. C. and H. W. Doelle. 1983. Purification and kinetic characteristics of pyruvate decarboxylase and ethanol dehydrogenase from *Zymomonas mobilis* in relation to ethanol production. Eur. J. Appl. Microbiol. Biotechnol. 17:152-157.
20. Horn, S. J., I. M. Aasen, and K. Østgaard. 2000. Production of ethanol from mannitol by *Zymobacter palmae*. J. Indust. Microbiol. Biotech. 24:51-57.
21. Huang, C. Y., A. K. Chang, P. F. Nixon, and R. G. Duggleby. 2001. Site-directed mutagenesis of the ionizable groups in the active site of *Zymomonas mobilis* pyruvate decarboxylase: effect on activity and pH dependence. Eur. J. Biochem. 268:3558-3565.
22. Ingram, L. O., H. C. Aldrich, A. C. Borges, T. B. Causey, A. Martinez, F. Morales, A. Saleh, S. A. Underwood, L. P. Yomano, S. W. York, J. Zaldivar, and S. Zhou. 1999. Enteric bacterial catalysts for fuel ethanol production. Biotechnol. Prog. 15:855-866.
23. Irwin, D. C., S. Zhang, and D. B. Wilson. 2000. Cloning, expression and characterization of a Family 48 exocellulase, Cel48A, from *Thermobifida fusca*. Eur. J. Biochem. 267:4988-4997.
24. Kenworthy, P. and D. D. Davies . 1976. Kinetic aspects of regulation of pyruvic decarboxylase. Phytochemistry 15:279-282.
25. König, S. 1998. Subunit structure, function and organisation of pyruvate decarboxylases from various organisms. Biochim.Biophys.Acta 1385:271-286.
26. Laemmli, U. K. 1970. Cleavage of structural polypeptides during the assembly of the head of bacteriophage T4. Nature 227:680-685.
27. Lee, T. C. and P. J. Langston-Unkefer. 1985. Pyruvate decarboxylase from *Zea mays* L. I. Purification and partial characterization from mature kernals and anaerobically treated roots. Plant Physiol. 79:242-247.
28. Lowe, S. E. and J. G. Zeikus. 1992. Purification and characterization of pyruvate decarboxylase from *Sarcina ventriculi*. J. Gen. Microbiol. 138:803-807.
29. Lu, G., D. Dobritzsch, S. Baumann, G. Schneider, and S. König. 2000. The structural basis of substrate activation in yeast pyruvate decarboxylase. A crystallographic and kinetic study. Eur. J. Biochem. 267:861-868.
30. Matthews, B. W. 1993. Structural and genetic analysis of polypeptide stability. Annu. Rev. Biochem. 62:139-160.
31. Mozhaev, V. V. and K. Martinek. 1984. Structure-stability relationships in polypeptides: new approaches to stabilizing enzymes. Enzyme Microb. Technol. 6:50-59.
32. Müicke, U., S. König, and G. Hütbner. 1995. Purification and characterisation of pyruvate decarboxylase from pea seeds (*Pisum sativum* cv. Miko). Biol. Chem. Hoppe Seyler 376:111-117.
33. Neale, A. D., R. K. Scopes, R. E. Wettenhall, and N. J. Hoogenraad. 1987. Nucleotide sequence of the pyruvate decarboxylase gene from *Zymomonas mobilis*. Nucleic Acids Res. 15:1753-1761.
34. Neale, A. D., R. K. Scopes, R. E. Wettenhall, and N. J. Hoogenraad. 1987. Pyruvate decarboxylase of *Zymomonas mobilis*: isolation, properties, and genetic expression in *Escherichia coli*. J. Bacteriol. 169:1024-1028.
35. Notenboom, V., C. Birsan, R. A. Warren, S. G. Withers, and D. R. Rose. 1998. Exploring the cellulose/xylan specificity of the beta-1,4-glycanase cex from *Cellulomonas fimi* through crystallography and mutation. Biochemistry 37:4751-4758.
36. Okamoto, T., H. Taguchi, K. Nakamura, and H. Ikenaga. 1994. Production of ethanol from maltose by *Zymobacter palmae* fermentation. Biosci. Biotechnol. Biochem. 58:1328-1329.
37. Okamoto, T., H. Taguchi, K. Nakamura, H. Ikenaga, H. Kuraishi, and K. Yamasato. 1993. *Zymobacter palmae* gen. nov., sp. nov., a new ethanol-fermenting peritrichous bacterium isolated from palm sap. Arch. Microbiol. 160: 333-337.
38. Or, E., J. Baybik, A. Sadka, and A. Ogrodovitch. 2000. Fermentative metabolism in grape berries: isolation and characterization of pyruvate decarboxylase cDNA and analysis of its expression throughout berry development. Plant Sci. 156:151 -158.
39. Page, R. D. 1996. TreeView: an application to display phylogenetic trees on personal computers. Comput. Appl. Biosci. 12:357-358.
40. Raj, K. C., L. 0. Ingram, and J. A. Maupin-Furlow. 2001. Pyruvate decarboxylase: a key enzyme for the oxidative metabolism of lactic acid by *Acetobacter pasteurianus*. Arch.Microbiol. 176:443-451.
41. Reid, M. F. and C. A. Fewson. 1994. Molecular characterization of microbial alcohol dehydrogenases. Crit Rev. Microbiol. 20:13-56.
42. Sanger, F., S. Nicklen, and A. R. Coulson. 1977. DNA sequencing with chain-terminating inhibitors. Proc. Natl. Acad. Sci.U.S.A. 74:5463-5467.
43. Schenk, G., F. J. Leeper, R. England, P. F. Nixon, and R. G. Duggleby. 1997. The role of His113 and His114 in pyruvate decarboxylase from *Zymomonas mobilis*. Eur. J. Biochem. 248:63-71.
44. Tadege, M., R. Brandle, and C. Kuhlemeier. 1998. Anoxia tolerance in tobacco roots: effect of overexpression of pyruvate decarboxylase. Plant J. 14:327-335.
45. Talarico, L. A., L. O. Ingram, and J. A. Maupin-Furlow. 2001. Production of the Gram-positive *Sarcina ventriculi* pyruvate decarboxylase in *Escherichia coli*. Microbiology 147:2425-2435.
46. Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680.
47. Tobias, J. W., T. E. Shrader, G. Rocap, and A. Varshavsky. 1991. The N-end rule in bacteria. Science 254: 1374-1377.
48. Vieille, C. and G. J. Zeikus. 2001. Hyperthermophilic enzymes: sources, uses, and molecular mechanisms for thermostability. Microbiol. Mol. Biol. Rev. 65:1-43.

The invention claimed is:

1. An isolated nucleic acid molecule which encodes a polypeptide comprising a nucleotide sequence which is at least about 90% identical to the nucleotide sequence of SEQ ID NO:1, SEQ ID NO:3, or SEQ ID NO:5, or a full complement thereof; or a nucleic acid molecule that hybridizes to a nucleic acid molecule comprising SEQ ID NO:1, SEQ ID NO:3, or SEQ ID NO:5, or a full complement thereof, under stringent conditions comprising hybridization in 6×SSC at about 45° C. followed by one or more washes in 0.2×SSC, 0.1% SDS at 65° C., wherein said polypeptide is capable of decarboxylating pyruvate into acetaldehyde.

2. An isolated nucleic acid molecule selected from the group consisting of:
   a) a nucleic acid molecule comprising the nucleotide sequence of SEQ ID NO:1, SEQ ID NO:3, SEQ ID NO:5, or the complement thereof; and
   b) a nucleic acid molecule which encodes a polypeptide comprising the amino acid sequence of SEQ ID NO:2, SEQ ID NO:4, or SEQ ID NO:6.

3. The nucleic acid molecule of claim 1 or 2 further comprising vector nucleic acid sequences.

4. The nucleic acid molecule of claim 1 or 2 operably linked to a surrogate promoter.

5. The nucleic acid molecule of claim 1 or 2 further comprising nucleic acid sequences encoding a heterologous polypeptide.

6. A kit comprising a compound which hybridizes under stringent conditions to the complement of a nucleic acid molecule of claim 1 or 2 and instructions for use.

7. An isolated recombinant host cell transformed with a polynucleotide which comprises the nucleic acid molecule of claim 1.

8. A method for producing acetaldehyde comprising culturing the host cell of claim 7, under conditions wherein pyruvate decarboxylase is expressed at sufficient levels such that acetaldehyde is produced from pyruvate.

9. The method of claim 8, wherein the host cell further comprises an ethanologenic gene selected from the group consisting of alcohol dehydrogenase, secretase, and glucanase.

10. The method of claim 9, wherein said method is conducted in an aqueous solution.

11. A method for producing acetaldehyde comprising contacting a cell lysate obtained from the host cell of claim 7, under conditions wherein acetaldehyde is produced from pyruvate.

12. A method for producing ethanol comprising culturing the host cell of claim 7, under conditions wherein pyruvate decarboxylase and alcohol dehydrogenase are expressed at sufficient levels such that ethanol is produced as a primary fermentation product.

13. The method of claim 12, wherein said method is conducted in an aqueous solution.

14. An isolated recombinant host cell transformed with a polynucleotide comprising a heterologous nucleic acid sequence encoding pyruvate decarboxylase wherein the nucleic acid sequence is an isolated nucleic acid molecule of claim 1 and is selected for improved codon usage in said host cell.

15. An isolated recombinant host cell transformed with a polynucleotide comprising a heterolagous nucleic acid sequence encoding pyruvate decarboxylase wherein the nucleic acid sequence is an isolated nucleic acid molecule of claim 1 and is selected for improved decarboxylase activity, wherein said decarboxylase activity is selected from the group consisting of substrate affinity of the enzyme, activity at different pHs, or a combination thereof, relative to an unmodified decarboxylase activity.

16. An isolated recombinant host cell transformed with a polynucleotide comprising a heterologous nucleic acid sequence encoding pyruvate decarboxylase wherein the nucleic acid sequence is an isolated nucleic acid molecule of claim 1 and is selected for improved thermal stability.

17. The host cell of claim 14, wherein the heterologous nucleic acid sequence encoding pyruvate decarboxylase is operably linked to a surrogate promoter.

18. A method for detecting the presence of the nucleic acid molecule of claim 1 in a sample comprising:
 a) contacting the sample with a nucleic acid probe or primer which selectively hybridizes to the complement of the nucleic acid molecule, wherein the nucleic acid probe or primer hybridizes under stringent conditions comprising hybridization in 6×SSC at about 45° C. followed by one or more washes in 0.2×SSC, 0.1% SDS at 65° C.; and
 b) determining whether the nucleic acid probe or primer binds to the nucleic acid molecule in the sample to thereby detect the presence of the nucleic acid molecule of claim 1 in the sample.

19. The method of claim 18 wherein the sample comprises mRNA molecules and is contacted with a nucleic acid probe.

20. An isolated recombinant host cell transformed with a polynucleotide which comprises the nucleic acid molecule of claim 2.

21. An isolated recombinant host cell transformed with a polynucleotide comprising a heterologous nucleic acid sequence encoding pyruvate decarboxylase wherein the nucleic acid sequence is an isolated nucleic acid molecule of claim 2 and is selected for improved codon usage in said host cell.

22. An isolated recombinant host cell transformed with a polynucleotide comprising a heterologous nucleic acid sequence encoding pyruvate decarboxylase wherein the nucleic acid sequence is an isolated nucleic acid molecule of claim 2 and is selected for improved decarboxylase activity, wherein said decarboxylase activity is selected from the group consisting of substrate affinity of the enzyme, activity at different pHs, or a combination thereof, relative to an unmodified decarboxylase activity.

23. An isolated recombinant host cell transformed with a polynucleotide comprising a heterologous nucleic acid sequence encoding pyruvate decarboxylase wherein the nucleic acid sequence is an isolated nucleic acid molecule of claim 2 and is selected for improved thermal stability.

24. The host cell of claim 20, wherein the heterologous nucleic acid sequence encoding pyruvate decarboxylase is operably linked to a surrogate promoter.

25. The recombinant host coil of claim 7 or 20, wherein the host cell is selected from the group consisting of a Gram-negative bacterial cell and a Gram-positive bacterial cell.

26. The recombinant host cell of claim 7 or 20, wherein the Gram-negative bacterial cell is selected from the group consisting of *Gluconobacter, Rhizobium, Bradyrhizobium, Alcaligenes, Rhodobacter, Rhodococcus, Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas, Zymobacter*, and *Acetbacter*.

27. The recombinant host cell of claim 7 or 20, wherein the Gram-positive bacterial cell is selected from the group consisting of *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptoccus, Lactobacillus, Leuconostoc, Enterococcus, Lactococcus, Thermobifida, Cellulomonas*, and *Sarcina*.

28. A method for producing acetaldehyde comprising culturing the host cell of claim 20, under conditions wherein pyruvate decarboxylase is expressed at sufficient levels such that acetaldehyde is produced from pyruvate.

29. The method of claim 28, wherein the host cell further comprises an ethanologenic gene selected from the group consisting of alcohol dehydrogenase, secretase, and glucanase.

30. The method of claim 29, wherein said method is conducted in an aqueous solution.

31. A method for producing acetaldehyde comprising contacting a cell lysate obtained from the host cell of claim 20, under conditions wherein acetaldehyde is produced from pyruvate.

32. A method for producing ethanol comprising culturing the host cell of claim 20, under conditions wherein pyruvate decarboxylase and alcohol dehydrogenase are expressed at sufficient levels such that ethanol is produced as a primary fermentation product.

33. The method of claim 32, wherein said method is conducted in an aqueous solution.

34. The host cell of claim 21, wherein the heterologous nucleic acid sequence encoding pyruvate decarboxylase is isolated from a bacterial cell selected from the group consisting or *Zymobacter palmae, Acetobacter pasteurianus*, and *Sarcina ventriculi*.

35. The host cell of any one of claims 14-17 and 21-24, wherein the heterologous nucleic acid sequence is selected from the group consisting of SEQ ID NO:1, SEQ ID NO:3, and SEQ ID NO:5.

36. The host cell of any one claims 7, 14-17 and 21-24, wherein the host cell further comprises a nucleic acid encoding a polypeptide selected from the group consisting of an alcohol dehydrogenase, glucanase, and secretase.

37. The host cell of claim 36, wherein the host cell further comprises a nucleic acid encoding alcohol dehydrogenase.

38. The host cell of any one of claims 7, 14-17 and 20-24, wherein the host cell is ethanologenic.

39. The host cell of any one of claims 7, 14-17 and 20-24, wherein the host cell is suitable for fermenting ethanol from a sugar.

40. The recombinant host cell of any one of claims 14-17 and 21-24, wherein said host cell is a bacterial cell selected from the group consisting of Gram-negative bacterial cells and Gram-positive bacterial cells.

41. The host cell of claim 40, wherein the Gram-negative bacterial cell is selected from the group consisting of *Gluconobacter, Rhizobium, Bradyrhizobium, Alcaligenes, Rhodobacter, Rhodococcus, Azospirillum, Rhodospirillum, Sphingomonas, Burkholderia, Desulfomonas, Geospirillum, Succinomonas, Aeromonas, Shewanella, Haolchromatium, Citrobacter, Escherichia, Klebsiella, Zymonmonas, Zymobacter*, and *Acetobacter*.

42. The host cell of claim 40, wherein the Gram-positive bacterial cell is selected from the group consisting of *Fibrobacter, Acidobacter, Bacteroides, Sphingobacterium, Actinomyces, Corynebacterium, Nocardia, Rhodococcus, Propionibacterium, Bifidobacterium, Bacillus, Geobacillus, Paenibacillus, Sulfobacillus, Clostridium, Anaerobacter, Eubacterium, Streptococcus, Lactobacillus, Leuconostoc, Enterococcus, Lactococcus, Thermobifida, Cellulomonas*, and *Sarcina*.

43. A method for producing a polypeptide capable of decarboxylating pyruvate into acetaldehyde selected train the group consisting of:
   a) a polypeptide comprising the amino acid sequence SEQ ID NO:2, SEQ ID NO:4, or SEQ ID NO:6;
   b) a polypeptide comprising an amino acid sequence that is at least 90% identical to SEQ ID NO:2, SEQ ID NO:4, or SEQ ID NO:6; and
   c) a polypeptide encoded by a nucleic acid molecule which hybridizes to a nucleic acid molecule comprising SEQ ID NO:1, SEQ ID NO:3, or SEQ ID NO:5, or the complement thereof, under stringent conditions comprising hybridization in 6×SSC at about 45° C. followed by one or more washes in 0.2×SSC, 0.1% SDS at 65° C.; wherein the method comprises culturing the host cell of claim 6 under conditions in which (he nucleic acid molecule is expressed.

44. An isolated recombinant ethanologenic host cell transformed with a polynucleotide comprising a heterologous nucleic acid encoding a pyruvate decarboxylase (PDC) selected from the group consisting SEQ ID NO:2, SEQ ID NO:4, and SEQ ID NO:6, wherein the nucleic acid is under the transcriptional control of an exogenous surrogate promoter.

45. The plasmid pJAM3440 encoding a pdc gene derived from *Zymobacter palmae* represented by a deposit with the American Type Culture Collection designated as deposit number ATCC PTA-4254.

46. The plasmid pJAM304 encoding a pdc gene derived from *Acetobacter pasteurianus* represented by a deposit with the American Type Culture Collection designated as deposit number ATCC PTA-4252.

47. The plasmid pJAM419 encoding a pdc gene derived from *Sarcina ventriculi* represented by a deposit with the American Type Culture Collection designated as deposit number ATCC PTA-4253.

48. An isolated recombinant ethanologenic host cell transformed with a polynucleotide comprising a heterologous nucleic acid sequence is selected from the group consisting of SEQ ID NO:1, SEQ ID NO:3, and SEQ ID NO:5, wherein the heterologous nucleic acid sequence encodes pyruvate decarboxylase.

49. The host cell of claim 48 wherein the nucleic acid sequence is selected for improved codon usage in said host cell.

50. The host cell of claim 48 wherein the nucleic acid sequence is selected for improved decarboxylase activity, wherein said decarboxylase activity is selected from the group consisting of substrate affinity of the enzyme, activity at different pHs, or a combination thereof, relative to an unmodified decarboxylase activity.

51. The host cell of claim 48 wherein the nucleic acid sequence is selected for improved thermal stability.

* * * * *

SEQUENCE LISTING

<160> NUMBER OF SEQ ID NOS: 11

<210> SEQ ID NO 1
<211> LENGTH: 1671
<212> TYPE: DNA
<213> ORGANISM: Zymobacter palmae

<400> SEQUENCE: 1

```
atgtataccg ttggtatgta cttggcagaa cgcctagccc agatcggcct gaaacaccac        60
tttgccgtgg ccggtgacta caacctggtg ttgcttgatc agctcctgct gaacaaagac       120
atggagcagg tctactgctg taacgaactt aactgcggct ttagcgccga aggttacgct       180
cgtgcacgtg gtgccgccgc tgccatcgtc acgttcagcg taggtgctat ctctgcaatg       240
aacgccatcg gtgcgccta tgcagaaaac ctgccggtca tcctgatctc tggctcaccg       300
aacaccaatg actacggcac aggccacatc ctgcaccaca ccattggtac tactgactat       360
aactatcagc tggaaatggt aaaacacgtt acctgcgcac gtgaaagcat cgtttctgcc       420
gaagaagcac cggcaaaaat cgaccacgtc atccgtacgg ctctacgtga acgcaaaccg       480
gcttatctgg aaatcgcatg caacgtcgct ggcgctgaat gtgttcgtcc gggcccgatc       540
aatagcctgc tgcgtgaact cgaagttgac cagaccagtg tcactgccgc tgtagatgcc       600
gccgtagaat ggctgcagga ccgccagaac gtcgtcatgc tggtcggtag caaactgcgt       660
gccgctgccg ctgaaaaaca ggctgttgcc ctagcggacc gcctgggctg cgctgtcacg       720
atcatggctg ccgaaaaagg cttcttcccg gaagatcatc cgaacttccg cggcctgtac       780
tggggtgaag tcagctccga aggtgcacag gaactggttg aaaacgccga tgccatcctg       840
tgtctggcac cggtattcaa cgactatgct accgttggct ggaactcctg gccgaaaggc       900
gacaatgtca tggtcatgga caccgaccgc gtcactttcg caggacagtc cttcgaaggt       960
ctgtcattga gcaccttcgc cgcagcactg gctgagaaag ccctctcg cccggcaacg      1020 actcaaggca ctcaagcacc ggtactgggt attgaggccg cagagcccaa tgcaccgctg      1080
accaatgacg aaatgacgcg tcagatccag tcgctgatca cttccgacac tactctgaca      1140
gcagaaacag gtgactcttg gttcaacgct tctcgcatgc cgattcctgg cggtgctcgt      1200
gtcgaactgg aaatgcaatg gggtcatatc ggttggtccg taccttctgc attcggtaac      1260
gccgttggtt ctccggagcg tcgccacatc atgatggtcg gtgatggctc tttccagctg      1320
actgctcaag aagttgctca gatgatccgc tatgaaatcc cggtcatcat cttcctgatc      1380
aacaaccgcg gttacgtcat cgaaatcgct atccatgacg gcccttacaa ctacatcaaa      1440
```

-continued

```
aactggaact acgctggcct gatcgacgtc ttcaatgacg aagatggtca tggcctgggt    1500
ctgaaagctt ctactggtgc agaactagaa ggcgctatac agaaagcact cgacaatcgt    1560
cgcggtccga cgctgatcga atgtaacatc gctcaggacg actgcactga aaccctgatt    1620
gcttggggta acgtgtagc agctaccaac tctcgcaaac cacaagcgta a              1671
```

<210> SEQ ID NO 2
<211> LENGTH: 556
<212> TYPE: PRT
<213> ORGANISM: Zymobacter palmae

<400> SEQUENCE: 2

```
Met Tyr Thr Val Gly Met Tyr Leu Ala Glu Arg Leu Ala Gln Ile Gly
  1               5                  10                  15

Leu Lys His His Phe Ala Val Ala Gly Asp Tyr Asn Leu Val Leu Leu
             20                  25                  30

Asp Gln Leu Leu Leu Asn Lys Asp Met Glu Gln Val Tyr Cys Cys Asn
         35                  40                  45

Glu Leu Asn Cys Gly Phe Ser Ala Glu Gly Tyr Ala Arg Ala Arg Gly
     50                  55                  60

Ala Ala Ala Ala Ile Val Thr Phe Ser Val Gly Ala Ile Ser Ala Met
 65                  70                  75                  80

Asn Ala Ile Gly Gly Ala Tyr Ala Glu Asn Leu Pro Val Ile Leu Ile
                 85                  90                  95

Ser Gly Ser Pro Asn Thr Asn Asp Tyr Gly Thr Gly His Ile Leu His
            100                 105                 110

His Thr Ile Gly Thr Thr Asp Tyr Asn Tyr Gln Leu Glu Met Val Lys
        115                 120                 125

His Val Thr Cys Ala Arg Glu Ser Ile Val Ser Ala Glu Glu Ala Pro
    130                 135                 140

Ala Lys Ile Asp His Val Ile Arg Thr Ala Leu Arg Glu Arg Lys Pro
145                 150                 155                 160

Ala Tyr Leu Glu Ile Ala Cys Asn Val Ala Gly Ala Glu Cys Val Arg
                165                 170                 175

Pro Gly Pro Ile Asn Ser Leu Leu Arg Glu Leu Glu Val Asp Gln Thr
            180                 185                 190

Ser Val Thr Ala Ala Val Asp Ala Ala Val Glu Trp Leu Gln Asp Arg
        195                 200                 205

Gln Asn Val Val Met Leu Val Gly Ser Lys Leu Arg Ala Ala Ala Ala
    210                 215                 220

Glu Lys Gln Ala Val Ala Leu Ala Asp Arg Leu Gly Cys Ala Val Thr
225                 230                 235                 240

Ile Met Ala Ala Glu Lys Gly Phe Phe Pro Glu Asp His Pro Asn Phe
                245                 250                 255

Arg Gly Leu Tyr Trp Gly Glu Val Ser Ser Glu Gly Ala Gln Glu Leu
            260                 265                 270

Val Glu Asn Ala Asp Ala Ile Leu Cys Leu Ala Pro Val Phe Asn Asp
        275                 280                 285

Tyr Ala Thr Val Gly Trp Asn Ser Trp Pro Lys Gly Asp Asn Val Met
    290                 295                 300

Val Met Asp Thr Asp Arg Val Thr Phe Ala Gly Gln Ser Phe Glu Gly
305                 310                 315                 320

Leu Ser Leu Ser Thr Phe Ala Ala Ala Leu Ala Glu Lys Ala Pro Ser
                325                 330                 335
```

-continued

| | | | | | | | | | | | | |
|---|---|---|---|---|---|---|---|---|---|---|---|---|
|Arg|Pro|Ala|Thr|Thr|Gln|Gly|Thr|Gln|Ala|Pro|Val|Leu|Gly|Ile|Glu|
| | | |340| | | |345| | | | |350| | | |

Ala Ala Glu Pro Asn Ala Pro Leu Thr Asn Asp Glu Met Thr Arg Gln
            355                 360                 365

Ile Gln Ser Leu Ile Thr Ser Asp Thr Thr Leu Thr Ala Glu Thr Gly
        370                 375                 380

Asp Ser Trp Phe Asn Ala Ser Arg Met Pro Ile Pro Gly Gly Ala Arg
385                 390                 395                 400

Val Glu Leu Glu Met Gln Trp Gly His Ile Gly Trp Ser Val Pro Ser
                405                 410                 415

Ala Phe Gly Asn Ala Val Gly Ser Pro Glu Arg Arg His Ile Met Met
            420                 425                 430

Val Gly Asp Gly Ser Phe Gln Leu Thr Ala Gln Glu Val Ala Gln Met
        435                 440                 445

Ile Arg Tyr Glu Ile Pro Val Ile Ile Phe Leu Ile Asn Asn Arg Gly
    450                 455                 460

Tyr Val Ile Glu Ile Ala Ile His Asp Gly Pro Tyr Asn Tyr Ile Lys
465                 470                 475                 480

Asn Trp Asn Tyr Ala Gly Leu Ile Asp Val Phe Asn Asp Glu Asp Gly
                485                 490                 495

His Gly Leu Gly Leu Lys Ala Ser Thr Gly Ala Glu Leu Glu Gly Ala
            500                 505                 510

Ile Lys Lys Ala Leu Asp Asn Arg Arg Gly Pro Thr Leu Ile Glu Cys
        515                 520                 525

Asn Ile Ala Gln Asp Asp Cys Thr Glu Thr Leu Ile Ala Trp Gly Lys
    530                 535                 540

Arg Val Ala Ala Thr Asn Ser Arg Lys Pro Gln Ala
545                 550                 555

<210> SEQ ID NO 3
<211> LENGTH: 1674
<212> TYPE: DNA
<213> ORGANISM: Acetobacter pasteurianus

<400> SEQUENCE: 3

```
gtgacctata ctgttggcat gtatcttgca gaacgccttg tacagatcgg gctgaagcat     60
cacttcgccg tgggcggcga ctacaatctc gttcttctgg atcagttgct cctcaacaag    120
gacatgaaac agatctattg ctgcaatgag ttgaactgtg gcttcagcgc ggaaggctac    180
gcccgttcta acgggctgc ggcagcggtt gtcaccttca gcgttggcgc catttccgcc    240
atgaacgccc tcggcggcgc ctatgccgaa aacctgccgg ttatcctgat tccggcgcg    300 cccaacagca atgatcaggg cacaggtcat atcctgcatc acacaatcgg caagacggat    360
tacagctacc agcttgaaat ggcccgtcag gtcacctgtg ccgccgaaag cattaccgac    420
gctcactccg ccccggccaa gattgaccac gtcattcgca cggcgctgcg cgagcgtaag    480
ccggcctatc tggacatcgc gtgcaacatt gcctccgagc cctgcgtgcg gcctggccct    540
gtcagcagcc tgctgtccga gcctgaaatc gaccacacga gctgaaggc cgcagtggac    600 gccacggttg ccttgctgaa aaatcggcca gccccgtca tgctgctggg cagcaagctg    660
cgggccgcca acgcactggc cgcaaccgaa acgctggcag acaagctgca atgcgcggtg    720
accatcatgg cggccgcgaa aggcttttc cccgaagacc acgcgggttt ccgcggcctg    780
tactggggcg aagtctcgaa ccccggcgtg caggaactgg tggagacctc cgacgcactg    840
ctgtgcatcg cccccgtatt caacgactat tcaacagtcg gctggtcggg catgcccaag    900
```

```
ggcccccaatg tgattctggc tgagcccgac cgcgtaacgg tcgatggccg cgcctatgac    960
ggctttaccc tgcgcgcctt cctgcaggct ctggcggaaa aagcccccgc gcgcccggcc   1020
tccgcacaga aaagcagcgt cccgacgtgc tcgctcaccg cgacatccga tgaagccggt   1080
ctgacgaatg acgaaatcgt ccgtcatatc aacgccctgc tgacatcaaa cacgacgctg   1140
gtggcagaaa ccggcgattc atggttcaat gccatgcgca tgaccctggc cggtgcgcgc   1200
gtggaactgg aaatgcagtg gggccatatc ggctggtccg tgccctccgc gttcggcaat   1260
gccatgggct cgcaggaccg ccagcatgtg gtgatggtag cgatggctc cttccagctt    1320
accgcgcagg aagtggctca gatggtgcgc tacgaactgc ccgtcattat ctttctgatc   1380
aacaaccgtg gctatgtcat tgaaatcgcc attcatgacg cccgtacaa ctatatcaag    1440
aactgggatt acgccggcct gatggaagtc ttcaacgccg agaaggcca tggacttggc    1500
ctgaaagcca ccaccccgaa ggaactgaca gaagccatcg ccagggcaaa agccaatacc   1560
cgcggcccga cgctgatcga atgccagatc gaccgcacgg actgcacgga tatgctggtt   1620
caatggggcc gcaaggttgc ctcaaccaac gcgcgcaaga ccactctggc ctga         1674

<210> SEQ ID NO 4
<211> LENGTH: 557
<212> TYPE: PRT
<213> ORGANISM: Acetobacter pasteurianus

<400> SEQUENCE: 4

Met Thr Tyr Thr Val Gly Met Tyr Leu Ala Glu Arg Leu Val Gln Ile
 1               5                  10                  15

Gly Leu Lys His His Phe Ala Val Gly Gly Asp Tyr Asn Leu Val Leu
                20                  25                  30

Leu Asp Gln Leu Leu Leu Asn Lys Asp Met Lys Gln Ile Tyr Cys Cys
             35                  40                  45

Asn Glu Leu Asn Cys Gly Phe Ser Ala Glu Gly Tyr Ala Arg Ser Asn
         50                  55                  60

Gly Ala Ala Ala Val Val Thr Phe Ser Val Gly Ala Ile Ser Ala
 65                  70                  75                  80

Met Asn Ala Leu Gly Gly Ala Tyr Ala Glu Asn Leu Pro Val Ile Leu
                 85                  90                  95

Ile Ser Gly Ala Pro Asn Ser Asn Asp Gln Gly Thr Gly His Ile Leu
            100                 105                 110

His His Thr Ile Gly Lys Thr Asp Tyr Ser Tyr Gln Leu Glu Met Ala
        115                 120                 125

Arg Gln Val Thr Cys Ala Ala Glu Ser Ile Thr Asp Ala His Ser Ala
    130                 135                 140

Pro Ala Lys Ile Asp His Val Ile Arg Thr Ala Leu Arg Glu Arg Lys
145                 150                 155                 160

Pro Ala Tyr Leu Asp Ile Ala Cys Asn Ile Ala Ser Glu Pro Cys Val
                165                 170                 175

Arg Pro Gly Pro Val Ser Ser Leu Leu Ser Glu Pro Glu Ile Asp His
            180                 185                 190

Thr Ser Leu Lys Ala Ala Val Asp Ala Thr Val Ala Leu Leu Lys Asn
        195                 200                 205

Arg Pro Ala Pro Val Met Leu Leu Gly Ser Lys Leu Arg Ala Ala Asn
    210                 215                 220

Ala Leu Ala Ala Thr Glu Thr Leu Ala Asp Lys Leu Gln Cys Ala Val
225                 230                 235                 240
```

```
Thr Ile Met Ala Ala Ala Lys Gly Phe Phe Pro Glu Asp His Ala Gly
                245                 250                 255
Phe Arg Gly Leu Tyr Trp Gly Glu Val Ser Asn Pro Gly Val Gln Glu
            260                 265                 270
Leu Val Glu Thr Ser Asp Ala Leu Leu Cys Ile Ala Pro Val Phe Asn
        275                 280                 285
Asp Tyr Ser Thr Val Gly Trp Ser Gly Met Pro Lys Gly Pro Asn Val
    290                 295                 300
Ile Leu Ala Glu Pro Asp Arg Val Thr Val Asp Gly Arg Ala Tyr Asp
305                 310                 315                 320
Gly Phe Thr Leu Arg Ala Phe Leu Gln Ala Leu Ala Glu Lys Ala Pro
                325                 330                 335
Ala Arg Pro Ala Ser Ala Gln Lys Ser Ser Val Pro Thr Cys Ser Leu
            340                 345                 350
Thr Ala Thr Ser Asp Glu Ala Gly Leu Thr Asn Asp Glu Ile Val Arg
        355                 360                 365
His Ile Asn Ala Leu Leu Thr Ser Asn Thr Thr Leu Val Ala Glu Thr
    370                 375                 380
Gly Asp Ser Trp Phe Asn Ala Met Arg Met Thr Leu Ala Gly Ala Arg
385                 390                 395                 400
Val Glu Leu Glu Met Gln Trp Gly His Ile Gly Trp Ser Val Pro Ser
                405                 410                 415
Ala Phe Gly Asn Ala Met Gly Ser Gln Asp Arg Gln His Val Val Met
            420                 425                 430
Val Gly Asp Gly Ser Phe Gln Leu Thr Ala Gln Glu Val Ala Gln Met
        435                 440                 445
Val Arg Tyr Glu Leu Pro Val Ile Ile Phe Leu Ile Asn Asn Arg Gly
    450                 455                 460
Tyr Val Ile Glu Ile Ala Ile His Asp Gly Pro Tyr Asn Tyr Ile Lys
465                 470                 475                 480
Asn Trp Asp Tyr Ala Gly Leu Met Glu Val Phe Asn Ala Gly Glu Gly
                485                 490                 495
His Gly Leu Gly Leu Lys Ala Thr Thr Pro Lys Glu Leu Thr Glu Ala
            500                 505                 510
Ile Ala Arg Ala Lys Ala Asn Thr Arg Gly Pro Thr Leu Ile Glu Cys
        515                 520                 525
Gln Ile Asp Arg Thr Asp Cys Thr Asp Met Leu Val Gln Trp Gly Arg
    530                 535                 540
Lys Val Ala Ser Thr Asn Ala Arg Lys Thr Thr Leu Ala
545                 550                 555

<210> SEQ ID NO 5
<211> LENGTH: 1659
<212> TYPE: DNA
<213> ORGANISM: Sarcina ventriculi

<400> SEQUENCE: 5
atgaaaataa caattgcaga atacttatta aaaagattaa agaagtaaa tgtagagcat      60 atgtttggag ttcctggaga ttataactta ggattttag attatgttga agattctaaa    120
gatattgaat gggttggaag ctgtaatgaa cttaatgcag atatgcagc agatggatat    180 gcaagactta gaggatttgg tgtaatactt acaacttatg gagttggttc acttagtgca    240
ataaatgcta acacaggttc atttgcagaa atgttccag tattacatat atcaggtgta    300
ccatcagctt tagttcaaca aaacagaaag ctagttcacc attcaactgc tagaggagaa    360
```

-continued

```
ttcgacactt tgaaagaat gtttagagaa ataacagaat tcaatcaat cataagcgaa    420 tataatgcag ctgaagaaat cgatagagtt atagaatcaa tatataaata tcaattacca   480
ggttatatag aattaccagt tgatatagtt tcaaaagaaa tagaaatcga cgaaatgaaa   540
ccgctaaact taactatgag aagcaacgag aaaactttag agaaattcgt aaatgatgta   600
aaagaaatgg ttgcaagctc aaaaggacaa catattttag ctgattatga agtattaaga   660
gctaaagctg aaaagaatt agaaggattt ataaatgaag caaaaatccc agtaaacact    720
ttaagtatag aaagacagc agtatcagaa agcaatccat actttgctgg attattctca    780
ggagaaacta gttcagattt agttaaagaa ctttgcaaag cttctgatat agttttacta   840
tttggagtta aattcataga tactacaaca gctggattta gatatataaa taaagatgtt   900
aaaatgatag aaattggttt aactgattgt agaattggag aaactattta tactggactt   960
tacattaaag atgttataaa agctttaaca gatgctaaaa taaaattcca taacgatgta  1020
aaagtagaaa gagaagcagt agaaaaattt gttccaacag atgctaaatt aactcaagat  1080
agatatttca aacaaatgga agcgttctta aaacctaatg atgtattagt tggtgaaaca  1140
ggaacatcat atagtggagc atgtaatatg agattcccag aaggatcaag ctttgtaggt  1200
caaggatctt ggatgtcaat tggatatgct actcctgcag ttttaggaac tcatttagct  1260
gataagagca aagaaacat tcttttaagt ggtgatggtt cattccaatt aacagttcaa  1320
gaagtttcaa caatgataag acaaaaatta aatacagtat tatttgtagt taacaatgat  1380
ggatatacaa ttgaaagatt aatccacgga cctgaaagag aatataacca tattcaaatg  1440
tggcaatatg cagaacttgt aaaaacatta gctactgaaa gagatataca accaacttgt  1500
ttcaaagtta caactgaaaa agaattagca gctgcaatgg aagaaataaa caaaggaaca  1560
gaaggtattg cttttgttga agtagtaatg gataaaatgg atgctccaaa atcattaaga  1620
caagaagcaa gtctatttag ttctcaaaat aactactaa                         1659
```

<210> SEQ ID NO 6
<211> LENGTH: 552
<212> TYPE: PRT
<213> ORGANISM: Sarcina ventriculi

<400> SEQUENCE: 6

```
Met Lys Ile Thr Ile Ala Glu Tyr Leu Leu Lys Arg Leu Lys Glu Val
  1               5                  10                  15

Asn Val Glu His Met Phe Gly Val Pro Gly Asp Tyr Asn Leu Gly Phe
             20                  25                  30

Leu Asp Tyr Val Glu Asp Ser Lys Asp Ile Glu Trp Val Gly Ser Cys
         35                  40                  45

Asn Glu Leu Asn Ala Gly Tyr Ala Ala Asp Gly Tyr Ala Arg Leu Arg
     50                  55                  60

Gly Phe Gly Val Ile Leu Thr Thr Tyr Gly Val Gly Ser Leu Ser Ala
 65                  70                  75                  80

Ile Asn Ala Thr Thr Gly Ser Phe Ala Glu Asn Val Pro Val Leu His
                 85                  90                  95

Ile Ser Gly Val Pro Ser Ala Leu Val Gln Gln Asn Arg Lys Leu Val
            100                 105                 110

His His Ser Thr Ala Arg Gly Glu Phe Asp Thr Phe Glu Arg Met Phe
        115                 120                 125

Arg Glu Ile Thr Glu Phe Gln Ser Ile Ile Ser Glu Tyr Asn Ala Ala
    130                 135                 140
```

```
Glu Glu Ile Asp Arg Val Ile Glu Ser Ile Tyr Lys Tyr Gln Leu Pro
145                 150                 155                 160
Gly Tyr Ile Glu Leu Pro Val Asp Ile Val Ser Lys Glu Ile Glu Ile
                165                 170                 175
Asp Glu Met Lys Pro Leu Asn Leu Thr Met Arg Ser Asn Glu Lys Thr
            180                 185                 190
Leu Glu Lys Phe Val Asn Asp Val Lys Glu Met Val Ala Ser Ser Lys
        195                 200                 205
Gly Gln His Ile Leu Ala Asp Tyr Glu Val Leu Arg Ala Lys Ala Glu
    210                 215                 220
Lys Glu Leu Glu Gly Phe Ile Asn Glu Ala Lys Ile Pro Val Asn Thr
225                 230                 235                 240
Leu Ser Ile Gly Lys Thr Ala Val Ser Glu Ser Asn Pro Tyr Phe Ala
                245                 250                 255
Gly Leu Phe Ser Gly Glu Thr Ser Ser Asp Leu Val Lys Glu Leu Cys
            260                 265                 270
Lys Ala Ser Asp Ile Val Leu Leu Phe Gly Val Lys Phe Ile Asp Thr
        275                 280                 285
Thr Thr Ala Gly Phe Arg Tyr Ile Asn Lys Asp Val Lys Met Ile Glu
    290                 295                 300
Ile Gly Leu Thr Asp Cys Arg Ile Gly Glu Thr Ile Tyr Thr Gly Leu
305                 310                 315                 320
Tyr Ile Lys Asp Val Ile Lys Ala Leu Thr Asp Ala Lys Ile Lys Phe
                325                 330                 335
His Asn Asp Val Lys Val Glu Arg Glu Ala Val Glu Lys Phe Val Pro
            340                 345                 350
Thr Asp Ala Lys Leu Thr Gln Asp Arg Tyr Phe Lys Gln Met Glu Ala
        355                 360                 365
Phe Leu Lys Pro Asn Asp Val Leu Val Gly Glu Thr Gly Thr Ser Tyr
    370                 375                 380
Ser Gly Ala Cys Asn Met Arg Phe Pro Glu Gly Ser Ser Phe Val Gly
385                 390                 395                 400
Gln Gly Ser Trp Met Ser Ile Gly Tyr Ala Thr Pro Ala Val Leu Gly
                405                 410                 415
Thr His Leu Ala Asp Lys Ser Arg Arg Asn Ile Leu Leu Ser Gly Asp
            420                 425                 430
Gly Ser Phe Gln Leu Thr Val Gln Glu Val Ser Thr Met Ile Arg Gln
        435                 440                 445
Lys Leu Asn Thr Val Leu Phe Val Val Asn Asn Asp Gly Tyr Thr Ile
450                 455                 460
Glu Arg Leu Ile His Gly Pro Glu Arg Glu Tyr Asn His Ile Gln Met
465                 470                 475                 480
Trp Gln Tyr Ala Glu Leu Val Lys Thr Leu Ala Thr Glu Arg Asp Ile
                485                 490                 495
Gln Pro Thr Cys Phe Lys Val Thr Thr Glu Lys Glu Leu Ala Ala Ala
            500                 505                 510
Met Glu Glu Ile Asn Lys Gly Thr Glu Gly Ile Ala Phe Val Glu Val
        515                 520                 525
Val Met Asp Lys Met Asp Ala Pro Lys Ser Leu Arg Gln Glu Ala Ser
    530                 535                 540
Leu Phe Ser Ser Gln Asn Asn Tyr
545                 550
```

<210> SEQ ID NO 7
<211> LENGTH: 1707
<212> TYPE: DNA
<213> ORGANISM: Zymomonas mobilis

<400> SEQUENCE: 7

```
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aggcgcagc agcagccgtc gttacctaca cgtcggtgc gctttccgca      240
tttgatgcta tcggtggcgc ctatgcagaa accttccgg ttatcctgat ctccggtgct      300
ccgaacaaca atgatcacgc tgctggtcac gtgttgcatc acgctcttgg caaaaccgac     360
tatcactatc agttggaaat ggccaagaac atcacggccg cagctgaagc gatttacacc     420
ccagaagaag ctccggctaa atcgatcac gtgattaaaa ctgctcttcg tgagaagaag      480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaaccctga attcatcgc caaccgcgac aaagttgccg tcctcgtcgg cagcaagctg      660
cgcgcagctg gtgctgaaga gctgctgtc aaatttgctg atgctctcgg tggcgcagtt      720
gctaccatgg ctgctgcaaa aagcttcttc ccagaagaaa acccgcatta tcggtacc      780
tcatggggtg aagtcagcta tccgggcgtt gaaaagacga tgaaagaagc cgatgcggtt     840
atcgctctgg ctcctgtctt caacgactac tccaccactg gttggacgga tattcctgat     900
cctaagaaac tggttctcgc tgaaccgcgt tctgtcgtcg ttaacggcgt tcgcttcccc     960
agcgttcatc tgaaagacta tctgacccgt ttggctcaga agtttccaa gaaaaccggt     1020
gctttggact tcttcaaatc cctcaatgca ggtgaactga gaaagccgc tccggctgat     1080
ccgagtgctc cgttggtcaa cgcagaaatc gcccgtcagg tcgaagctct tctgaccccg     1140
aacacgacgg ttattgctga accggtgac tcttggttca atgctcagcg catgaagctc     1200
ccgaacggtg ctcgcgttga atatgaaatg cagtggggtc acatcggttg gtccgttcct     1260
gccgccttcg gttatgccgt cggtgctccg gaacgtcgca acatcctcat ggttggtgat     1320
ggttccttcc agctgacggc tcaggaagtc gctcagatgg ttcgcctgaa actgccggtt     1380
atcatcttct tgatcaataa ctatggttac accatcgaag ttatgatcca tgatggtccg     1440
tacaacaaca tcaagaactg ggattatgcc ggtctgatgg aagtgttcaa cggtaacggt     1500
ggttatgaca gcggtgctgg taaaggcctg aaggctaaaa ccggtggcga actggcagaa     1560
gctatcaagg ttgctctggc aaacaccgac ggcccaaccc tgatcgaatg cttcatcggt     1620
cgtgaagact gcactgaaga attggtcaaa tggggtaagc gcgttgctgc cgccaacagc     1680
cgtaagcctg ttaacaagct cctctag                                        1707
```

<210> SEQ ID NO 8
<211> LENGTH: 568
<212> TYPE: PRT
<213> ORGANISM: Zymomonas mobilis

<400> SEQUENCE: 8

```
Met Ser Tyr Thr Val Gly Thr Tyr Leu Ala Glu Arg Leu Val Gln Ile
 1               5                  10                  15

Gly Leu Lys His His Phe Ala Val Ala Gly Asp Tyr Asn Leu Val Leu
            20                  25                  30
```

```
Leu Asp Asn Leu Leu Asn Lys Asn Met Glu Gln Val Tyr Cys Cys
     35                  40                  45

Asn Glu Leu Asn Cys Gly Phe Ser Ala Glu Gly Tyr Ala Arg Ala Lys
 50                  55                  60

Gly Ala Ala Ala Ala Val Val Thr Tyr Ser Val Gly Ala Leu Ser Ala
 65                  70                  75                  80

Phe Asp Ala Ile Gly Gly Ala Tyr Ala Glu Asn Leu Pro Val Ile Leu
                 85                  90                  95

Ile Ser Gly Ala Pro Asn Asn Asn Asp His Ala Ala Gly His Val Leu
                100                 105                 110

His His Ala Leu Gly Lys Thr Asp Tyr His Tyr Gln Leu Glu Met Ala
             115                 120                 125

Lys Asn Ile Thr Ala Ala Ala Glu Ala Ile Tyr Thr Pro Glu Glu Ala
130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Asn Gly Val Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
```

-continued

```
                450                 455                 460
Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
                500                 505                 510

Lys Thr Gly Gly Glu Leu Ala Glu Ala Ile Lys Val Ala Leu Ala Asn
                515                 520                 525

Thr Asp Gly Pro Thr Leu Ile Glu Cys Phe Ile Gly Arg Glu Asp Cys
                530                 535                 540

Thr Glu Glu Leu Val Lys Trp Gly Lys Arg Val Ala Ala Asn Ser
545                 550                 555                 560

Arg Lys Pro Val Asn Lys Leu Leu
                565
```

<210> SEQ ID NO 9
<211> LENGTH: 610
<212> TYPE: PRT
<213> ORGANISM: Zea mays

<400> SEQUENCE: 9

```
Met Glu Thr Leu Leu Ala Gly Asn Pro Ala Asn Gly Val Ala Lys Pro
1               5                   10                  15

Thr Cys Asn Gly Val Gly Ala Leu Pro Val Ala Asn Ser His Ala Ile
                20                  25                  30

Ile Ala Thr Pro Ala Ala Ala Ala Thr Leu Ala Pro Ala Gly Ala
            35                  40                  45

Thr Leu Gly Arg His Leu Ala Arg Arg Leu Val Gln Ile Gly Ala Ser
    50                  55                  60

Asp Val Phe Ala Val Pro Gly Asp Phe Asn Leu Thr Leu Leu Asp Tyr
65                  70                  75                  80

Leu Ile Ala Glu Pro Gly Leu Thr Leu Val Gly Cys Cys Asn Glu Leu
                85                  90                  95

Asn Ala Gly Tyr Ala Ala Asp Gly Tyr Ala Arg Ser Arg Gly Val Gly
                100                 105                 110

Ala Cys Ala Val Thr Phe Thr Val Gly Gly Leu Ser Val Leu Asn Ala
            115                 120                 125

Ile Ala Gly Ala Tyr Ser Glu Asn Leu Pro Val Val Cys Ile Val Gly
    130                 135                 140

Gly Pro Asn Ser Asn Asp Tyr Gly Thr Asn Arg Ile Leu His His Thr
145                 150                 155                 160

Ile Gly Leu Pro Asp Phe Ser Gln Glu Leu Arg Cys Phe Gln Thr Ile
                165                 170                 175

Thr Cys Tyr Gln Ala Ile Asn Asn Leu Asp Asp Ala His Glu Gln
                180                 185                 190

Ile Asp Thr Ala Ile Ala Thr Ala Leu Arg Glu Ser Lys Pro Val Tyr
            195                 200                 205

Ile Ser Val Ser Cys Asn Leu Ala Gly Leu Ser His Pro Thr Phe Ser
    210                 215                 220

Arg Asp Pro Val Pro Met Phe Ile Ser Pro Arg Leu Ser Asn Lys Ala
225                 230                 235                 240

Asn Leu Glu Tyr Ala Val Glu Ala Ala Ala Asp Phe Leu Asn Lys Ala
                245                 250                 255
```

```
Val Lys Pro Val Met Val Gly Gly Pro Lys Ile Arg Val Ala Lys Ala
            260                 265                 270

Arg Glu Ala Phe Ala Ala Val Ala Asp Ala Ser Gly Tyr Pro Phe Ala
        275                 280                 285

Val Met Pro Ala Ala Lys Gly Leu Val Pro Glu His His Pro Arg Phe
    290                 295                 300

Ile Gly Thr Tyr Trp Gly Ala Val Ser Thr Thr Phe Cys Ala Glu Ile
305                 310                 315                 320

Val Glu Ser Ala Asp Ala Tyr Leu Phe Ala Gly Pro Ile Phe Asn Asp
                325                 330                 335

Tyr Ser Ser Val Gly Tyr Ser Leu Leu Leu Lys Arg Glu Lys Ala Val
                340                 345                 350

Ile Val Gln Pro Asp Arg Met Val Val Gly Asp Gly Pro Ala Phe Gly
                355                 360                 365

Cys Ile Leu Met Pro Glu Phe Leu Arg Ala Leu Ala Lys Arg Leu Arg
    370                 375                 380

Arg Asn Thr Thr Ala Tyr Asp Asn Tyr Arg Arg Ile Phe Val Pro Asp
385                 390                 395                 400

Arg Glu Pro Pro Asn Gly Lys Pro Asn Glu Pro Leu Arg Val Asn Val
                405                 410                 415

Leu Phe Lys His Ile Lys Gly Met Leu Ser Gly Asp Ser Ala Val Val
                420                 425                 430

Ala Glu Thr Gly Asp Ser Trp Phe Asn Cys Gln Lys Leu Arg Leu Pro
                435                 440                 445

Glu Gly Cys Gly Tyr Glu Phe Gln Met Gln Tyr Gly Ser Ile Gly Trp
    450                 455                 460

Ser Val Gly Ala Thr Leu Gly Tyr Ala Gln Ala Ala Lys Asp Lys Arg
465                 470                 475                 480

Val Ile Ala Cys Ile Gly Asp Gly Ser Phe Gln Val Thr Ala Gln Asp
                485                 490                 495

Val Ser Thr Met Leu Arg Cys Gly Gln Lys Ser Ile Ile Phe Leu Ile
                500                 505                 510

Asn Asn Gly Gly Tyr Thr Ile Glu Val Glu Ile His Asp Gly Pro Tyr
                515                 520                 525

Asn Val Ile Lys Asn Trp Asp Tyr Thr Gly Leu Val Asn Ala Ile His
                530                 535                 540

Asn Ser Glu Gly Asn Cys Trp Thr Met Lys Val Arg Thr Glu Glu Gln
545                 550                 555                 560

Leu Lys Glu Ala Ile Ala Thr Val Thr Gly Ala Lys Lys Asp Cys Leu
                565                 570                 575

Cys Phe Ile Glu Val Ile Val His Lys Asp Asp Thr Ser Lys Glu Leu
                580                 585                 590

Leu Glu Trp Gly Ser Arg Val Ser Ala Ala Asn Ser Arg Pro Pro Asn
                595                 600                 605

Pro Gln
    610

<210> SEQ ID NO 10
<211> LENGTH: 563
<212> TYPE: PRT
<213> ORGANISM: Saccromyces cerevisae

<400> SEQUENCE: 10

Met Ser Glu Ile Thr Leu Gly Lys Tyr Leu Phe Glu Arg Leu Lys Gln
1               5                   10                  15
```

```
Val Asn Val Asn Thr Val Phe Gly Leu Pro Gly Asp Phe Asn Leu Ser
         20                  25                  30

Leu Leu Asp Lys Ile Tyr Glu Val Glu Gly Met Arg Trp Ala Gly Asn
         35                  40                  45

Ala Asn Glu Leu Asn Ala Arg Tyr Ala Ala Asp Gly Tyr Ala Arg Ile
         50                  55                  60

Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ser Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Cys Thr
130                 135                 140

Ala Pro Ala Glu Ile Asp Arg Cys Ile Arg Thr Thr Tyr Val Thr Gln
145             150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Val Leu Ala
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Ser Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Asn
                325                 330                 335

Ile Ala Asp Ala Ala Lys Gly Tyr Lys Pro Val Ala Val Pro Ala Arg
                340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
            370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430
```

```
Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
        450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Val Met Leu Pro Val Phe Asp
        530                 535                 540

Ala Pro Gln Asn Leu Val Glu Gln Ala Lys Leu Thr Ala Ala Thr Asn
545                 550                 555                 560

Ala Lys Gln

<210> SEQ ID NO 11
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 3, 6, 18
<223> OTHER INFORMATION: r= a or g
<220> FEATURE:
<221> NAME/KEY: misc_feature
<222> LOCATION: 12, 21, 27
<223> OTHER INFORMATION: y= c or t
<220> FEATURE:
<221> NAME/KEY: misc_feature
<222> LOCATION: 9, 15, 30
<223> OTHER INFORMATION: n= any nucleotide base

<400> SEQUENCE: 11
aargargtna aygtngarca yatgttyggn gt                                 32
```